US006977295B2

(12) United States Patent
Belotserkovskii et al.

(10) Patent No.: US 6,977,295 B2
(45) Date of Patent: *Dec. 20, 2005

(54) LOCKED NUCLEIC ACID HYBRIDS AND METHODS OF USE

(75) Inventors: Boris Belotserkovskii, Mountain View, CA (US); Gurucharan Reddy, Fremont, CA (US); David A. Zarling, Menlo Park, CA (US)

(73) Assignee: Invitrogen Corporation, Carlsbad, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/557,423

(22) Filed: Apr. 21, 2000

(65) Prior Publication Data

US 2002/0094555 A1 Jul. 18, 2002

Related U.S. Application Data

(60) Provisional application No. 60/130,345, filed on Apr. 21, 1999.

(51) Int. Cl.[7] .............................................. C07H 21/04
(52) U.S. Cl. ................... 536/23.1; 435/183; 435/252.3; 435/325; 435/419; 530/550
(58) Field of Search .............................. 435/183, 252.3, 435/325, 419; 530/550; 536/23.1

(56) References Cited

U.S. PATENT DOCUMENTS 5,225,556 A * 7/1993 Barton
5,273,881 A * 12/1993 Sena et al.
5,482,836 A    1/1996 Cantor et al.
5,948,653 A * 9/1999 Pati et al.

FOREIGN PATENT DOCUMENTS

| WO | 93/05178 | 3/1993 |
| WO | 93/22443 | 11/1993 |
| WO | 95/01456 | 1/1995 |
| WO | 97/09069 | 3/1997 |
| WO | 97/14793 | 4/1997 |
| WO | 98/17827 | 4/1998 |
| WO | 98/42727 | 10/1998 |
| WO | 99/09045 | 2/1999 |

OTHER PUBLICATIONS

Helene et al (1990) Biochimica et Biophysica Acta 1049:99–125.*
Simonsson et al (1998) Nucleic Acids Research 26:1167–1172.*
Stryer, "Biochemistry", third edition, W. H. Freeman and Company, New York, 1988, pp. 76–78.*
Zubay, "Biochemistry" Addison–Wesley Publishing Company, Reading, Massachusetts, 1983, pp. 665–676.*
Wang et al., "Mutagenesis in mammalian cells induced by triple helix formation and transcription–coupled repair," Science 271:802–805 (1996).
Strobel and Dervan, "Site–specific cleavage of a yeast chromosome by oligonucleotide–directed triple–helix formation," Science 249:73–75 (1990).
Frank–Kamenetskii and Mirkin, "Triplex DNA structures," Annu. Rev. Biochem. 64:65–95 (1995).
Radding, "Homologous Pairing and Strand Exchange Promoted by E. coli RecA Protein", in Genetic Recombination, American Society for Microbiology, pp193–230 (1988).
Kowalczykowski and Eggleston, Homologous pairing and DNA strand–exchange proteins, Annu. Rev. Biochem. 63:991–1043 (1994).
Pati, et al., in Encyclopedia of Cancer, Bertino, ed. (Academic Press, San Diego) vol. III, pp 1601–1625 (1997).
Bazemore et al., "Kinetic analysis of pairing and strand exchange catalyzed by RecA. Detection by fluorescence energy transfer," J. Biol. Chem. 272:14672–14682 (1997).
Rougee et al., "Kinetics and thermodynamics of triple–helix formation: effects of ionic strength and mismatches," Biochem. 31:9269–9278 (1992).
Ferrin and Camerini–Otero, "Selective cleavage of human DNA: RecA–assisted restriction endonuclease (RARE) cleavage," Science 254:1494–1497 (1991).
Voloshin, et al., "Homologous DNA pairing promoted by a 20–amino acid peptide derived from RecA," Science 272:868–872 (1996).
Li, et al., "Recombination activities of HsDmc1 protein, the meiotic human homolog of RecA protein," Proc. Natl. Acad. Sci. USA 94:11221–11226 (1997).
Beattie et al., "Uptake of homologous single–stranded fragments by superhelical DNA. II. Characterization of the reaction," J. Molec. Biol. 116:783–803 (1977).
Radding, et al., "Uptake of homologous single–stranded fragments by superhelical DNA. IV. Branch migration," J. Molec. Biol. 116:825–839 (1977).
Sena and Zarling, "Targeting in linear DNA duplexes with two complementary probe strands for hybrid stability," Nature Genet. 3:365–372 (1993).
Jayasena and Johnston, "Complement–stabilized D–loop. RecA–catalyzed stable pairing of linear DNA molecules at internal sites," J. Molec. Biol. 230:1015–1024 (1993).

(Continued)

Primary Examiner—James Ketter
Assistant Examiner—David A. Lambertson

(57) ABSTRACT

The invention relates to methods for inhibiting, cloning, modifying or labelling an endogenous DNA sequence using compositions comprising recombinases in combination with exogenous polynucleotides containing "anchoring" or "locking" sequences. The anchoring sequences serve to stabilize structures formed by the exogenous polynucleotides and the endogenous DNA. The stabilized structure thus can either serve to regulate gene transcription or replication, or can allow the endogenous sequences to be labelled or pulled out, i.e. cloned, or modified.

25 Claims, 20 Drawing Sheets

OTHER PUBLICATIONS

Lee, et al., "A physical study by electron microscopy of the terminally repetitious, circularly permuted DNA from the coliphage particles of Escherichia coli 15," *J. Molec. Biol.* 48:1–22 (1970).

Sundquist, and Klug. "Telomeric DNA dimerizes by formation of guanine tetrads between hairpin loops," *Nature* 342:825–829 (1989).

Haniford and Pulleyblank, "Facile transition of poly[d(TG)× d(CA)] into a left-handed helix in physiological conditions," *Nature* 302:632–634 (1983).

Panyutin and Hsieh, "Formation of a single base mismatch impedes spontaneous DNA branch migration," *J. Molec. Biol.* 230:413–424 (1993).

Panyutin and Hsieh, "The kinetics of spontaneous DNA branch migration," *Proc. Natl. Acad. Sci. USA* 91:2021–2025 (1994).

Panyutin et al., "A pivotal role for the structure of the Holliday junction in DNA branch migration," *EMBO J.* 14:1819–1826 (1995).

Lilley and Clegg, "The structure of the four-way junction in DNA," *Annu. Rev. Biophys. Biomol. Struct.* 22:299–328 (1993).

Dayn, et al., "Intramolecular DNA triplexes: Unusual sequence requirements and influence on DNA polymerization", *Proc. Natl. Acad. Sci. USA* 89:11406–11410 (1992).

Honigberg, et al., "Ability of RecA protein to promote a search for rare sequences in duplex DNA," *Proc. Natl. Acad. Sci. USA* 83:9586–9590 (1986).

Rigas et al., "Rapid plasmid library screening using RecA-coated biotinylated probes," *Proc. Natl. Acad. Sci. USA* 83:9591–9595 (1986).

Balatskaya, et al., "Alternative-strand triplex formation: modulation of binding to matched and mismatched duplexes by sequence choice in the Pu–Pu–Py block," *Biochemistry* 35:13328–13337 (1996).

Belotserkovskii and Johnston, "Capture in the gel: intermoleculare triplex formation during gel electrophoresis," *Electrophoresis* 17:1528–1534 (1996).

Belotserkovskii and Frank–Kamenetskii, "Study of pH-dependent structural transition in telomeric sequences by two-dimensional gel electrophoresis," *Electrophoresis* 14:266–270 (1993).

Belotserkovskii et al., "Kinetic trapping of H–DNA by oligonucleotide binding", *Nucleic Acids Res* 20:1903–1908 (1992).

Belotserkovskii et al., "Formation of intramolecular triplex in homopurine–homopyrimidine mirror repeats with point substitutions," *Nucleic Acids Res* 18:6621–6624 (1990).

Belotserkovskii and Johnston, "A random–walk model for retardation of interacting species during gel electophoresis: implications for gel–shift assays," *Biophys J.* 73(3):1288–1298 (1997).

Belotserkovskii, et al., "DNA Hybrids Stabilized by Heterologies," *Biochemistry* 38:10785–10792 (1999).

Gupta, et al., "Activities of human recombination protein Rad51," *Proc. Natl. Acad. Sci. USA* 94:463–468 (1997).

* cited by examiner

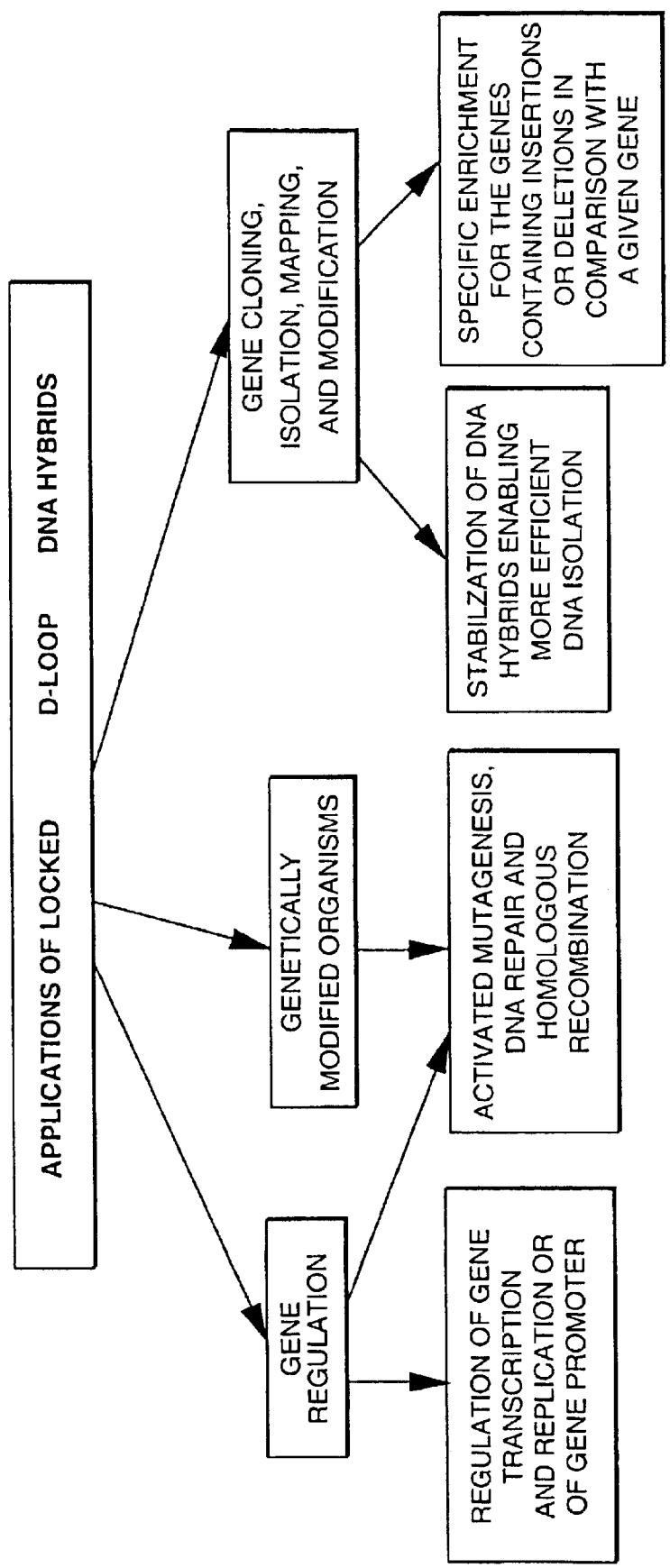
FIG._1

FIG._2A
Target DNA completely homolgous
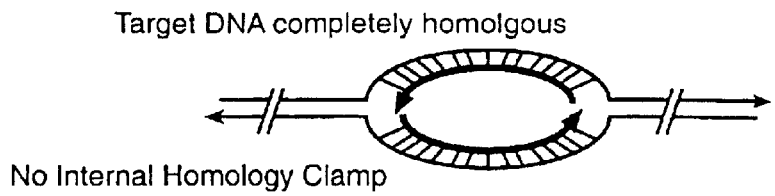
No Internal Homology Clamp
FIG._2B
duplex-forming heterologous insert
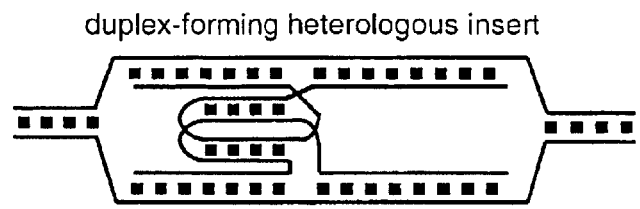
FIG._2C
triplex-forming heterologous insert
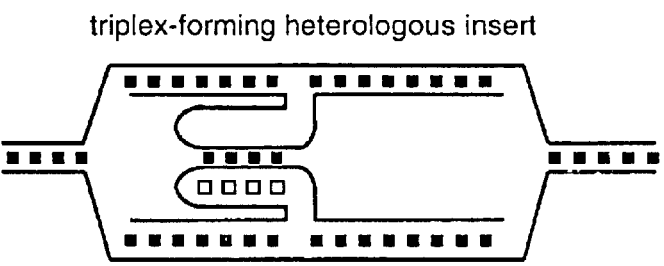
FIG._2D
quadruplex-forming heterologous insert
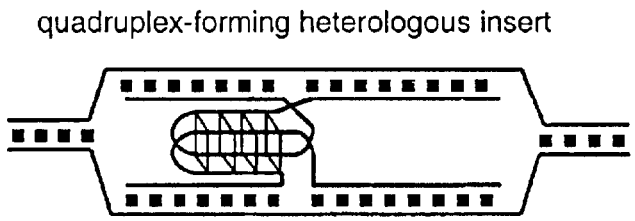
FIG._2E
heterologous insert which forms triplex with secondary probe
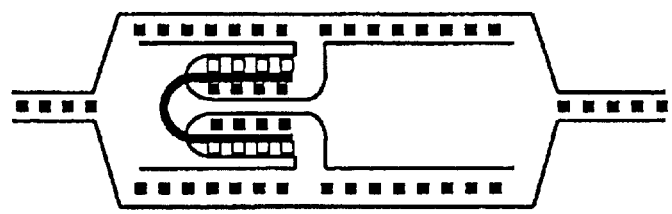
FIG._2F
Target DNA with an insertion
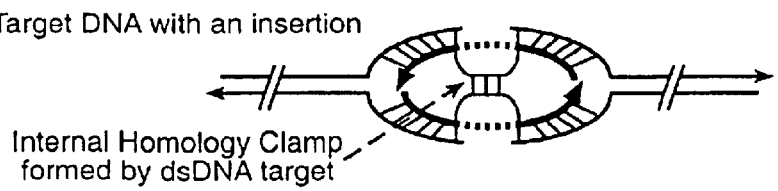
Internal Homology Clamp formed by dsDNA target

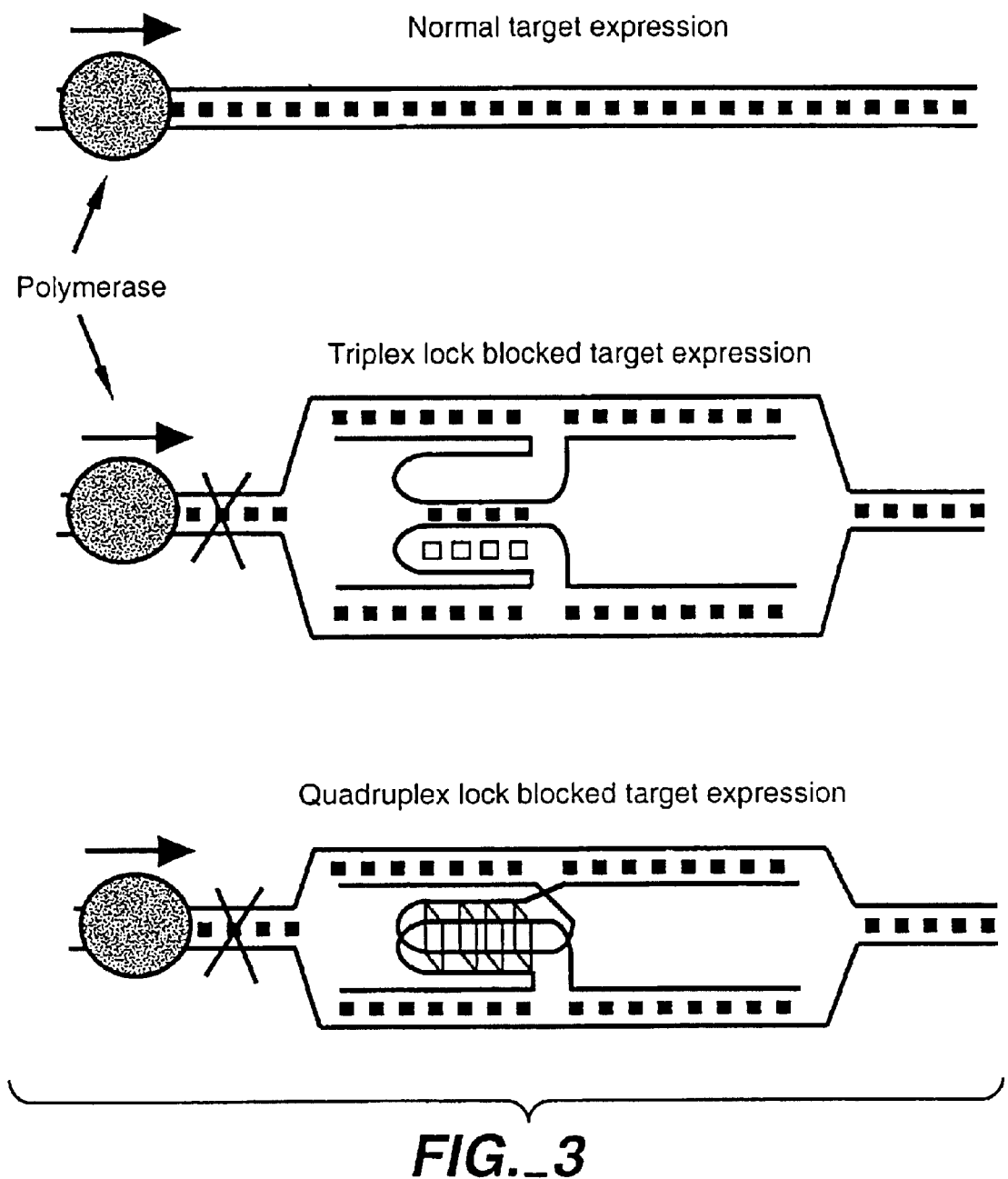
FIG._3

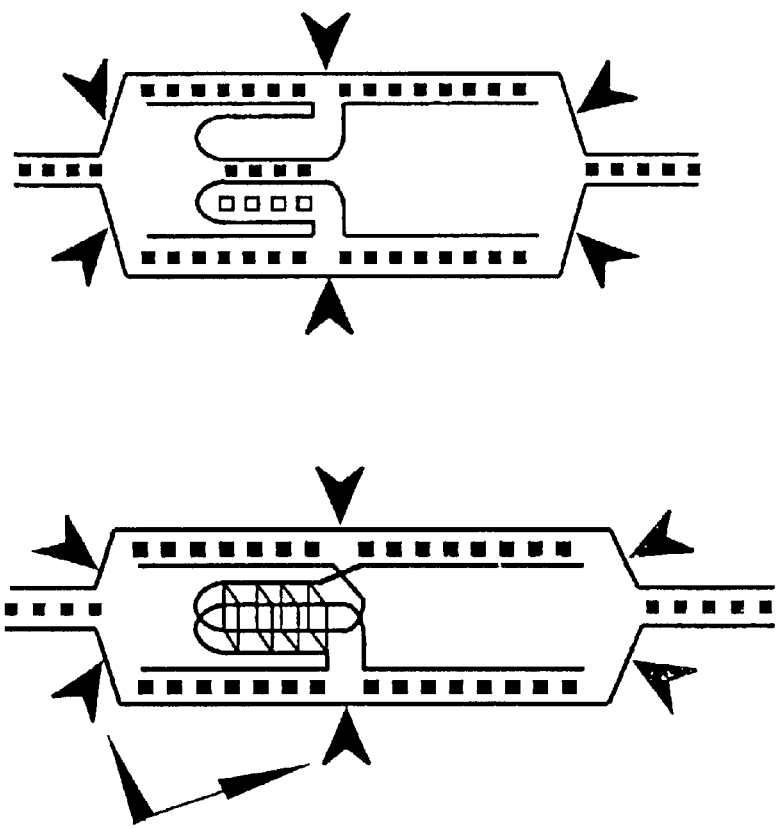
Hybrid recognition by
nucleic acid repair,
nucleic acid recombination,
and resolution enzymes
FIG._4

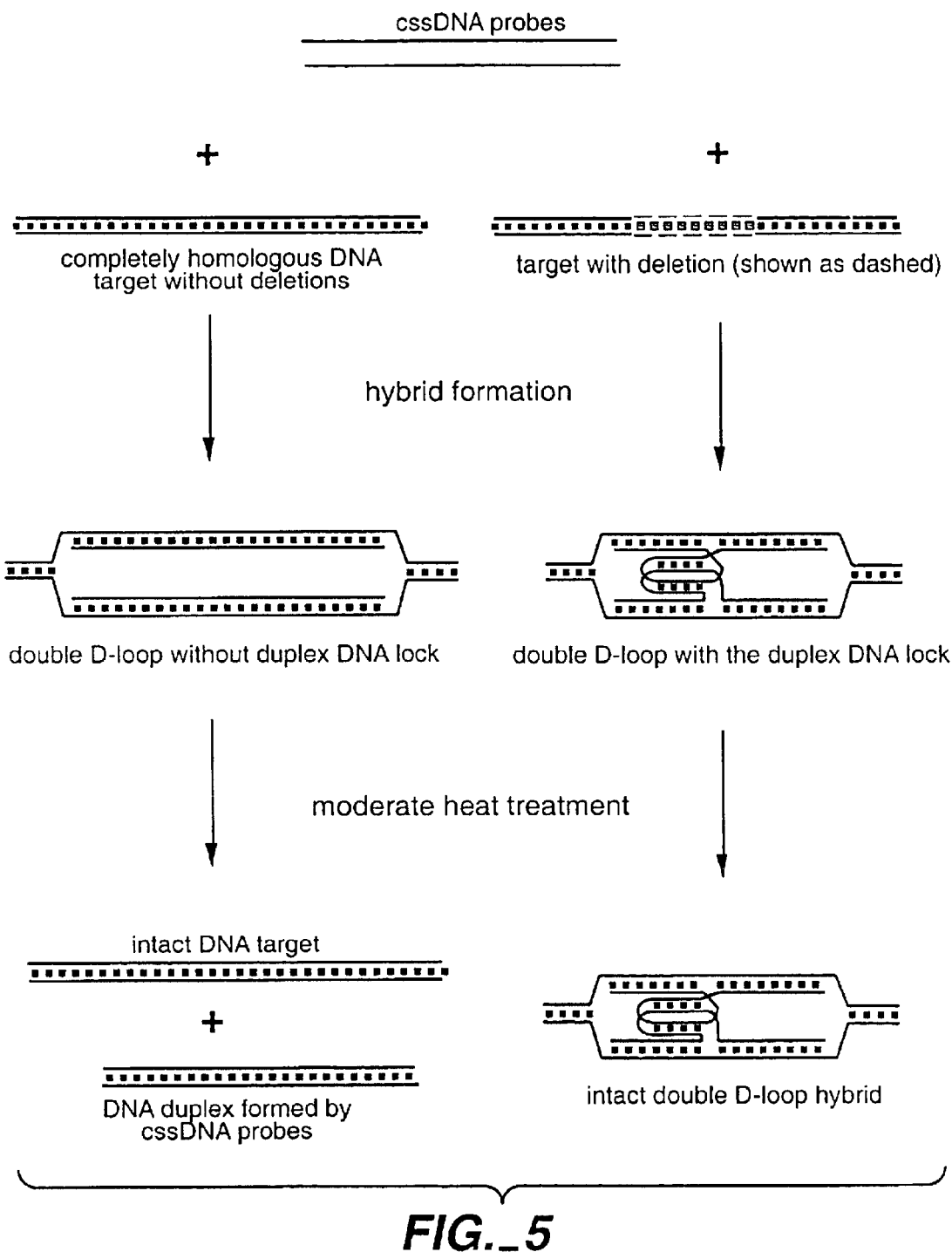
FIG._5

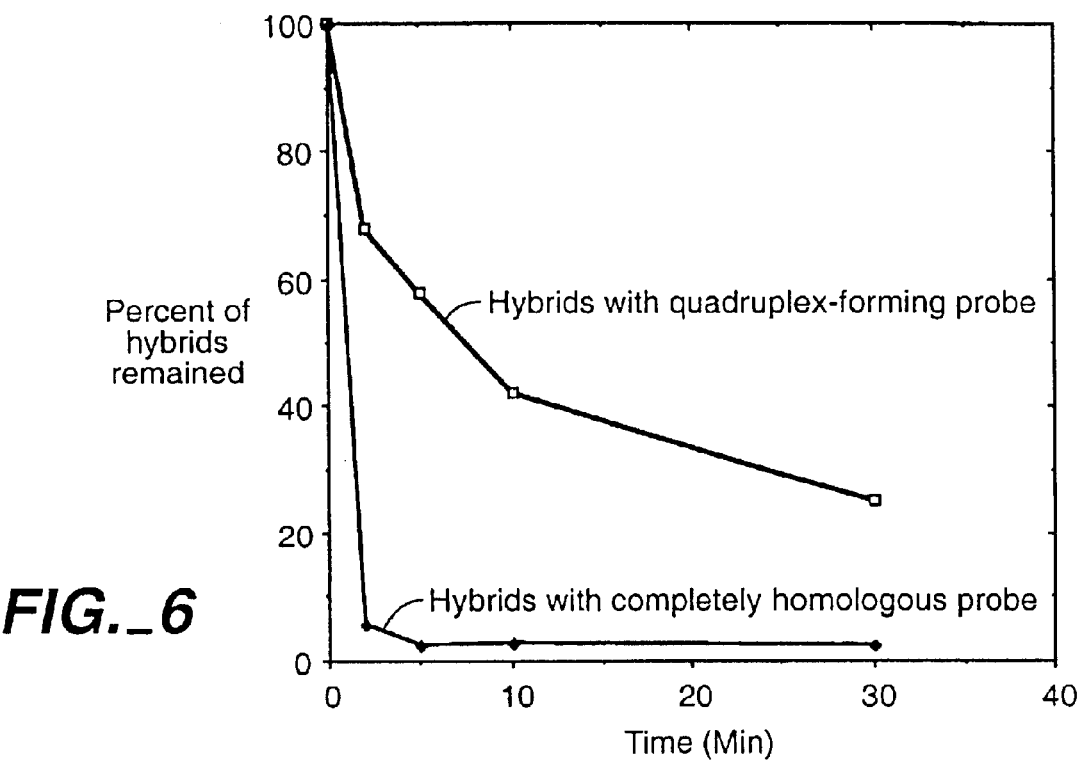
FIG._6
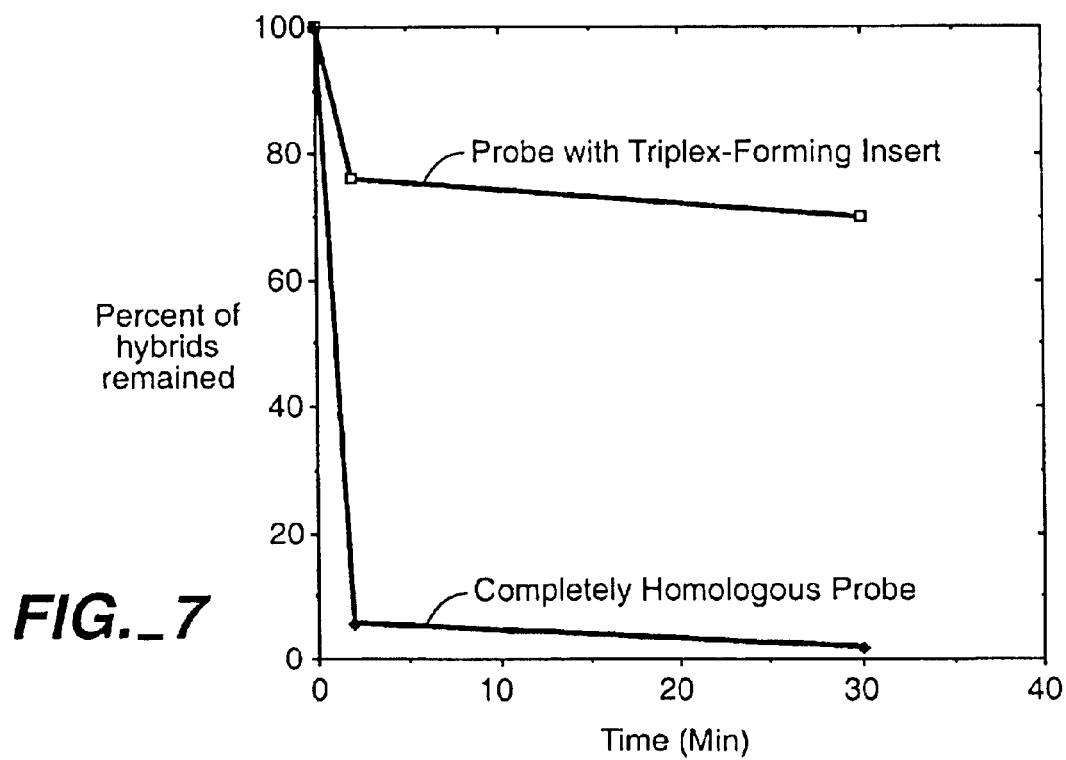
FIG._7

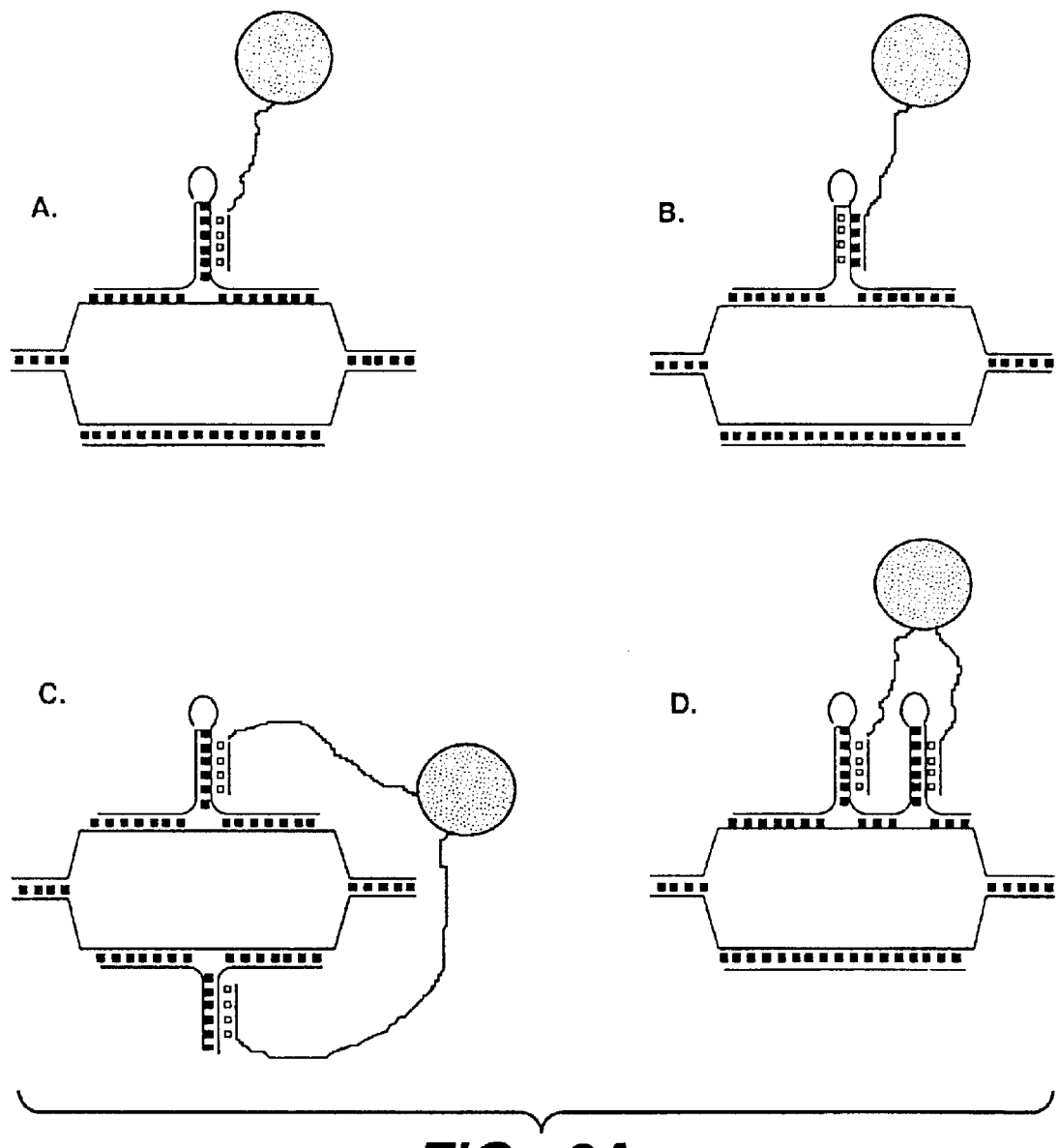
FIG._8A

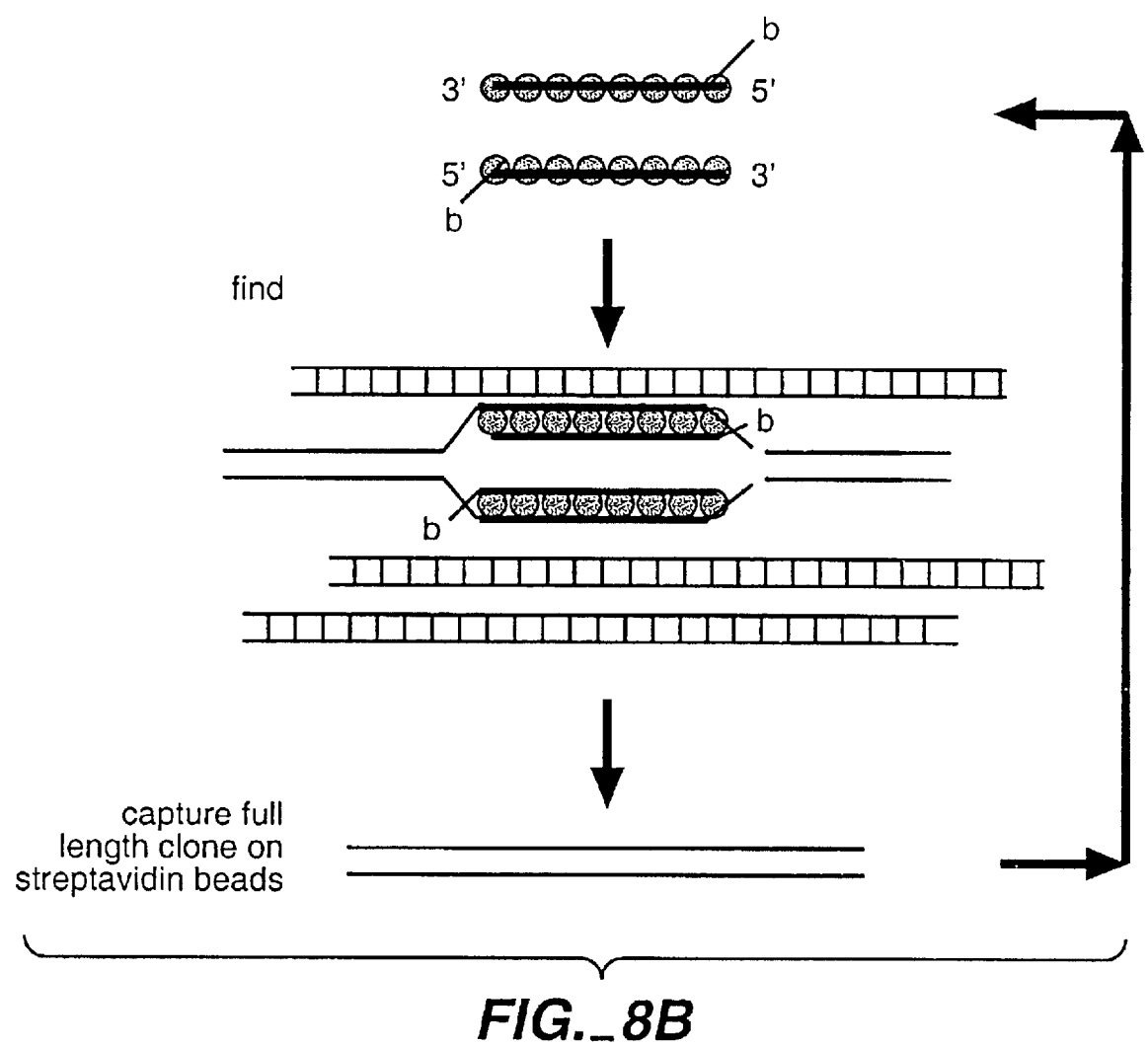
FIG._8B

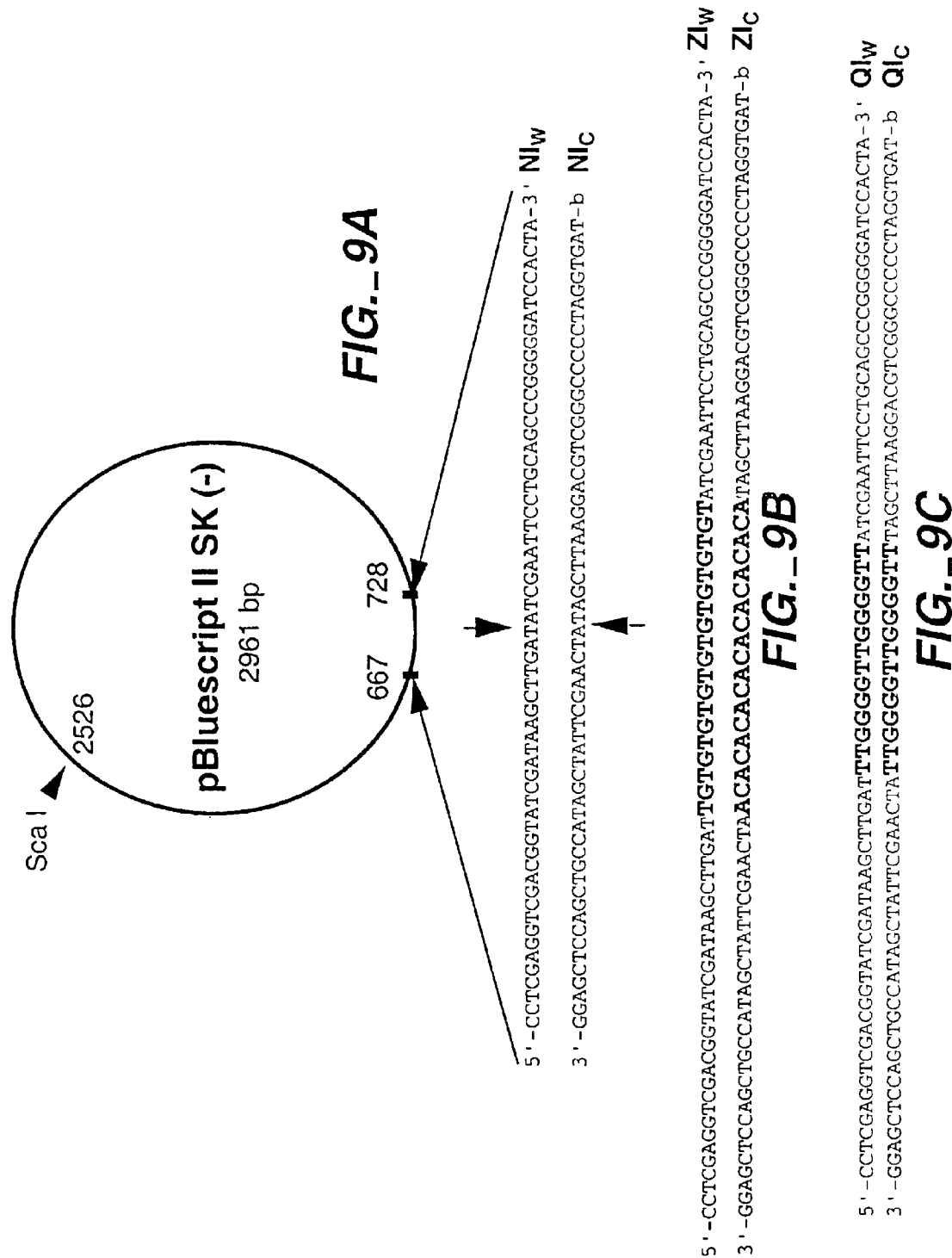

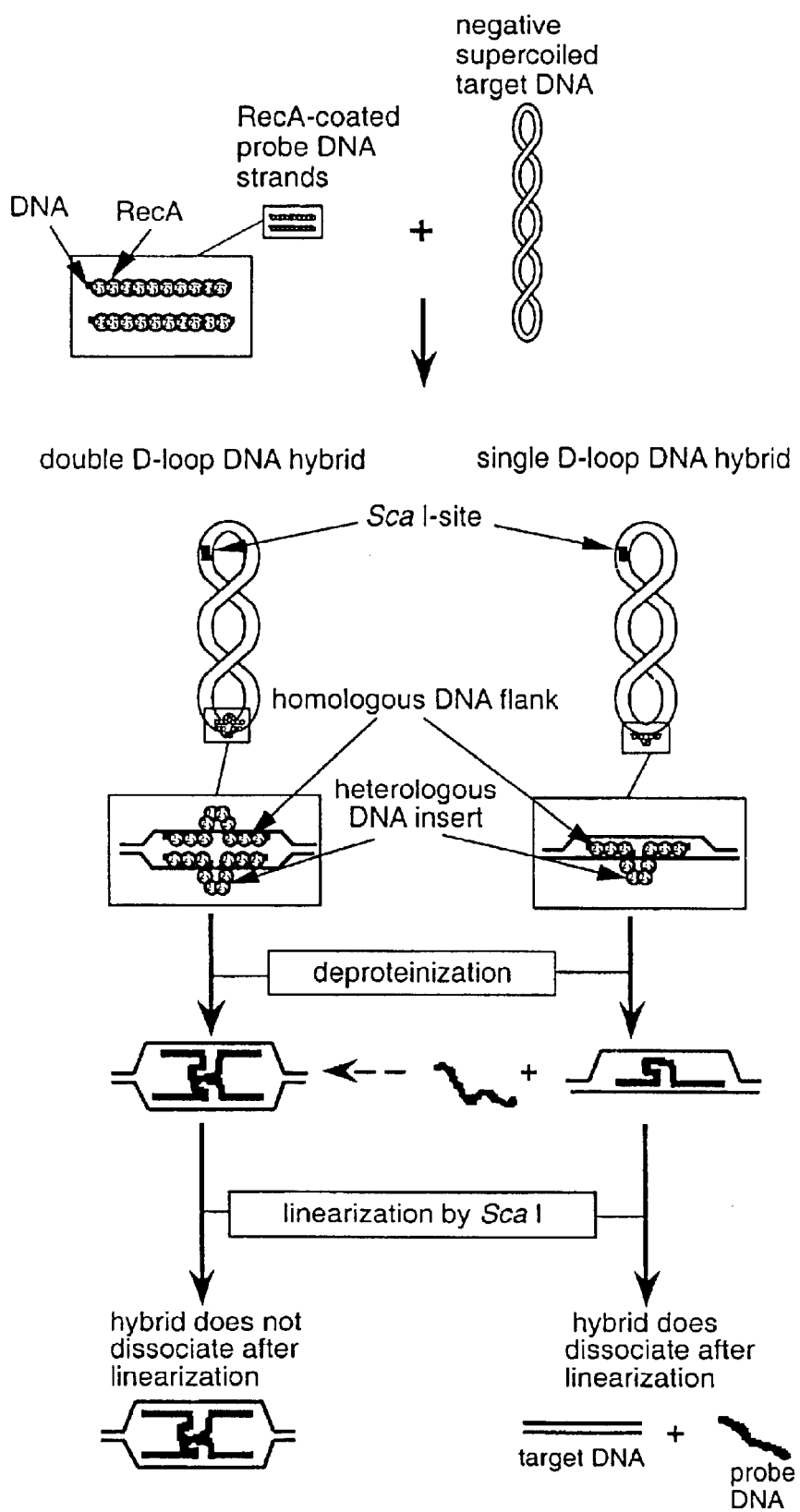
FIG._10

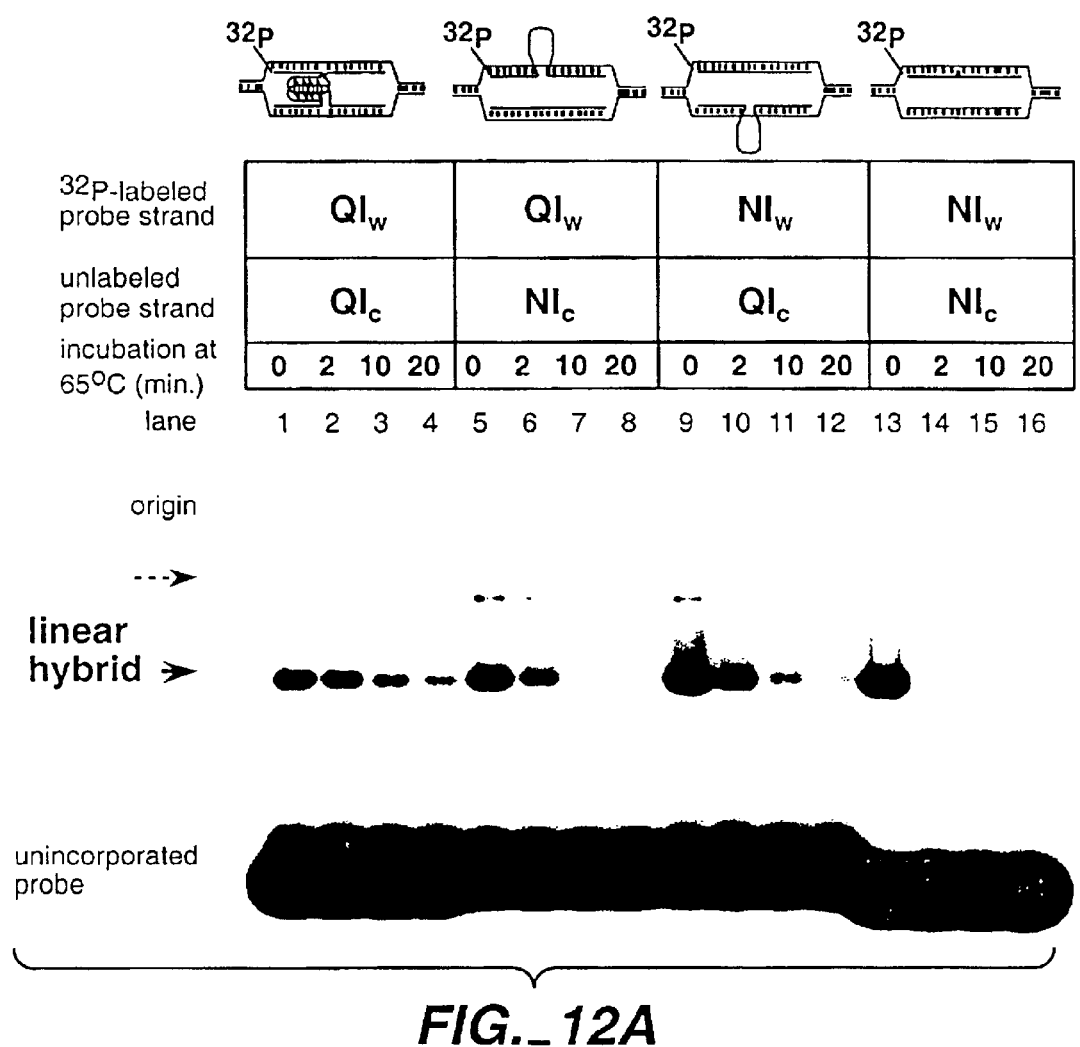
FIG._12A

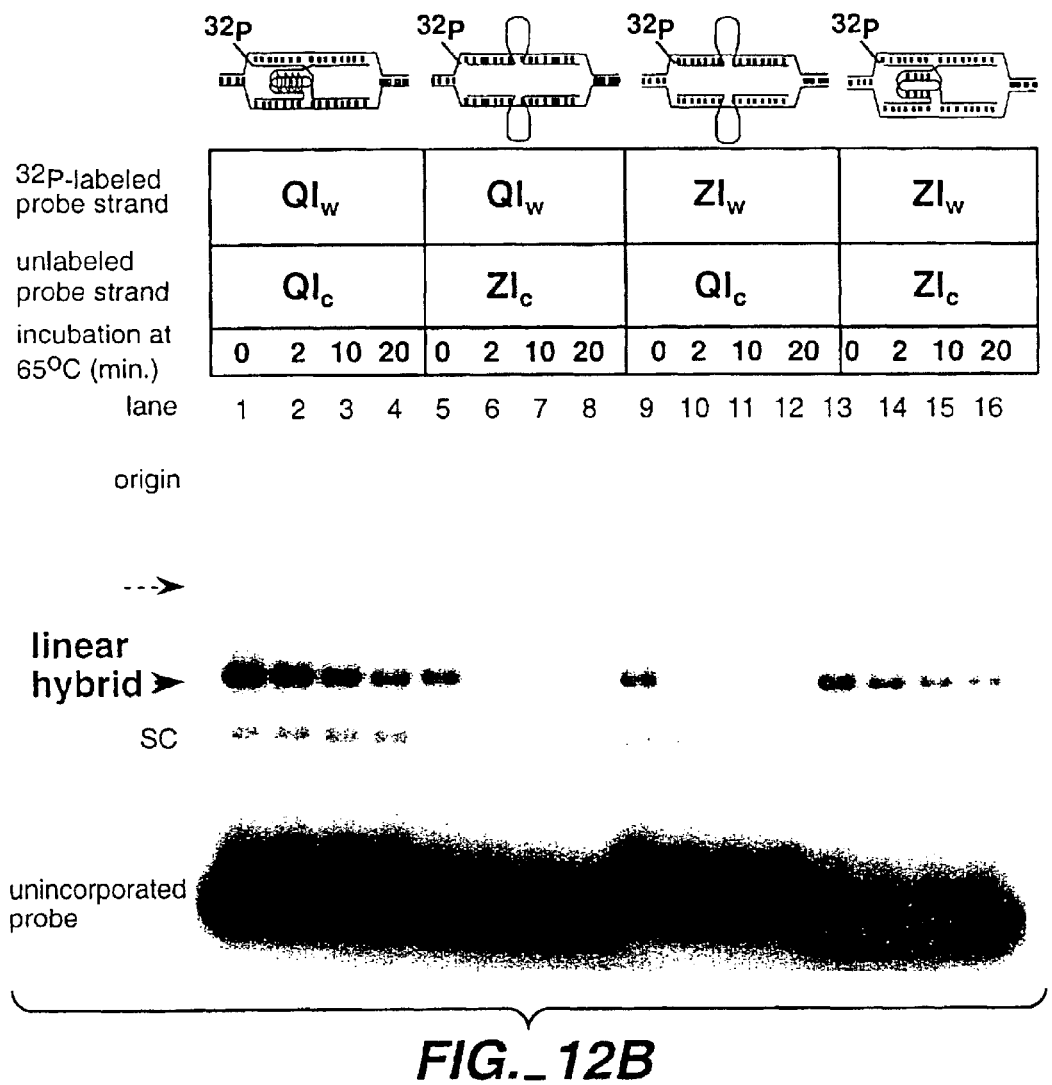
FIG._12B

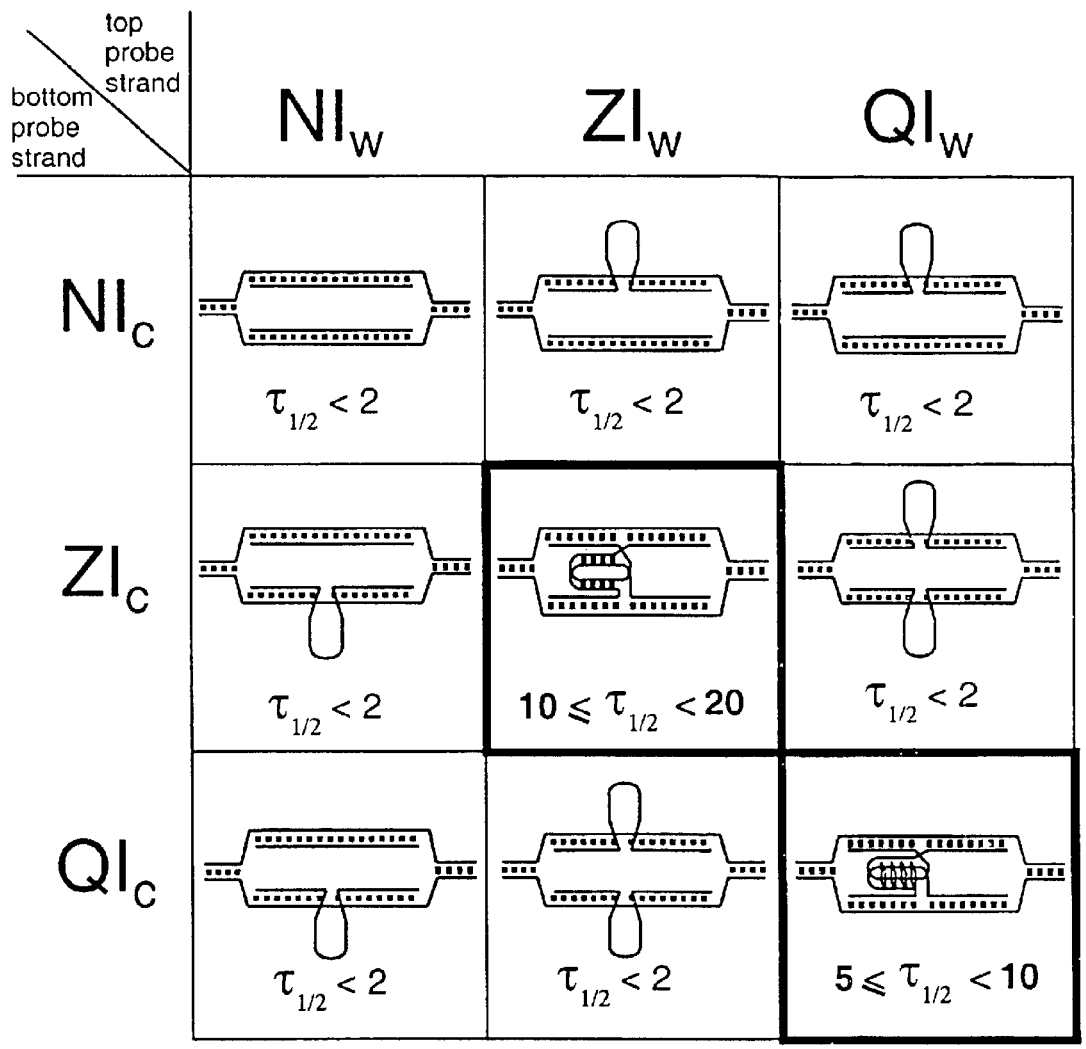
NI = No DNA Insert
ZI = Z-DNA forming Insert
QI = Quadruplex-DNA forming Insert
w = Watson DNA strand
c = Crick DNA strand
$\tau_{1/2}$ = double D-loop DNA hybrid apparent half-life time (min.)
FIG._13

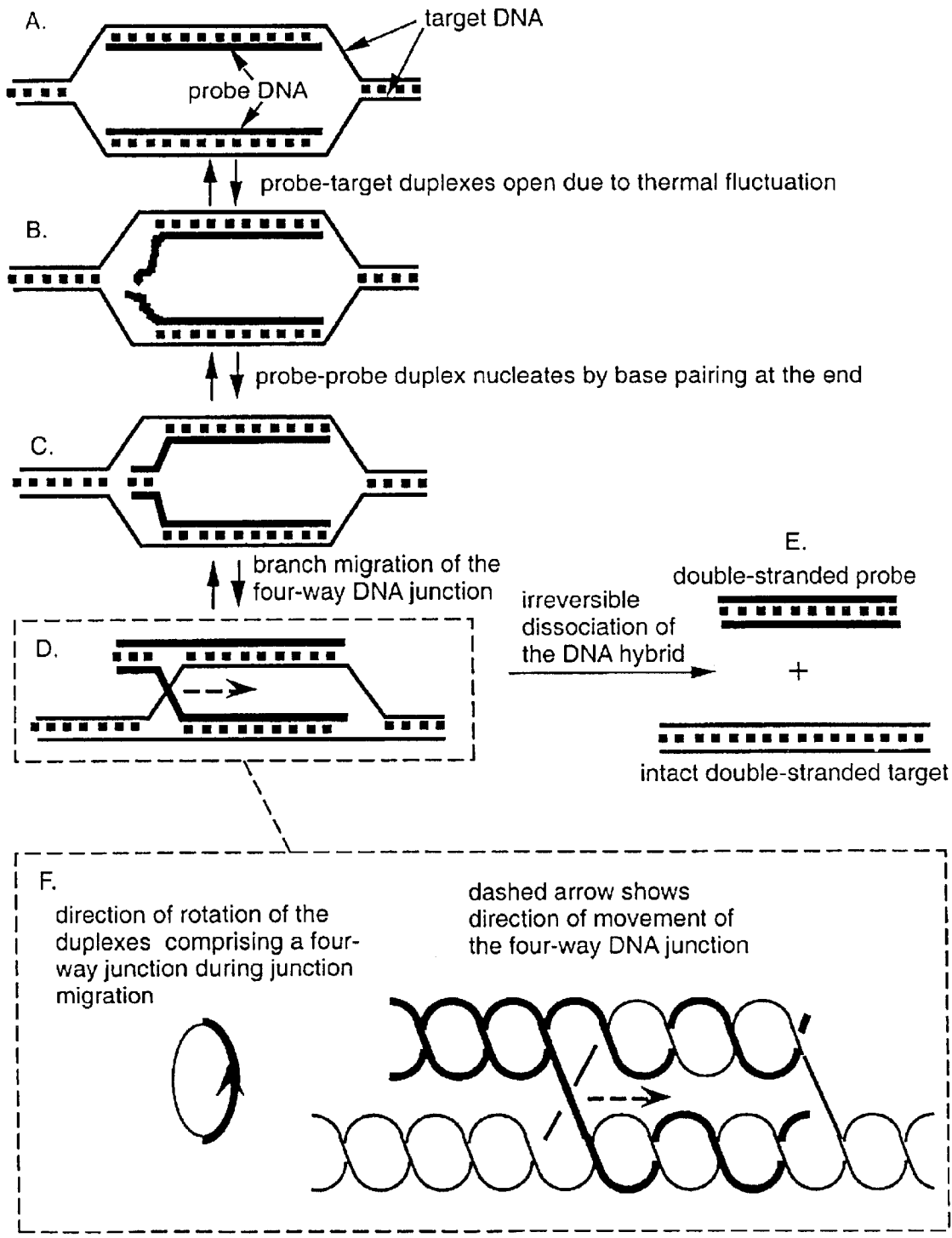
FIG._14

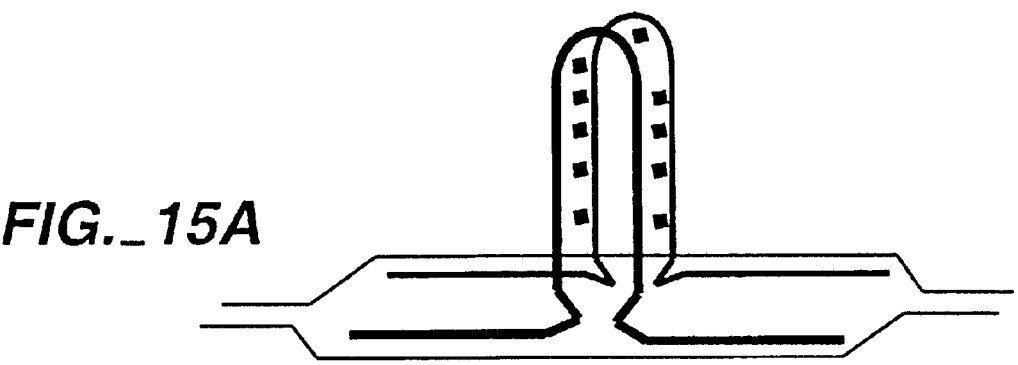
FIG._15A
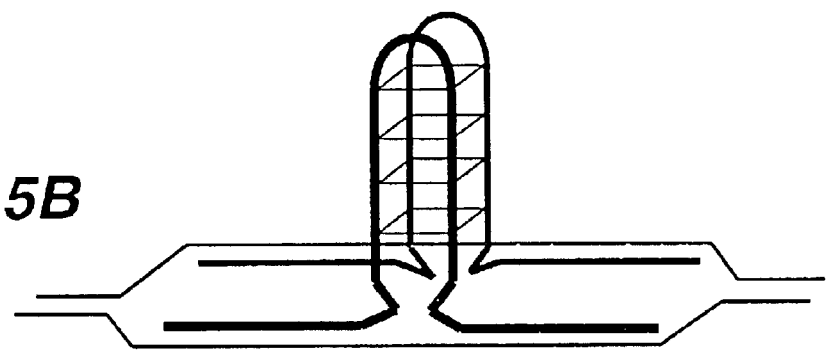
FIG._15B
5'-AGCTTCCCTCCTCCCTCCCCTAATACCCCACCCACCACCCG-3'
3'-AGGGAGGAGGGAGGGGATTATGGGGTGGGTGGTGGGCTTAA-5'
triplex-forming insert
FIG._16

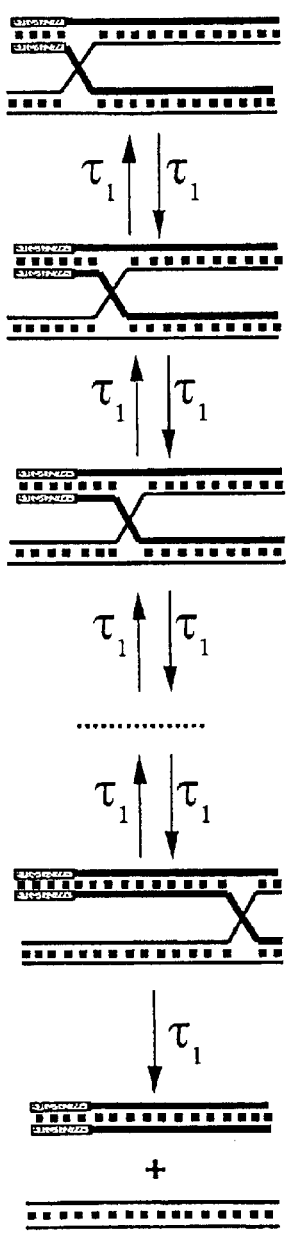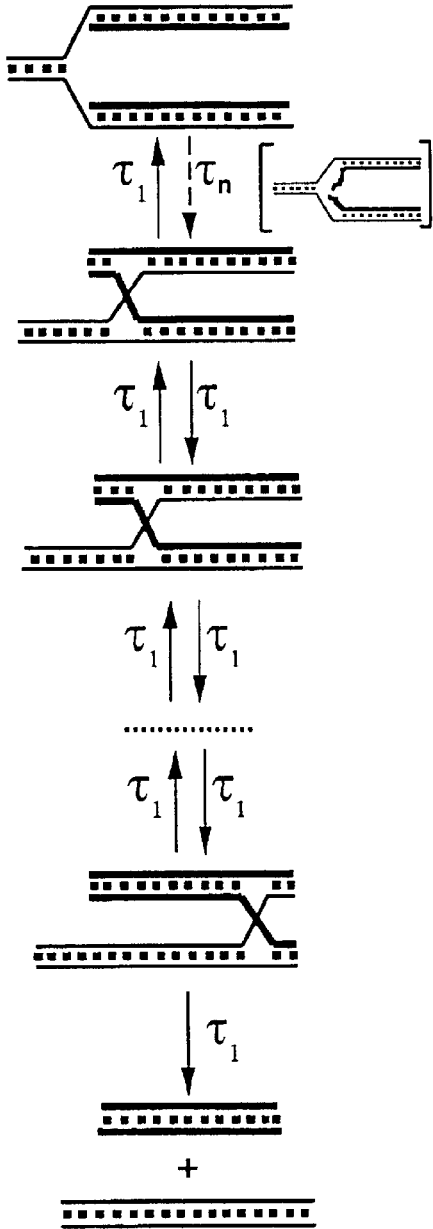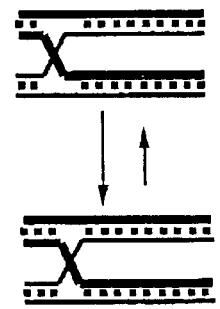
FIG._17A  FIG._17B  FIG._17C

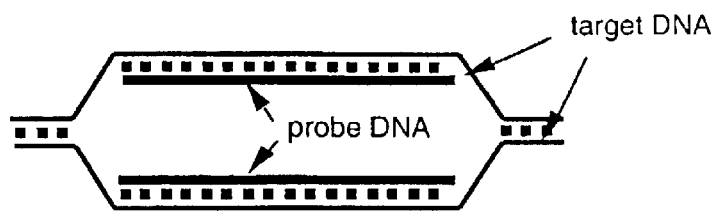
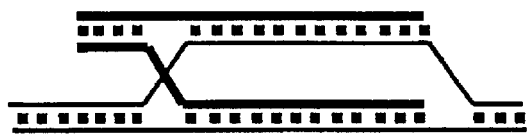
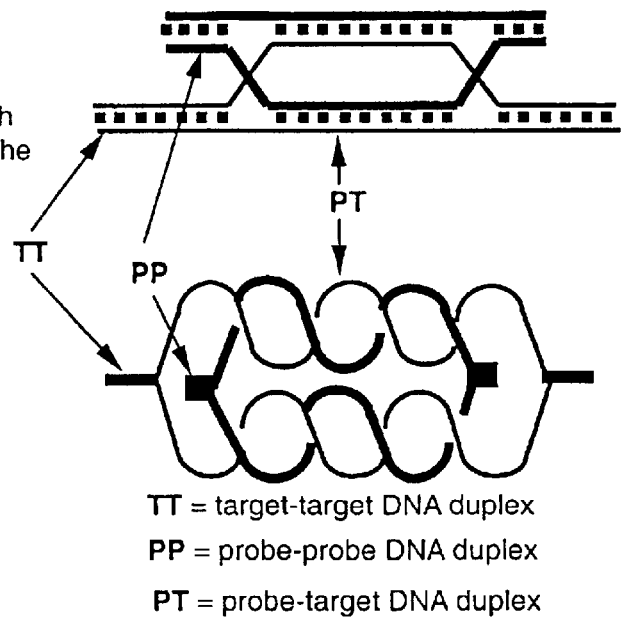
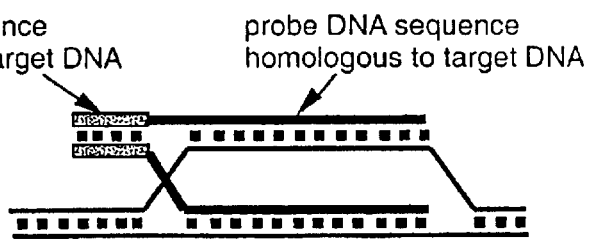
FIG._18

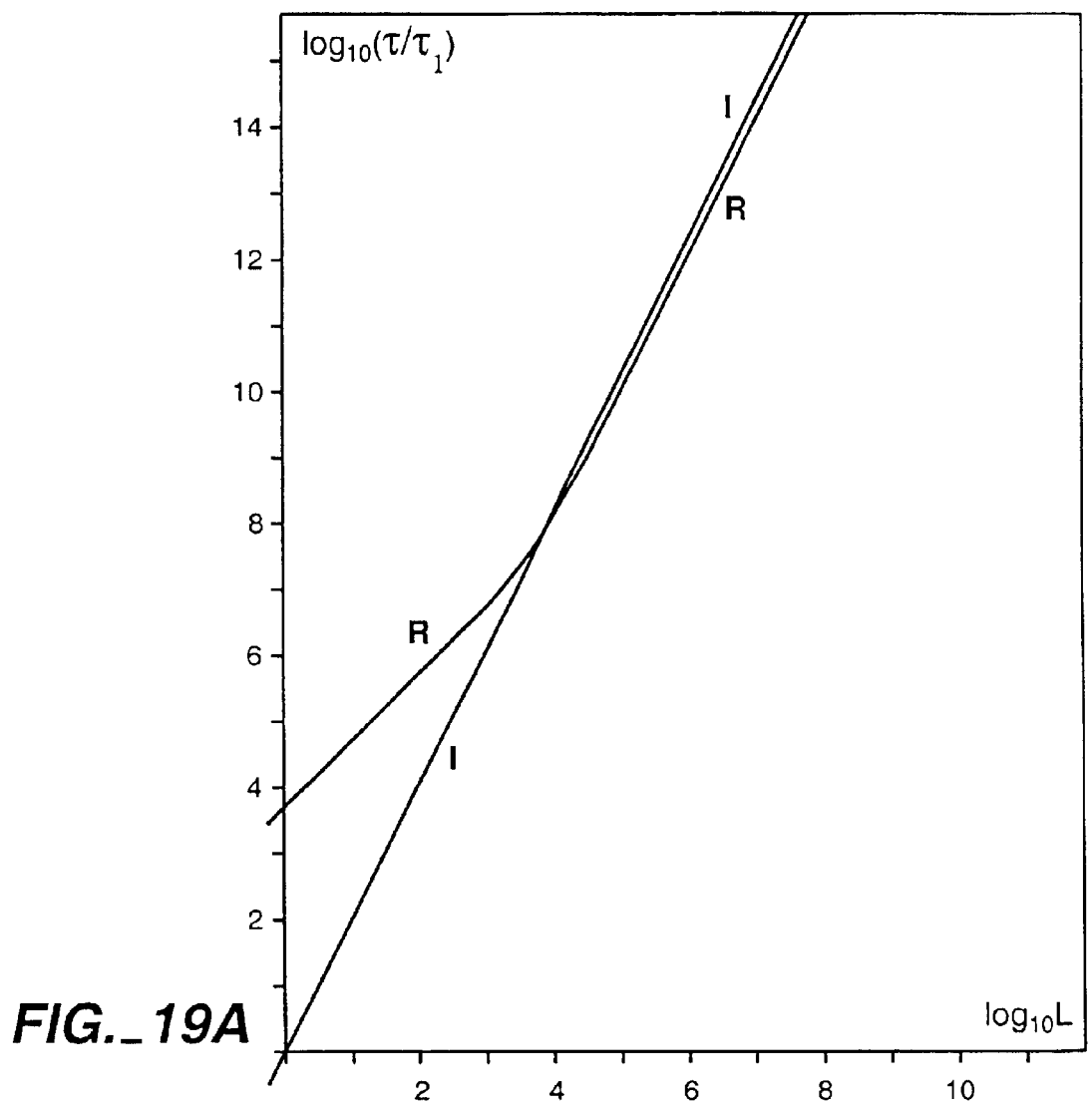
FIG._19A
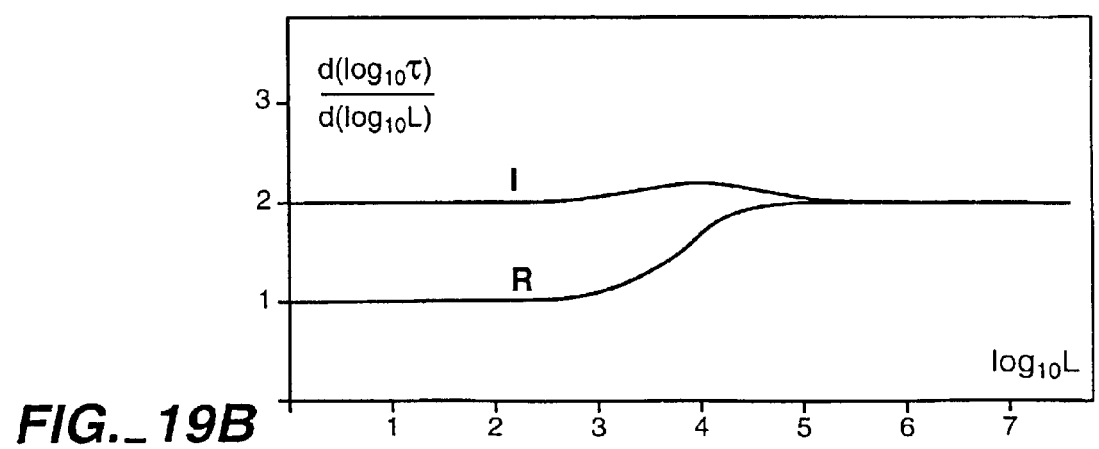
FIG._19B

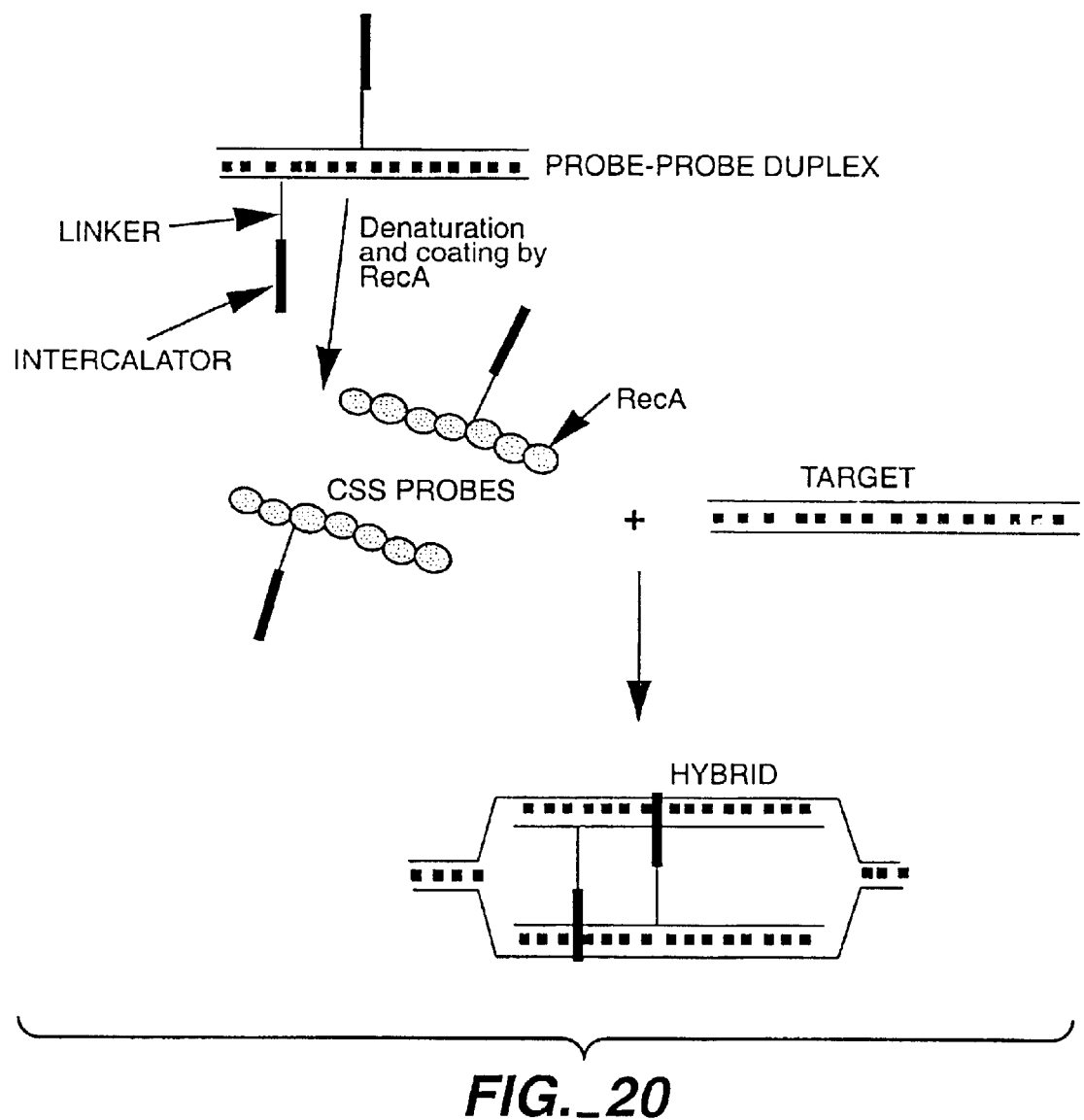
FIG._20

```
                          SEQUENCE LISTING

<160> NUMBER OF SEQ ID NOS: 17

<210> SEQ ID NO 1
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
cctcgaggtc gacggtatcg ataagcttga tatcgaattc ctgcagcccg ggggatccac      60
ta                                                                    62

<210> SEQ ID NO 2
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tagtggatcc cccgggctgc aggaattcga tatcaagctt atcgataccg tcgacctcga      60
gg                                                                    62

<210> SEQ ID NO 3
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cctcgaggtc gacggtatcg ataagcttga ttgtgtgtgt gtgtgtgtgt atcgaattcc      60
tgcagcccgg gggatccact a                                               81

<210> SEQ ID NO 4
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tagtggatcc cccgggctgc aggaattcga tacacacaca cacacacaca atcaagctta     60
tcgataccgt cgacctcgag g                                               81

<210> SEQ ID NO 5
<211> LENGTH: 76
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 5
cctcgaggtc gacggtatcg ataagcttga tttggggttg gggttatcga attcctgcag      60
cccgggggat ccacta                                                     76

<210> SEQ ID NO 6
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tagtggatcc cccgggctgc aggaattcga tttggggttg gggttatcaa gcttatcgat      60
accgtcgacc tcgagg                                                     76

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
acacacacac acacacaca                                                  19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgtgtgtgtg tgtgtgtgt                                                  19

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
ttggggttgg ggtt                                                       14

<210> SEQ ID NO 10
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agcttccctc ctccctcccc taataccccca cccaccaccc g                        41

<210> SEQ ID NO 11
```

```
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
aattcgggtg gtgggtgggg tattagggga gggaggaggg a                    41

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Gln Ile Arg Met Lys Ile Gly Val Met Phe Gly Asn Pro Glu Thr
  1               5                  10                  15

Thr Thr Gly Gly
           20

<210> SEQ ID NO 13
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro Leu Leu Leu Ala Leu Val Asn Gln Ile Arg Met Lys Ile Gly Val
  1               5                  10                  15

Met Phe Gly Asn Pro Glu Thr Thr Thr Gly Gly
               20                  25

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Pro Leu Leu Leu Ala Leu Val
  1               5

<210> SEQ ID NO 15
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 tatac                                                             5

<210> SEQ ID NO 16
<211> LENGTH: 5
<212> TYPE: DNA
<213> ORGANISM: Artificial Sequence
<220> FEATURE:
<223> OTHER INFORMATION: Description of Artificial Sequence: Synthetic
```

```
            oligonucleotide

<400> SEQUENCE: 16 gtata                                                                    5

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
            oligonucleotide

<400> SEQUENCE: 17
gggtggtggg tggggtatta ggggagggag gaggg                                  35
```

LOCKED NUCLEIC ACID HYBRIDS AND METHODS OF USE

This application claims the benefit of the filing date of U.S. provisional application Ser. No. 60/130,345, filed Apr. 21, 1999, pending, expressly incorporated by reference.

This invention was made with Government support under Grant Nos. GM-38424 awarded by the National Institutes of Health. The Government has certain rights in this invention.

FIELD OF THE INVENTION

The invention relates to methods of regulating, cloning, labelling, or modifying an endogenous DNA sequence using novel compositions comprising recombinases in combination with exogenous polynucleotides containing "anchoring" or "locking" sequences. The anchoring sequences serve to stabilize structures formed by the exogenous polynucleotides and the endogenous DNA. The stabilized structure thus can either serve to regulate gene transcription or replication, or can allow the endogeneous sequences to be labelled or pulled out, i.e. cloned, or otherwise modified.

BACKGROUND OF THE INVENTION

Sequence-specific targeting of endogenous nucleic acids can be a tool for example in the regulation of gene expression, sequence-specific mutagenesis, gene reprogramming, gene labeling, gene isolation and/or gene modification.

One class of oligonucleotides used for sequence-specific nucleic acid targeting are triplex-forming oligonucleotides (TFO). These oligonucleotides can form a triple-stranded helix (triplex) with the target nucleic acids via Hoogsteen or reverse-Hoogsteen interactions, with purines in the target, without disrupting the hydrogen bonds between strands in the target duplex. The triplexes, when localized downstream of the promoter (or the origin of replication) generally prevent transcription (or replication) of the target sequence. Thus, these triplex-forming oligonucleotides have been explored as tools for regulation of gene expression (for review see Helene and Toulme, Biochem. Biophys. Acta 1049:99 (1990)). TFOs also have been used for site-directed mutagenesis (Wang et al., Science 271:802 (1996)), gene isolation (Cantor et al., U.S. Pat. No. 5,482,836) and site-specific DNA cleavage (Strobel and Dervan, Science 249:73 (1990)).

However, there are severe limitations to the utility of TFOs because of the sequence dependence of triplex formation. For all known TFOs (both with natural and artificial bases and backbones) the target must comprise homopurine-homopyrimidine strands (i.e. the Watson strand is solely purines and the Crick strand is solely pyrimidines), with some small variations allowed (for review, see Frank-Kamenetskii and Mirkin, Annu. Rev. Biochem. 64:65 (1995)). This severely limits the applicability of these techniques.

In contrast, there are recombination enzymes (for example, the RecA family of recombinases) which can form nucleoprotein filaments with any oligonucleotide, and can subsequently target any selected sequence. These nucleoprotein filaments presumably disrupt the hydrogen bonds between the strands in the target duplex, and form stable sequence-specific complexes with one or both of these strands primarily via Watson-Crick interactions (though the presence of some additional interactions between nucleic acids within the complex has not been ruled out). (For review see Radding, Homologous Pairing and Strand Exchange Promoted by *E. coli* RecA Protein, in Genetic Recombination, American Society for Microbiology, pp193–230, 1988; and Kowalczykowski and Eggleston, Annu. Rev. Biochem. 63:991–1043 (1994)).

The additional advantage of the nucleoprotein filament over TFOs is the fact that these nucleoprotein filaments exhibit far more rapid initiation of the complex formation, i.e. the formation with the target sequence. For example, for RecA-covered filaments the on-rate constant of the first bimolecular step of the reaction is about the same as for Watson-Crick duplex formation (Bazemore et al., J. Biol. Chem. 272:14672 (1997)). This is one to three orders of magnitude larger than the rate for triplex formation (Rougee et al., Biochem. 31:9269 (1992)). This suggests that these filaments can be used in significantly smaller concentrations than the TFOs to achieve the same effect. Similarly, nucleoprotein filaments have been used for RecA-assisted restriction endonuclease (RARE) cutting of chromosomes (Ferrin and Camerini-Otero, Science 254:1494 (1991)).

However, for relatively short oligonucleotides, these kinds of complexes usually dissociate very rapidly after the RecA is removed, unless the target is strongly negatively supercoiled (which is unlikely to be the case for many eukaryotic targets, which are globally relaxed). Since deproteinization of the structure can occur spontaneously in living cells, the stability of these structures after deproteinization varies. In addition, deproteinized complexes are expected to be more convenient for some manipulations with DNA in vitro.

The ability to selectively inhibit the growth of a subset of cells in a mixture of cells has many applications both in culture and in vivo. Where two sets of cells have distinguishing characteristics, such as tumor cells which require expression of one or more genes, which are not expressed in normal cells or only expressed at a low level, there is substantial interest in being able to selectively inhibit the proliferation of the tumor cells. Where groups of cells are differentiating, and at one level of differentiation, expression of a particular gene is required, the ability to inhibit the expression of that gene can be of interest. Where cells are infected by viruses, parasites or mycoplasmas, the selective ability to inhibit the growth of the infectious agent can be an important goal.

In the studies of metabolic processes, differentiation, activation, and the like, there are many situations where it is desirable to be able to selectively increase or decrease the transcription of a particular gene. In this way, one can study the effect of a modulation in the transcription of the gene and expression of the gene product on the phenotype of the cell. In the extensive efforts to understand embryonic and fetal development, to define segmental polarity genes and their function, there is also interest in being able to selectively inhibit particular genes during various phases of the development of the fetus.

As in the case of the studies in culture, selective inhibition of particular genes can also be of interest in vivo. In many situations, cellular proliferation can be injurious to the host. The proliferation can be as a result of neoplasia, inflammation, or other process where increased number of cells has an adverse effect upon the health of the host.

There is, therefore, substantial interest in finding techniques and reagents which allow for selective modulation of particular genes, families of genes, and their associated regulatory sequences, so as to control intracellular molecular processes. Thus it is an object of the invention to provide novel compositions of nucleoprotein filaments that can be used in methods of regulating gene expression in a sequence specific manner. These methods and compositions also have applications in gene isolation, labelling, mutagenesis, modification, and in vitro manipulation of nucleic acids.

SUMMARY OF THE INVENTION

In accordance with the objects outlined above, the present invention provides nucleic acid compositions comprising anchoring or locking sequences and methods of use.

In one aspect the invention provides compositions comprising one recombinase and two substantially complementary single stranded targeting polynucleotides each containing at least one homology clamp that substantially corresponds to or is substantially complementary to a preselected target nucleic acid sequence and at least one anchoring sequences.

In another embodiment the invention provides a composition comprising a double D-loop comprising a target nucleic acid and two substantially complementary single stranded targeting polynucleotides, each containing at least one homology clamp that substantially corresponds to or is substantially complementary to a preselected target nucleic acid sequence and at least one anchoring sequence.

In yet another aspect the invention provides a composition comprising a double D-loop comprising a target nucleic acid and a single stranded targeting polynucleotide comprising a first homology clamp that substantially corresponds to a preselected target nucleic acid sequence, a second homology clamp that is substantially complementary to said preselected target nucleic acid sequence, and at least one anchoring sequence.

In a further aspect of the invention, the above compositions comprise a secondary probe that is substantially complementary to at least one of the anchoring sequences; a protein or chemical substituent. The chemical substituent is an intercalator, a cross-linking moiety, a label, a photoactive moiety, a nucleic acid scission moiety, a purification moiety, nucleic acid modification moiety. The anchoring sequences of the invention form B-DNA, A-DNA, Z-DNA, triplex or quadruplex structures In yet another aspect, the invention provides a composition comprising a double D-loop comprising a target nucleic acid and two substantially complementary single stranded targeting polynucleotides, each containing at least one homology clamp that substantially corresponds to or is substantially complementary to a preselected target nucleic acid sequence of said target nucleic acid, and at least one anchoring sequence, wherein the anchoring sequence for an anchoring structure; and bound to the anchoring structure is protein.

In a still further aspect, the invention provides cells comprising the above described compositions.

In other aspects, the invention provides methods of use of the compositions in modulating transcription or replication of a target sequence; methods of treating a disease state of a plant or animal; methods of detecting double-stranded nucleic acid target sequence; methods of isolating either strand of a double stranded target sequence; methods of isolating members of a gene family; methods of producing transgenic non-human organism or transgenic plants; methods of determining the function of a double stranded nucleic acid target sequence; methods of inhibiting double stranded nucleic acid rotation or branch migration.

BRIEF DESCRIPTION OF THE DRAWINGS

FIG. 1 depicts the applications of locked double D-loop DNA hybrids.

FIGS. 2A–F depict examples of double D-loop structures. Blank squares depict non-Watson-Crick base pairing. Filled in squares depict Watson-Crick base pairing. FIG. 2A depicts a double D-loop without an internal anchoring sequence. FIG. 2B depicts a duplex forming heterologous insert through Watson-Crick base pairing. FIG. 2C depicts a triplex-forming heterologous insert which is also a locking sequence that prevents DNA rotation. FIG. 2D depicts a quadruplex forming heterologous insert which is also a locking sequence that prevents DNA rotation. FIG. 2E depicts a heterologous insert which forms a triplex with a secondary probe, thereby forming a locking sequence that prevents DNA rotation. FIG. 2F depicts a double D-loop in which the internal homology clamp or anchoring sequence is formed from the target sequences, i.e. wherein the targeting polynucleotides are shorter than the target sequence.

FIG. 3 depicts one embodiment of gene modulation by locked double D-loops, blocking of copying of a target nucleic acid by self-anchored double D-loops. From top to bottom: intact target; target with double D-loop anchored by triplex; target with double D-loop anchored by quadruplex. Filled and open square symbolize Watson-Crick and Hoogsteen interactions, respectively; thin lines depict guanine tetrads. In this embodiment, self-anchored double D-loops ares shown downstream of the start of copying (promoter or origin of replication), but also can overlap or include the start of copying. Copying is inhibited by decreasing polymerase activity (hybrid arrest).

FIG. 4 depicts applications of locked double D-loops for mutagenesis and enhanced homologous recombination (EHR). Arrows point to single strand-double strand junctions as sites for recognition by repair enzymes, recombination enzymes, and recognition junctions that can be clipped by junction-specific nucleases.

FIG. 5 depicts inverse stringency gene cloning in which probes with mismatches relative to the targeted nucleic acid sequence are more stable than completely matched probes because heterologous sequences comprise anchoring sequences.

FIG. 6 shows the increased stability of hybrids formed by quadruplex anchoring sequences in comparison to hybrids formed by completely homologous probes.

FIG. 7 shows the increased stability of hybrids formed by triplex anchoring sequences in comparison to hybrids formed by completely homologous probes.

FIG. 8A depicts strategy for isolation of probe-target hybrid. The big circle designates a tether, such as a solid surface, magnetic bead, a plate, carrier, label, or purification tag, such as biotin. Filled and open small squares designate Watson-Crick and Hoogsteen pairing respectively. The difference between the upper left (UL) and upper right (UR) structures is that in the UL the heterologous insert forms a Watson-Crick hairpin before binding the tethered oligonucleotide. In the structure in the lower left (LL) the binding of the tether containing two oligonucleotides anchors the hybrids by the same way as intereacting heterologous inserts. In the structure in the lower right (LR), the binding of the tetheroligonucleotide constrains probe displacement if the distance between the hairpins is one or more helical turns.

FIG. 8B depicts rapid gene cloning. The "b" represents a tether as described in FIG. 8A. Shaded circles represent RecA. Short vertical lines represent Watson-Crick base pairing.

FIG. 9A depicts pBluescript II SK (–) and DNA probe oligonucleotides $NI_W$ (SEQ ID NO:1) and $NI_C$ (SEQ ID NO:2) (No DNA Insert; W, Watson DNA strand; C, Crick DNA strand) that are completely homologous to a region of target plasmid pBluescript II SK(−) (nucleotide positions 667 to 728).

FIG. 9B depicts DNA probe oligonucleotides $ZI_W$ (SEQ ID NO:3) and $ZI_C$ (SEQ ID NO:4) (Z-DNA forming Insert), which differ from $NI_W$ and $NI_C$ by the addition of the heterologous insert sequences $(AC)_9A$ (SEQ ID NO:7) and $(TG)_9T$ (SEQ ID NO:8) (bold lettering), respectively, as shown by short arrows in FIG. 9A. "b": biotin.

FIG. 9C depicts DNA probe oligonucleotides $QI_W$ (SEQ ID NO:5) and $QI_C$ (SEQ ID NO:6) (Quadruple DNA-forming insert) contains the heterologous insert sequence $T_2G_4T_2G_4T_2$. (SEQ ID NO:9) "b": biotin.

FIG. 10 depicts the formation of double D-loop DNA hybrids. RecA protein coated complementary single-stranded (css) DNA probes (small circles symbolize RecA protein) hybridize with negatively supercoiled double-stranded DNA targets. Formation of the probe-target hybrids causes partial relaxation of negative superhelical stress in the target DNA. This is schematically shown by decreased number of plectonemic negative superturns in the target. The heterologous DNA inserted into the probe DNA strand is looped out from the probe-target duplex. Heterologous DNA inserts are completely coated with RecA protein, which can prevent them from interaction with each other before RecA is removed. Both single and double D-loops can be formed by this reaction. Both these hybrid structures survive deproteinization within supercoiled hybrids, but only double D-loops are stable after linearization of the deproteinized hybrid. After linearization, deproteinized single D-loop DNA hybrids rapidly dissociate producing single-stranded DNA probe and double-stranded DNA target. Dashed arrows indicate that both during and after deproteinization, single D-loop hybrids can be converted to double D-loop hybrids by RecA-independent hybridization between the displaced strand of a single D-loop and the free single-stranded DNA probe.

FIG. 12A shows double D-loop hybrid stability. ScaI-linearized probe-target hybrids were incubated at 65° C. for different times and the amounts of the hybrids remaining after incubation for various times was monitored by gel electrophoresis. The types of hybrids formed by different combinations of probe DNA strands are shown at the top; combinations of completely homologous probe strands (NI; No DNA Insert) and probe strands with Quadruplex-DNA forming Inserts (QI) are shown. The slowest dissociation of double-D-loop hybrids occurred when both strands contain quadruplex-forming DNA insert sequences (lanes 1–4).

FIG. 12B shows double D-loop hybrid stability. The protocol described in FIG. 4A was performed but with ZI (Z-DNA forming Insert) probes substituted for NI probes. The "matched" combinations (lanes 1–4 and 13–16) produce hybrids with increased kinetic stability compared to "mixed" combinations (lanes 5–8 and 9–13). This indicates that complex formation between heterologous inserts significantly contributes to double D-loop stabilization. In some cases, in addition to linearized hybrids, small amounts of uncut supercoiled (SC) hybrids remained. In contrast with linear hybrids, the amount of supercoiled hybrid did not change significantly during incubation at 65° C. This result is expected because supercoiled hybrids are much more stable. The minor DNA fraction shown by dashed arrow was not detectable by ethidium bromide staining and probably represents dimers.

FIG. 13 shows a comparison of the rates of dissociation of double D-loop hybrids. Apparent half-life time, $\tau_{1/2}$ is the time of incubation (minutes) in which 50% of the double D-loop hybrids dissociate. The longer the $\tau_{1/2}$ then the greater kinetic stability of the hybrids. The double D-loop hybrids formed by "matched" combination of probes $QI_W/QI_C$ and $ZI_W/ZI_C$ have increased kinetic stabilities in comparison with all the other hybrids. Small black squares designate Watson-Crick base pairing and thin lines designate pairing between guanines in quadruplex.

FIGS. 14A–F depicts double D-loop DNA hybrid dissociation pathway. FIG. 14A depicts a double D-loop DNA hybrid structure with complete pairing between the probe and the target DNA strands. FIG. 14B depicts probe-target DNA duplexes denaturing at the ends due to thermal fluctuations. FIG. 14C depicts nucleation of probe-probe duplex by Watson-Crick base pairing between the ends of the probe DNA strands resulting in formation of a DNA four-way junction. FIG. 14D depicts DNA four-way junction migrating randomly along the double D-loop hybrid until it occasionally reaches the right edge position, followed by irreversible dissociation of the double D-loop hybrid. FIG. 14F is a magnified view of FIG. 14D and depicts the direction of rotation of the DNA duplexes during four-way junction migration. When the four-way junction moves from the left to the right, the probe DNA strands (thick lines) and the target DNA strands (thin lines) spool from probe-target duplexes to probe-probe and target-target duplexes. FIG. 14E depicts the products of dissociation of the double D-loop hybrids are intact double-stranded target DNA and double-stranded probe DNA.

FIGS. 15A–B depicts the structures of double D-loop hybrids with interacting heterologous inserts. Base pairing is shown only within the complex between heterologous inserts. FIG. 15A depicts the heterologous inserts as Watson-Crick base pairs (designated by small black squares). FIG. 7B depicts the heterologous inserts as a quadruplex. Thin lines designate base pairing between guanines in the quadruplex.

FIG. 16 depicts the procedure for obtaining a triplex-forming probe. The triplex-forming insert was cloned into pBluescript II SK(−) to obtain pTL (SEQ ID NO:10; SEQ ID NO:11). Triplex-forming probes were obtained by PCR from pTL and targeted to parental pBluescript II SK(−). A control probe (i.e., completely homologous probe without triplex-forming sequence) was obtained as the PCR product using pBluescript II SK(−) as the template with the identical primers.

FIGS. 17A–C depicts dissociation of branched DNA structures. FIG. 17A: Irreversibly nucleated four-way DNA junction. The upper left flank of the structure (shown in gray) does not have homology with the bottom left flank of the structure. This makes four-way DNA junction migration through this flank not possible and consequently the four-way junction is always present within the structure, until complete dissociation (bottom). Within the model used in this study, each step of four-way junction migration (symbolized by the solid arrow) has the same time $\tau_1$. FIG. 17B: Y-like DNA structure. In contrast to FIG. 17A, within Y-like DNA structures the four-way DNA junction formation is reversible and proceeds via energetically unfavorable openings of several base pairs ("transition" structure in square brackets). Consequently, the first step of branch migration (symbolized by the dashed arrow) is characterized by the nucleation time $\tau_n$ which is much longer than $\tau_1$. FIG. 17C: Migration of the four-way DNA junction through mismatched base pairs (which symbolized by the open squares). The probability of a step which leads to replacement of mismatched base pairs by the matched base pairs is larger, which is symbolized by the longer arrow.

FIGS. 18A–D depicts double D-loop DNA structures. Longer DNA strands are the "target strands" and the shorter DNA strands as the "probe strands". These designations are commonly used in gene targeting applications (Pati et al. in Molecular Biology of Cancer, ed. J. Bertino (Academic Press, San Diego) Volume III, 1601–1625. FIG. 18A: The non-disturbed "zero" state without nucleation of the probe-probe duplex. FIG. 18B: Single-nucleated (sn) state which is formed in a similar way as shown for Y-like DNA structure in FIG. 17B. FIG. 18C: Double-nucleated (dn) state. The topological scheme of the double-nucleated state is shown below the standard scheme of this structure. It is seen that target-target (T:T) and probe-probe (P:P) duplexes serve as "locks" which prevent changes in the number of helical turns within probe-target (PT) duplexes. FIG. 18D: Irreversible nucleation of the probe-probe DNA provided by heterology between the probe and the target DNAs.

FIGS. 19A–B show dissociation times of double D-loops with and without a slow reversible initiation step. FIG. 19A: Length dependences of dissociation times of double D-loops are plotted in double-logarithmic coordinates. Curve "R" corresponds to usual double D-loops with a slow reversible initiation step (Eq. 22a) for $\phi=2$ and $1/\nu=10^4$. Curve "I" corresponds to double D-loops with the irreversible nucleation of the four-way DNA junction at one end (Eq.46) for the same values of $\phi$ and $\nu$. The curves intersect in the vicinity of $\log_{10}L \approx \log_{10}(1/\nu)=4$. FIG. 19B: "Apparent exponents" of the curves from FIG. 19A. For curve "R", this exponent changes from 1 to 2 in the vicinity of $\log_{10}L \approx \log_{10}(1/\nu)=4$, which corresponds to switching from linear dependence to quadratic dependence. For curve "I" this exponent is always close to 2, which corresponds to quadratic dependence.

FIG. 20 depicts intercalator-stablized double D-loops.

DETAILED DESCRIPTION OF THE INVENTION

Figure 11:
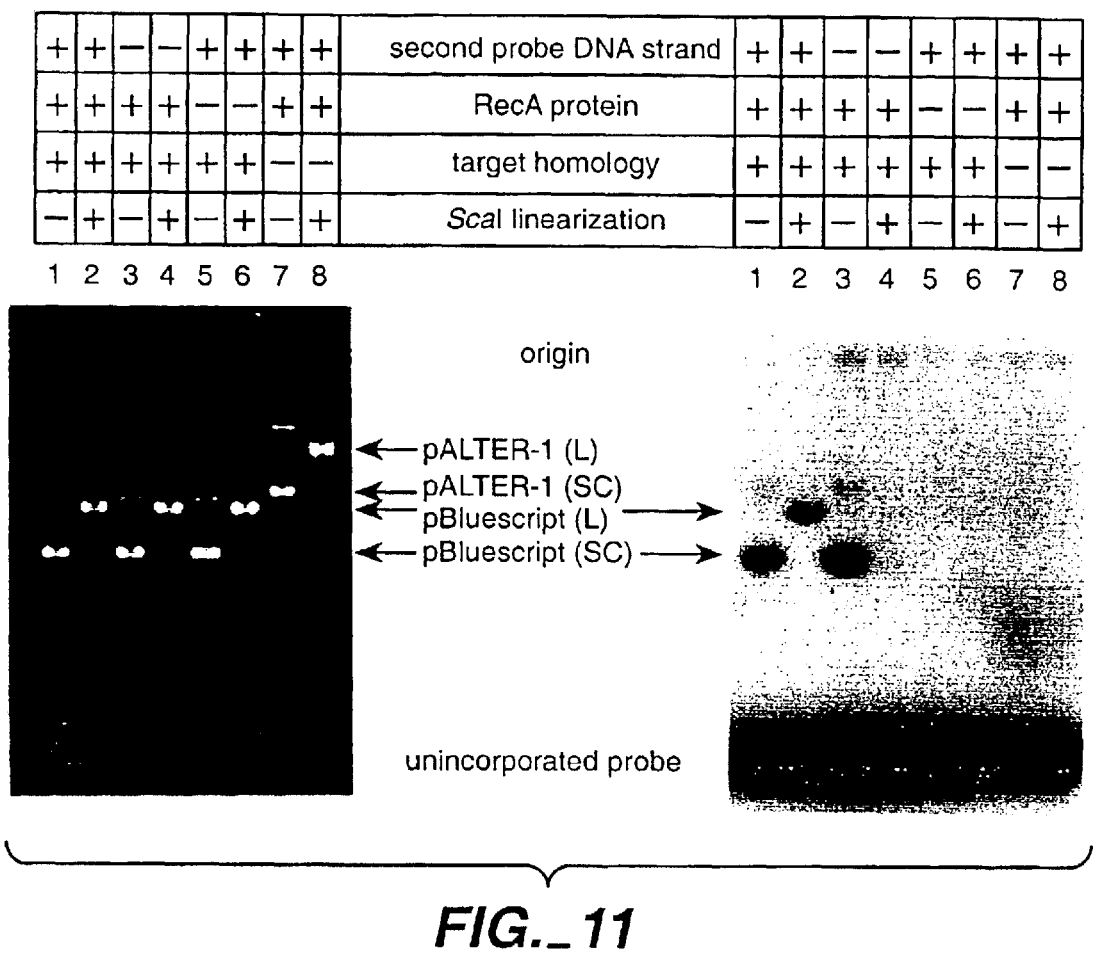
FIG. 11 demonstrates that both complementary DNA probe strands are required to stabilize probe-target hybrids after linearization. Two complementary single-stranded DNA probes were targeted to the homologous region of pBluescript II SK(−) plasmid as described in Example 1. As controls for specificity, pALTER-1 (Promega), which does not contain homology with the DNA probes, was used. After the targeting reaction and deproteinization, each sample was separated into two equal parts. To one part ScaI restriction enzyme was added (designated as ScaI linearization+) and restriction was performed for 2 hours at 37–38° C. Designations of fractions on the gel are follows: SC, supercoiled DNA; L, linear DNA. The left panel is a photograph of the gel stained with ethidium bromide and the right panel is an autoradiograph of the same gel. The minor slower migrating DNA bands seen in the photograph in lanes with supercoiled target DNAs are open circular and supercoiled dimers of the target plasmids. Only in the presence of both DNA probe strands (right panel, lane 2) do probe-target hybrids survive linearization.

The present invention is directed to the use of novel compositions which can be used to essentially "anchor" or "lock" an endogenous nucleic acid into a particular structure. This locked structure can then regulate gene expression (i.e. inhibit or enhance transcription or replication), or can be used as a stable structure that can be used to label or otherwise modify the endogenous nucleic acid sequence, or can be used to isolate the endogenous sequence, i.e. for cloning.

These novel compositions are structurally based on D-loops as described in U.S. application Ser. Nos. 08/381,634. now abandoned; 08/882,756, now U.S. Pat. No. 5,929,043; 09/301,153, now U.S. Pat. No. 6,245,565; 08/781,329, now U.S. Pat. No. 5,989,879; 09/288,586. now U.S. Pat. No. 6,200,812; 09/209,676, now U.S. Pat. No. 6,524,856; 09/007,020, now U.S. Pat. No. 6,090,539; 09/179,916, now U.S. Pat. No. 6,391,564; 09/182,102. published as U.S. 2003-0143533 A1, now abandoned; 09/182,097; 09/181,027, published as U.S. 2003-0208053 A1, now abandoned; 09/260,624, published as U.S. 2002-0137698 A1, pending; 09/373,347, abandoned; 09/306,749, pending; 60/153,795, expired; and international application nos. PCT/US97/19324; PCT/US98/26498; PCT/US98/01825, U.S. Pat. No. 5,763,240, U.S. Pat. No. 5,731,411, U.S. Pat. No. 5,510,473; U.S. Pat. No. 5,948,653; U.S. Pat. No. 4,888,274, U.S. Pat. No. 5,510,473, U.S. Pat. No. 5,460,941, all of which are expressly incorporated by reference in their entireties. In general, as depicted in FIG. 2A, double D-loops are comprised of the double stranded target sequence which is separated by the incoming pair of substantially complementary targeting polynucleotides, to form two new double stranded sequences. Previous work has utilized "internal homology clamps", as depicted in FIGS. 2B and 2F, which stabilize the double D-loop structure. However, upon deproteinization of these double D-loop structures, without additional components, the double D-loop structures are not necessarily stable, and may not result in modulation of copying through the double D-loop. Since most copying enzymes can unwind Watson-Crick duplexes, the strand of the probe which is paired with the template strand of the target will be displaced in the course of the copying. The other probe, which remains in a complex with the displaced non-template strand of the target may not have any effect on copying, due to its remote location from the copying enzyme.

Accordingly, the present invention provides novel double D-loop forming structures, that contain additional components in the form of "anchoring" or "locking" sequences, that serve to keep the two heteroduplexes in close contact via strong interactions. In this case the heteroduplex formed with the non-template strand will constrain the rotation of the copying enzyme around the template, impeding and/or blocking the copying in a manner similar to the blockage of transcription by other higher-order structures (see Grabczyk et al., J. Biol. Chem. 270:1791 (1995)).

Thus, the anchoring sequences serve to prevent disassociation of the novel structure, and thus can not only prevent copying but will also enable labeling, modification, and/or cloning of the endogeneous sequence. In an alternative embodiment, the novel structure will increase or enhance copying. The kinetics of interaction of the anchoring sequences will be much more efficient within the double D-loop as compared to unbound probe strands in solution. In addition, chemical substituents, for example cross-linking agents, may be used to add further stability or irreversibility to the reaction.

Thus, the present invention provides compositions comprising at least one recombinase and two substantially complementary single stranded targeting polynucleotides. By "recombinase" herein is meant proteins that, when included with an exogenous targeting polynucleotide, provide a measurable increase in the recombination frequency and/or localization frequency between the targeting polynucleotide and an endogenous predetermined DNA sequence. Thus, in a preferred embodiment, increases in recombination frequency from the normal range of $10^{-8}$ to $10^{-4}$, to $10^{-4}$ to $10^1$, preferably $10^{-3}$ to $10^1$, and most preferably $10^{-2}$ to $10^1$, may be acheived.

In the present invention, recombinase refers to a family of RecA-like recombination proteins all having essentially all or most of the same functions, particularly: (i) the recombinase protein's ability to properly bind to and position targeting polynucleotides on their homologous targets and (ii) the ability of recombinase protein/targeting polynucleotide complexes to efficiently find and bind to complementary endogenous sequences. The best characterized RecA protein is from E. coli, in addition to the wild-type protein a number of mutant RecA-like proteins have been identified (e.g., RecA803; see Madiraju et al., PNAS USA 85(18):6592 (1988); Madiraju et al., Biochem. 31:10529 (1992); Lavery et al., J. Biol. Chem. 267:20648 (1992)). Further, many organisms have RecA-like recombinases with strand-transfer activities (e.g., Fugisawa et al., (1985) Nucl. Acids Res. 13: 7473; Hsieh et al., (1986) Cell 44: 885; Hsieh et al., (1989) J. Biol. Chem. 264: 5089; Fishel et al., (1988) Proc. Natl. Acad. Sci. (USA) 85: 3683; Cassuto et al., (1987) Mol. Gen. Genet. 208: 10; Ganea et al., (1987) Mol. Cell Biol. 7: 3124; Moore et al., (1990) J. Biol. Chem. 19: 11108; Keene et al., (1984) Nucl. Acids Res. 12: 3057; Kimeic, (1984) Cold Spring Harbor Svmp. 48: 675; Kmeic, (1986) Cell 44: 545; Kolodner et al., (1987) Proc. Natl. Acad. Sci. USA 84: 5560; Sugino et al., (1985) Proc. Natl. Acad. Sci. USA 85: 3683; Halbrook et al., (1989) J. Biol. Chem. 264: 21403; Eisen et al., (1988) Proc. Natl. Acad. Sci. USA 85: 7481; McCarthy et al., (1988) Proc. Natl. Acad. Sci. USA 85: 5854; Lowenhaupt et al., (1989) J. Biol. Chem. 264: 20568, which are incorporated herein by reference). Examples of such recombinase proteins include, for example but are not limited to: RecA, RecA803, uvsX, and other RecA mutants and RecA-like recombinases (Roca, A. I. (1990) Crit. Rev. Biochem. Molec. Biol. 25: 415), sep1 (Kolodner et al., (1987) Proc. Natl. Acad. Sci. (U.S.A.) 84:5560; Tishkoff et al. Molec. Cell. Biol. 11:2593), RuvC (Dunderdale et al., (1991) Nature 354: 506), DST2, KEM1, XRN1 (Dykstra et al., (1991) Molec. Cell. Biol. 11:2583), STPα/DST1 (Clark et al., (1991) Molec. Cell. Biol. 11:2576), HPP-1 (Moore et al., (1991) Proc. Natl. Acad. Sci. (U.S.A.) 88:9067), other target recombinases (Bishop et al., (1992) Cell 69: 439; Shinohara et al., (1992) Cell 69: 457); incorporated herein by reference. RecA may be purified from E coli strains, such as E. coli strains JC12772 and JC15369 (available from A. J. Clark and M. Madiraju, University of California-Berkeley, or purchased commercially). These strains contain the RecA coding sequences on a "runaway" replicating plasmid vector present at a high copy number per cell. The RecA803 protein is a high-activity mutant of wild-type RecA. The art teaches several examples of recombinase proteins, for example, from Drosophila, yeast, plant, human, and non-human mammalian cells, including proteins with biological properties similar to RecA (i.e., RecA-like recombinases), such as Rad51 from mammals and yeast, and Pk-rec (see Rashid et al., Nucleic Acid Res. 25(4):719 (1997), hereby incorporated by reference). In addition, the recombinase may actually be a complex of proteins, i.e. a "recombinosome". In addition, included within the definition of a recombinase are portions or fragments of recombinases which retain recombinase biological activity, as well as variants or mutants of wild-type recombinases which retain biological activity, such as the E. coli RecA803 mutant with enhanced recombinase activity.

The crystal structure of RecA protein in the absence of DNA reveals two disordered polypeptide loops, L1 and L2, that are proposed nucleic acid binding sites (Story et al, Nature 355(6358):318–325 (1992)). Several lines of evidence indicate that loop L2 is the oligonucleotide binding domain: a) proteolysis of ssDNA-RecA complexes yields a unique 4-kD peptide protected by the DNA that spans this loop (Gardner et al., Eur J. Biochem. 233:419–425 (1995)); b) crosslinks between a ssDNA and RecA map to loops L1 and L2; c) the intrinsic fluoresescence of peptides in loop2 is quenched in RecA-DNA complexes; and d) the 20 amino acid FECO peptide corresponding to the L2 polypeptide loop (NQIRMKIGVMFGNPETTTGG) (SEQ ID NO:12) binds to ssDNA.

Recently, it was shown that this 20 amino acid FECO peptide from the L2 DNA binding region of RecA peptide is capable of both binding to ssDNA and finding its homologous site in the duplex DNA (Voloshin et al., Science 272:868–872 (1996)). A phenylalanine in the FECO peptide, corresponding to position 203 in the whole RecA protein, is the most conserved residue in the region (corresponding to L2 positions 195–209) among prokaryotic RecA's and their eukaryotic homologues, such as the DMC1 and Rad51 proteins (Story et al., 1992). An aromatic amino acid in position 203 is important for binding to the DNA. These aromatic amino acid containing peptides not only bind to ssDNA but also unstack it. RecA extends both ssDNA and dsDNA by 50%, and the unstacking of ssDNA is proposed to be essential for RecA to facilitate the three stranded interactions between ssDNA and dsDNA. Unstacked DNA bases are more accessible to modification by potassium permanganate (PP), which attacks thymines in a direction perpendicular to the base plane. Single strand DNA oligonucleotides are much more reactive to P:P in complexes with RecA. DNA bound to the FECO peptide changed the reactivity of thymines in ssDNA in a similar fashion. Moreover, the conformation of the FECO peptide changed upon binding to ssDNA. Binding of FECO peptide to ssDNA induced a conformational transition in the polypeptide from a random coil to a predominantly β structure. Most importantly, 53-mer oligonucleotides coated with FECO peptide targeted only homologous sites in DNA and formed hybrid molecules (D-loops) very similar to those formed by RecA protein. Hybrid molecule formation was about 20% of that of RecA protein. As with RecA protein, no hybrid molecules were observed when ssDNA was replaced with a duplex of the same sequence or when a target plasmid was used without significant homology to the ssDNA. The formation of hybrids was not dependent on the sequence targeted.

Short oligopeptide fragments (20 amino acids, FECO peptide) bound to short oligonucleotide sequences can catalyze D-loop formation. These complexes may be as small as 5000 kilodaltons and may be used like gene drugs for specific targeting. Specific peptides which bind to DNA at single sites have been successful at blocking transcription in vivo (Choo et al., Nature 372:642 (1994)). These complexes are amenable for in vivo delivery because of their relatively small size, non-toxicity, and ease of delivery and uptake.

Accordingly, in one embodiment, FECO oligopeptide (NQIRMKIGXTMFGNPETTTGG) (SEQ ID NO:12) and NLS-FECO (PLLLALVNQIIRMKIGVMFGNPETTTGG) (SEQ ID NO:13) are used to for specific gene targeting and by locked D-loop hybrids. E. coli RecA protein does not contain a eukaryotic cell nuclear localization signal (NLS) facilitating the transport of exogenously added proteins to the nucleus. Certain oligopeptides and proteins that do not have the NLS signal are not actively transported into the nucleus. For example, it has been shown by immunofluorescence staining that when wild type RecA protein is microinjected into the cytoplasm of certain human cells, it remains in the cytoplasm and it does not significantly enter the nucleus (Kido et al., Exp. Cell Res. 198:107–114 (1992)). In eukaryotic cells, nuclear proteins are initially synthesized in the cytoplasm and then are rapidly transported into the nucleus. The precise mechanism of nuclear transport is not fully known, and active transport has been suggested (Yamaizumi et al., Nature 273:782–784 (1978); Sugawa et al., Exp. cell Res. 159:419–429 (1985)); Tsuneoka et al., J. Biol. Chem. 261:1829–1834 (1986); Imamoto-Sonobe et al., Proc. Natl. Acad. Sci. USA 85:3426–3430 (1988)). Kalderon et al., Nature 311:5981 (1984a); Kalderon et al. Cell 3:499–509 (1984b)). Kalderon et al., (1984a, b), showed that a short oligopeptide sequence of the SV40 virus large T-antigen, PLLLALV (SEQ ID NO:14), specifies a nuclear localization signal (NLS) (Kalderon et al., 1984a and 1984b). Fusion of exogenous proteins with this viral NLS peptide has also been shown to direct the transport of fused exogenous proteins into the nucleus. For example, when this viral NLS peptide was fused to the RecA protein and injected into the cytoplasm, the PLLLALV (SEQ ID NO:14) modified RecA protein was efficiently transported to the nucleus (Kido et al., 1992). More importantly, the NLS fused RecA protein retains its full in vivo RecA activity.

Reiss et al., (Proc. Natl. Acad. Sci. USA 93:3094–3098 (1996)), have demonstrated that *E.coli* RecA protein also interacts with genomic homologous DNA in somatic plant cells. Cells expressing a NLS fusion peptide with RecA protein were at least three times as efficient as wild type cells in repairing DNA damage. Moreover, homologous recombination at a defined locus carrying an endogenous nuclear marker gene was stimulated at least 10 fold in cells expressing nuclear targeted RecA. What is also striking is the fact that nuclear targeted RecA protein was consistently more effective than the wild type RecA protein in these experiments stimulating homolgous targeting and recombination. Further experiments by Reiss et al., Mol. Gen. Gen. 253:695–702 (1997), showed that the modified RecA fusion protein containing a NLS at its N-terminal end was nearly identical to the wild type protein in terms of its in vitro biochemical activities. This NLS oligopeptide fused to RecA protein bound ssDNA with the same stoichiometry as unmodified RecA and promoted the exchange of homologous DNA strands with similar kinetics compared to the wild type RecA protein. These measurements show that the addition of NLS oligopeptides does not significantly interfere with essential biochemical properties of the recombinase protein.

In a preferred embodiment, the 20 amino acid FECO peptide (NQIIRMXIGVMIFGNPETTTGG) (SEQ ID NO:12) and FECO with a NLS (PLLLALVNQIRMKIGVMIFGNPETTTGG) (SEQ ID NO:13) attached to the N-terminal end are used for cssDNA targeting to a homology clamped site in the duplex DNA.

In a preferred embodiment, RecA or rad51 is used. For example, RecA protein is typically obtained from bacterial strains that overproduce the protein: wild-type *E coli* RecA protein and mutant RecA803 protein may be purified from such strains. Alternatively, RecA protein can also be purchased from, for example, Pharmacia (Piscataway, N.J.).

RecA proteins, and its homologs, form a nucleoprotein filament when it coats a single-stranded DNA. In this nucleoprotein filament, one monomer of RecA protein is bound to about 3 nucleotides. This property of RecA to coat single-stranded DNA is essentially sequence independent, although particular sequences favor initial loading of RecA onto a polynucleotide (e.g., nucleation sequences). The nucleoprotein filament(s) can be formed on essentially any DNA molecule and can be formed in cells (e.g., mammalian cells), forming complexes with both single-stranded and double-stranded DNA, although the loading conditions for dsDNA are somewhat different than for ssDNA.

The compositions further comprise at least one, and preferably two, single stranded targeting nucleic acids, generally referred to herein as targeting polynucleotides or targeting probes. By "nucleic acid", "oligonucleotide", and "polynucleotide" or grammatical equivalents herein is meant at least two nucleotides covalently linked together. A nucleic acid of the present invention will generally contain phosphodiester bonds, although in some cases nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al., Chem. Lett. 805 (1984), Letsinger et al., J. Am. Chem. Soc. 110:4470 (1988); and Pauwels et al., Chemica Scripta 26:141 (1986)), phosphorothioate, phosphorodithioate, O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). These modifications of the ribose-phosphate backbone or bases may be done to facilitate the addition of other moieties such as chemical constituents, including 2' O-methyl and 5' modified substituents, as discussed below, or to increase the stability and half-life of such molecules in physiological environments. In a preferred embodiment, a nucleic acid is a protein-nucleic acid (PNA).

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo-and ribo-nucleotides, and any combination of bases, including uracil, adenine, thymine, cytosine, guanine, inosine, xathanine and hypoxathanine, etc. Thus, for example, chimeric DNA-RNA molecules may be used such as described in Cole-Strauss et al., Science 273:1386 (1996) and Yoon et al., PNAS USA 93:2071 (1996), both of which are hereby incorporated by reference. Additionally, the trageting nucleic acids are circular or linear.

In general, the targeting polynucleotides may comprise any number of structures, as long as the changes do not substantially effect the functional ability of the targeting polynucleotide to result in homologous recombination. For example, recombinase coating of alternate structures should still be able to occur.

Targeting polynucleotides may be produced by any number of different methods, as will be appreciated by those in the art, including, but not limited to, chemical synthesis of oligonucleotides, nick-translation of a double-stranded DNA template, polymerase chain-reaction amplification of a sequence (or ligase chain reaction amplification), purification of prokaryotic or target cloning vectors harboring a sequence of interest (e.g., a cloned cDNA or genomic clone, or portion thereof) such as plasmids, phagemids, YACs, cosmids, bacteriophage DNA, other viral DNA or replication intermediates, or purified restriction fragments thereof, as well as other sources of single and double-stranded polynucleotides having a desired nucleotide sequence. Targeting polynucleotides are generally ssDNA or dsDNA, most preferably two complementary single-stranded DNAs as is more fully outlined below.

Targeting polynucleotides are generally at least about 2 to 100 nucleotides long, preferably at least about 5- to 100 nucleotides long. In one embodiment targeting polynucleotides are at least about 250 to 500 nucleotides long, more preferably at least about 500 to 2000 nucleotides long, or longer; however, as the length of a targeting polynucleotide increases beyond about 20,000 to 50,000 to 400,000 nucleotides, the efficiency or transferring an intact targeting polynucleotide into the cell decreases. The length of homology may be selected at the discretion of the practitioner on the basis of the sequence composition and complexity of the predetermined endogenous target DNA sequence(s) and guidance provided in the art, which generally indicates that 1.3 to 6.8 kilobase segments of homology are preferred (Hasty et al., (1991) Molec. Cell. Biol. 11: 5586; Shulman et al., (1990) Molec. Cell. Biol. 10: 4466, which are incorporated herein by reference).

Targeting polynucleotides have a number of relevant structures. In a preferred embodiment, the target polynucleotides comprise homology clamps, i.e. sequences that substantially correspond to, or are substantially complementary to, a predetermined endogenous DNA sequence. The term "corresponds to" is used herein to mean that a polynucleotide sequence is homologous (i.e., may be similar or identical, not strictly evolutionarily related) to all or a portion of a reference polynucleotide sequence, or that a polynucleotide sequence is identical to a reference polynucleotide sequence. In contradistinction, the term "complementary to" is used herein to mean that the complementary sequence is homologous to all or a portion of a reference polynucleotide sequence. As outlined below, preferably, the homology is at least 70%, preferably 85%, and more preferably 95% identical. Thus, the complementarity between two single-stranded targeting polynucleotides need not be perfect. For illustration, the nucleotide sequence "TATAC" (SEQ ID NO:15) corresponds to or is identical to a reference sequence "TATAC" (SEQ ID NO:15) and is perfectly complementary to a reference sequence "GTATA" (SEQ ID NO:16).

The terms "substantially corresponds to" or "substantial identity" or "homologous" as used herein denotes a characteristic of a nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. "Substantially complementary" as used herein refers to a sequence that is complementary to a sequence that substantially corresponds to a reference sequence. In general, targeting efficiency increases with the length of the targeting polynucleotide portion that is substantially complementary to a reference sequence present in the target DNA.

A preferred method of determining nucleic acid sequence identity utilizes the BLASTN module of WU-BLAST-2 set to the default parameters, with overlap span and overlap fraction set to 1 and 0.125, respectively.

The alignment may include the introduction of gaps in the sequences to be aligned. It is understood that in one embodiment, the percentage of sequence identity will be determined based on the number of identical nucleic acid residues in relation to the total number of residues.

In one embodiment, only identities are scored positively (assigned a value of +1) and all forms of sequence variation including gaps are assigned a value of "0". Percent sequence identity can be calculated, for example, by dividing the number of matching identical residues by the total number of residues of the "shorter" sequence in the aligned region and multiplying by 100. The "longer" sequence is the one having the most actual residues in the aligned region.

"Specific hybridization" is defined herein as the formation of hybrids between a targeting polynucleotide (e.g., a polynucleotide of the invention which may include substitutions, deletions, and/or additions as compared to the predetermined target DNA sequence) and a predetermined target DNA, wherein the targeting polynucleotide preferentially hybridizes to the predetermined target DNA such that, for example, at least one discrete band can be identified on a Southern blot of DNA prepared from target cells that contain the target DNA sequence, and/or a targeting polynucleotide in an intact nucleus localizes to a discrete chromosomal location characteristic of a unique or repetitive sequence. In some instances, a target sequence may be present in more than one target polynucleotide species (e.g., a particular target sequence may occur in multiple members of a gene family or in a known repetitive sequence). It is evident that optimal hybridization conditions will vary depending upon the sequence composition and length(s) of the targeting polynucleotide(s) and target(s), and the experimental method selected by the practitioner. Various guidelines may be used to select appropriate hybridization conditions (see, Maniatis et al., Molecular Cloning: A Laboratory Manual (1989), 2nd Ed., Cold Spring Harbor, N.Y. and Berger and Kimmel, Methods in Enzymology, Volume 152, Guide to Molecular Cloning Techniques (1987), Academic Press, Inc., San Diego, Calif., which are incorporated herein by reference). Methods of hybridizing a targeting polynucleotide to a discrete chromosomal location in intact nuclei are provided herein in the Detailed Description.

As used herein, the terms "predetermined endogenous DNA sequence" and "predetermined target sequence" refer to polynucleotide sequences contained in a target cell. Accordingly, such sequences include, for example, chromosomal sequences (e.g., structural genes, regulatory sequences including promoters and enhancers, recombinatorial hotspots, repeat sequences, integrated proviral sequences, hairpins, palindromes, a nucleic acid motif, or a nucleic acid the encodes an amino acid motif, and episomal or extrachromosomal sequences (e.g., replicable plasmids or viral replication intermediates) including chloroplast, mitochondrial, viral or myoplasmal nucleic acid sequences. By "predetermined" or "pre-selected" it is meant that the target sequence may be selected at the discretion of the practitioner on the basis of known or predicted sequence information, and is not constrained to specific sites recognized by certain site-specific recombinases (e.g., FLP recombinase or CRE recombinase). In one embodiment, the predetermined target sequence is a consensus sequence, such as a homology motif tag, which is used to target genes or related gene families. In some embodiments, the predetermined endogenous DNA target sequence will be other than a naturally occurring germline DNA sequence (e.g., a transgene, parasite, mycoplasmal or viral sequence). An exogenous polynucleotide is a polynucleotide which is transferred into a target cell but which has not been replicated in that host cell; for example, a virus genome polynucleotide that enters a cell by fusion of a virion to the cell is an exogenous polynucleotide, however, replicated copies of the viral polynucleotide subsequently made in the infected cell are endogenous sequences (and may, for example, become integrated into a cell chromosome). Similarly, transgenes which are microinjected or transfected into a cell are exogenous polynucleotides, however integrated and replicated copies of the transgene(s) are endogenous sequences.

The homology clamp sequences serve as templates for homologous pairing with the predetermined endogenous sequence(s). In targeting polynucleotides, such homology clamps are typically located at or near the 5' or 3' end, preferably homology clamps are internally located or located at each end of the polynucleotide (Berinstein et al., (1992) Molec, Cell. Biol. 12: 360, which is incorporated herein by reference). Without wishing to be bound by any particular theory, it is believed that the addition of recombinases permits efficient gene targeting with targeting polynucleotides having short (i.e., about 50 to 1000 basepair long) segments of homology, as well as with targeting polynucleotides having longer segments of homology.

Therefore, it is preferred that targeting polynucleotides of the invention have homology clamps that are highly homologous to the predetermined target endogenous DNA sequence(s), most preferably isogenic. Typically, targeting polynucleotides of the invention have at least one homology clamp that is at least about 18 to 35 nucleotides long, and it is preferable that homology clamps are at least about 20 to 100 nucleotides long, and more preferably at least about 100–500 nucleotides long, although the degree of sequence homology between the homology clamp and the targeted sequence and the base composition of the targeted sequence will determine the optimal and minimal clamp lengths (e.g., G-C rich sequences are typically more thermodynamically stable and will generally require shorter clamp length). Therefore, both homology clamp length and the degree of sequence homology can only be determined with reference to a particular predetermined sequence, but homology clamps generally must be at least about 12 nucleotides long and must also substantially correspond or be substantially complementary to a predetermined target sequence. Preferably, a homology clamp is at least about 12, and preferably at least about 50 nucleotides long and is identical to or complementary to a predetermined target sequence.

The formation of heteroduplex joints is not a stringent process; genetic evidence supports the view that the classical phenomena of meiotic gene conversion and aberrant meiotic segregation result in part from the inclusion of mismatched base pairs in heteroduplex joints, and the subsequent correction of some of these mismatched base pairs before replication. Observations of RecA protein have provided information on parameters that affect the discrimination of relatedness from perfect or near-perfect homology and that affect the inclusion of mismatched base pairs in heteroduplex joints. The ability of RecA protein to drive strand exchange past all single base-pair mismatches and to form extensively mismatched joints in superhelical DNA reflect its role in recombination and gene conversion. This errorprone process may also be related to its role in mutagenesis. RecA-mediated pairing reactions involving DNA of φX174 and G4, which are about 70 percent homologous, have yielded homologous recombinants (Cunningham et al., (1981) Cell 24: 213), although RecA preferentially forms homologous joints between highly homologous sequences, and is implicated as mediating a homology search process between an invading DNA strand and a recipient DNA strand, producing relatively stable heteroduplexes at regions of high homology.

In a preferred embodiment, two substantially complementary targeting polynucleotides are used. In one embodiment, the targeting polynucleotides form a double stranded hybrid, which may be coated with recombinase, although when the recombinase is RecA, the loading conditions may be somewhat different from those used for single stranded nucleic acids.

In a prefered embodiment, two substantially complementary single-stranded targeting polynucleotides are used. The two complementary single-stranded targeting polynucleotides are usually of equal length, although this is not required. However, as noted below, the stability of the four strand hybrids of the invention is putatively related, in part, to the lack of significant unhybridized single-stranded nucleic acid, and thus significant unpaired sequences are not preferred. Furthermore, as noted above, the complementarity between the two targeting polynucleotides need not be perfect; that is, the targeting polynucleotides can be the same or different.

There appears to be a fundamental difference in the stability of RecA-protein-mediated D-loops formed between one single-stranded DNA (ssDNA) probe hybridized to negatively supercoiled DNA targets in comparison to relaxed or linear duplex DNA targets. Internally located dsDNA target sequences on relaxed linear DNA targets hybridized by one ssDNA probe produces single D-loops, which are unstable after removal of RecA protein (Adzuma, Genes Devel. 6:1679 (1992); Hsieh et al., PNAS USA 89:6492 (1992); Chiu et al., Biochemistry 32:13146 (1993)). This probe DNA instability of hybrids formed with linear duplex DNA targets is most probably due to the incoming ssDNA probe W-C base pairing with the complementary DNA strand of the duplex target and disrupting the base pairing in the other DNA strand. The required high freeenergy of maintaining a disrupted DNA strand in an unpaired ssDNA conformation in a protein-free single-Dloop apparently can only be compensated either by the stored free energy inherent in negatively supercoiled DNA targets or by base pairing initiated at the distal ends of the joint DNA molecule, which is hybrid comprising the probe and the target nucleic acids, allowing the exchanged strands to freely intertwine.

However, the addition of a second complementary ssDNA to the three-strand-containing single-D-loop stabilizes the deproteinized hybrid joint molecules by allowing W-C base pairing of the probe with the displaced target DNA strand. The addition of a second RecA-coated complementary ssDNA (cssDNA) strand to the three-strand containing single D-loop stabilizes deproteinized hybrid joints located away from the free ends of the duplex target DNA (Sena & Zarling, Nature Genetics 3:365 (1993); Revet et al. J. Mol. Biol. 232:779 (1993); Jayasena and Johnston, J. Mol. Bio. 230:1015 (1993)). The resulting four-stranded structure, named a double D-loop by analogy with the three-stranded single D-loop hybrid has been shown to be stable in the absence of RecA protein. This stability likely occurs because the restoration of W-C basepairing in the parental duplex would require disruption of two W-C base pairs in the double D-loop (one W-C pair in each heteroduplex D-loop). Since each base-pairing in the reverse transition (double D-loop to duplex) is less favorable by the energy of one W-C basepair, the pair of cssDNA probes are thus kinetically trapped in duplex DNA targets in stable hybrid structures. The stability of the double D loop joint molecule within internally located probe:target hybrids is an intermediate stage prior to the progression of the homologous recombination reaction to the strand exchange phase. The double D-loop permits isolation of stable multistranded DNA recombination intermediates. The addition of anchoring sequences as described below provides significant further stability to the complexes.

The invention may also be practiced with individual targeting polynucleotides which do not comprise part of a complementary pair. In this case, a targeting polynucleotide is introduced into a target cell or target nucleic acid simultaneously or contemporaneously with a recombinase protein, typically in the form of a recombinase coated targeting polynucleotide as outlined herein (i.e., a polynucleotide pre-incubated with recombinase wherein the recombinase is noncovalently bound to the polynucleotide; generally referred to in the art as a nucleoprotein filament). In this embodiment, the single targeting polynucleotide targets both strands of a double strand target nucleic acid, thereby producing a double D-loop. Thus the targeting polynucleotide comprises a first homology clamp that substantially coresonds to the target nucleic acid and a second homology clamp that is substantially complementary to the target nucleic acid sequence. In a preferred embodiment, the targeting polynucleotide further comprises at least one anchoring sequence as described herein. In one embodiment, secondary probes or proteins that bind to the anchoring sequence are used to further stabilize the double D-loop structure. The single targeting polynucleotide optionally comprises additional homology clamps and/or anchoring sequences.

A targeting polynucleotide used in a method of the invention typically is a single-stranded nucleic acid, usually a DNA strand, or derived by denaturation of a duplex DNA, which is complementary to one (or both) strand(s) of the target duplex nucleic acid. Thus, one of the complementary single stranded targeting polynucleotides is complementary to one strand of the endogeneous target sequence (i.e. Watson) and the other complementary single stranded targeting polynucleotide is complementary to the other strand of the endogeneous target sequence (i.e. Crick). The homology clamp sequence preferably contains at least 90–95% sequence homology with the target sequence, to insure sequence-specific targeting of the targeting polynucleotide to the endogenous DNA target, although clamps with less homology may also be used, as outlined herein. Each single-stranded targeting polynucleotide is typically about 50–600 bases long, although a shorter or longer polynucleotide may also be employed. Alternatively, targeting polynucleotides may be prepared in single-stranded form by oligonucleotide synthesis methods, which may first require, especially with larger targeting polynucleotides, formation of subfragments of the targeting polynucleotide, typically followed by splicing of the subfragments together, typically by enzymatic ligation.

In addition to the homology clamps, the targeting polynucleotides further comprise at least one anchoring sequence. By "anchoring sequence" or "locking sequence" or grammatical equivalents herein is meant a sequence that confers stable secondary structure to a localized portion of the sequence, such that a stable structural complex is formed. In a preferred embodiment, the stability imparted to the structural complex is such that transcription or replication of the target nucleic acid is altered, i.e., enhanced or inhibited. By "stable structure" herein is meant a D-loop/anchoring sequence structure with a half-life of at least about 5 fold longer than the D-loop without the anchoring sequence. In a more preferred embodiment the half-life is at least about 10 fold longer and in a most preferred embodiment the half-life is at least about 20 fold longer or even longer. In a preferred embodiment, two targeting polynucleotides are used, and each comprises at least one anchoring sequence, although as will be appreciated by those in the art, more than one anchoring sequence per targeting probe may be used.

Similarly, in some embodiments, only one of the targeting probes comprises an anchoring sequence, for example. In this embodiment, one or more secondary probes, as is more fully described below, provide the additional sequences necessary to complete a lock structure.

In an alternative embodiment, the lock structures are further stabilized by the binding of proteins. For example, the lock structures are recognized in a sequence or structural specific manner by proteins. The binding of the proteins to the lock structures further stabilizes the structures. Preferably, the proteins recognize and bind to the locks structures but do decrease lock stability. Such proteins would include recombination and repair proteins, for example RuvC, fen1, and junction specific endonucleases, that are preferably modified, for example by gene-shuffling (Stemmer et al. Nature 370(6488):389–391; Crameri et al. Nature 391 (6664):288–291; Zhang et al. Proc. Natl. Acad. Sci. USA 94(9):4504–4509; Stemmer et al. Proc. Natl. Acad. Sci USA 91(22):10747–10751) to eliminate or reduce their enzymatic activities that may reduce the stability of the lock structure while increasing their affinity for the lock. Alternatively, peptide or nucleic acid libraries are screened for binding to lock structures.

In general, anchoring sequences are sequences that do not have significant homology to the target strands; i.e. they are "loops" that do not hybridize to the target strand, as generally pictured in FIG. 2B–E. Alternatively, as shown in FIG. 2C, the anchoring sequence of one probe may be part of a homology clamp, and the anchoring sequence of the other probe is designed with a loop that forms a triplex. The latter is generally not preferred because the formation of triplex structures requires sequence specificity (i.e. stretches of homopurine or homopyrimidine), and thus may not be generically useful, although this is perfectly acceptable when in fact the target sequence fills the requirements of triplex formation. In general, the anchoring sequence forms a duplex with itself, either with traditional Watson-Crick base pairing or via Hoogsteen pairing. In an alternative embodiment, the targeted nucleic acid contains an insert relative to the targeting polynucleotide and thus forms an internal homology clamp or anchoring sequence as depicted in FIG. 2F.

Anchoring sequences of each targeting polynucleotide of the invention comprise at least about 10 nucleotides, preferably at least about 14 nucleotides, more preferably at least about 20 nucleotides and most preferably at least about 50 or more nucleotides.

Anchoring sequences may take a number of forms. For example, anchoring sequences form duplex structures (i.e., A-DNA, B-DNA, C-DNA, Z-DNA), triplex structures (including H-DNA), quadruplex structures, internal homology clamps, and combinations thereof.

In a preferred embodiment, all or part of the anchoring sequences form triplex structures ("triplex locks" or "triplex anchors") as generally depicted in FIG. 2C. In this triplex embodiment, the orientation of the anchoring sequences can vary. As is known in the art, triplex formation can proceed via either Hoogsteen or reverse-Hoogsteen interactions in either parallel or antiparallel orientation.

In a preferred embodiment, the anchoring sequences form quadruplex structures ("quadruplex locks" or "quadruplex anchors") as generally depicted in FIG. 2D. Quadruplexes are formed mostly be sequences with G-blocks as described by Sundquist et al., (Nature 342:825 (1989)) and Belotserkovskii et al. (Biochemistry 38(33):10785–10792).

In a preferred embodiment, the anchoring sequences form traditional duplexes (structures with Watson-Crick base pairing) or hybrids and one or more additional sequences are contained on one or more additional probes (a "secondary" probe, as termed herein), that serve to complete the triplex or quadruplex locks, as is generally depicted in FIGS. 2D or 8A. This embodiment finds particular use in the targeting probes for the isolation (i.e. cloning) of sequences, as is generally depicted in FIG. 8, particularly with the use of a purification tag, more fully described below. In this embodiment, one or both of the targeting probes form a duplex with itself, and one or more secondary probes provide the additional required triplex or quadruplex forming sequences.

In addition, when probe sequences are designed to hybridize only to other probe sequences, it may be desirable in some instances to use artificial bases, such as isocytosine and isoguanine, to decrease non-specific binding, for example, of probe to target nucleic acid.

In addition, triplexes (and presumably quadruplexes) are poorly dissociated by copying enzymes (see Frank-Kamenetskii, supra, and Helene, supra), and thus, in one embodiment, serve to inactivate both gene expression and nucleic acid replication and induce mutagenesis and DNA strand breaks which can lead to enhanced homologous recombination (EHR).

Furthermore, without being bound by theory, it appears that one way that the locks of the present invention contribute to gene inactivation is as a result of the formation of single strand-double strand junctions. These junctions are shown in FIG. 4. These types of junctions are recognized by certain cell proteins in the activation of repair and recombination systems. For example, there are known junction-specific nucleases that may cut at these junctions, possibly causing excision of the target and/or increasing homologous recombination in this vicinity. Thus, for example, triplex formation can lead to triplex induced mutagenesis (see Wang et al., supra), leading to gene inactivation.

Thus, the use of anchoring or locking complexes in the invention provides a number of distinct advantages. For example, the stability of the triplex and quadruplex locks facilitates the in vitro manipulation of DNA, i.e. cloning and labelling, as is more fully described below.

In addition to anchoring sequences, the targeting polynucleotides may also contain internal homology clamps. Internal homology clamps are a simple form of anchoring sequence; that is, as shown, for example, in FIG. 2B, they are sequences of substantially complementary sequence between the two targeting polynucleotides that do not have significant homology to the endogeneous target sequence. Similar to anchoring sequences, the use of internal homology clamps allows the formation of more stable deproteinized cssDNA:probe target hybrids with homologous DNA sequences containing small or large insertions as compared to a homologous DNA target. Without being bound by theory, it appears that these probe:target hybrids, with heterologous inserts in the cssDNA probe, are stabilized by the re-annealing of cssDNA probes to each other within the double-D-loop hybrid, forming a novel DNA structure with an internal homology clamp. Because cssDNA probes are kinetically trapped within the duplex target, the multi-stranded DNA intermediates of homologous DNA pairing are stabilized.

The targeting polynucleotides may contain a deletion relative to the nucleic acid target to form an internal homology clamp. In this embodiment, an anchoring sequence comprising a homology clamp is formed by the base pairing of the regions of the target nucleic acid that are not hybridized to the targeting polynucleotides. An example of this type of internal homology clamp is shown in FIG. 2F. Without being bound by theory, it appears that these probe:target hybrids, with deletions in the cssDNA probe relative to the nucleic acid target are stabilized by the re-annealing of dsDNA target strands to each other within the double-D-loop hybrid, forming a novel DNA structure with an internal homology clamp.

In a preferred embodiment, the length of the anchoring sequence or internal homology clamp (i.e. the length of the insertion or deletion) is from about 1 to 50% of the total length of the targeting polynucleotide, with from about 1 to about 20% being preferred and from about 1 to about 10% being especially preferred, although in some cases the length of the internal homology clamp may be significantly larger. As for the targeting homology clamps, the complementarity within the internal homology clamp need not be perfect.

In an alternative embodiment, the double D-loop is stabilized by the use of an intercalator tethered to the back of at least one targeting polynucleotide (FIG. 20). The length and rigidity of the linker between the intercalator and the targeting polynucleotide or probe backbone is chosen such that the intercalator preferentially will not intercalate into the duplex (targeting polynucleotide-targeted nucleic acid duplex) to which it is tethered but rather the other duplex within the double D-loop. This design, in addition to kinetic trapping of probe-target hybrids, makes the probe-target hybrid energetically more favorable than probe-probe and target duplexes. An additional advantage is that the structures of FIG. 20 are efficiently formed and maintained both in proteinized and deproteinized hybrids.

In addition to homology clamps, anchoring sequences and internal homology clamps, the targeting polynucleotides of the invention may comprise additional components, including cell-uptake components and substituents, including proteins and chemical substituents, and linkers.

In a preferred embodiment, the targeting polynucleotides comprise cell-uptake components. As used herein, the term "cell-uptake component" refers to an agent which, when bound, either directly or indirectly, to a targeting polynucleotide, enhances the intracellular uptake of the targeting polynucleotide into at least one cell type (e.g., hepatocytes). A cell-uptake component may include, but is not limited to, the following: specific cell surface receptors such as a galactose-terminal (asialo-) glycoprotein capable of being internalized into hepatocytes via a hepatocyte asialoglycoprotein receptor, a polycation (e.g., poly-L-lysine), and/or a protein-lipid complex formed with the targeting polynucleotide. Various combinations of the above, as well as alternative cell-uptake components will be apparent to those of skill in the art and are provided in the published literature.

A targeting polynucleotide of the invention may optionally be conjugated, typically by covalently or preferably noncovalent binding, to a cell-uptake component. Various methods have been described in the art for targeting DNA to specific cell types. A targeting polynucleotide of the invention can be conjugated to essentially any of several cell-uptake components known in the art. For targeting to hepatocytes, a targeting polynucleotide can be conjugated to an asialoorosomucoid (ASOR)-poly-L-lysine conjugate by methods described in the art and incorporated herein by reference (Wu GY and Wu CH (1987) J. Biol. Chem. 262:4429; Wu GY and Wu CH (1988) Biochemistry 27:887; Wu GY and Wu CH (1988) J. Biol. Chem. 263:14621; Wu GY and Wu CH (1992) J. Biol. Chem. 267: 12436; Wu et al., (1991) J. Biol. Chem. 266: 14338; and Wilson et al., (1992) J. Biol. Chem. 267: 963, WO92/06180; WO92/05250; and WO91/17761, which are incorporated herein by reference).

Alternatively, a cell-uptake component may be formed by incubating the targeting polynucleotide with at least one lipid species and at least one protein species to form protein-lipid-polynucleotide complexes consisting essentially of the targeting polynucleotide and the lipid-protein cell-uptake component. Lipid vesicles made according to Felgner (WO91/17424, incorporated herein by reference) and/or cationic lipidization (WO91/16024, incorporated herein by reference) or other forms for polynucleotide administration (EP 465,529, incorporated herein by reference) may also be employed as cell-uptake components.

In addition to cell-uptake components, targeting components such as nuclear localization signals may be used, as is known in the art.

In a preferred embodiment, the targeting polynucleotides comprise at least one substitutent, such as a protein or chemical substituent. This may be done for any number of reasons, including, but not limited to, labelling the targeting probe (and thus the target sequence); increasing the stability of the heteroduplexes including the locks, for example via the use of cross-linking moieties; contributing to gene inactivation, for example by the incorporation of nucleic acid scission moieties. Exogenous targeting polynucleotides that have been modified with appended substituents may be introduced along with recombinase (e.g., RecA) into a target cell to homologously pair with a predetermined endogenous DNA target sequence in the cell. In a preferred embodiment, the exogenous targeting polynucleotides are derivatized, and additional substituents are attached, either during or after polynucleotide synthesis, respectively, and are thus localized to a specific endogenous target sequence where they produce an alteration, effect or chemical modification to a local DNA sequence. Preferred attached substituents are proteins and chemical substituents, and include, but are not limited to: cross-linking agents (see Podyminogin et al., Biochem. 34:13098 (1995) and 35:7267 (1996), both of which are hereby incorporated by reference), nucleic acid cleavage agents, met al chelates (e.g., iron/EDTA chelate for iron catalyzed cleavage), topoisomerases, endonucleases, exonucleases, ligases, phosphodiesterases, photodynamic porphyrins, chemotherapeutic drugs (e.g., adriamycin, doxirubicin), intercalating agents, photoactive moieties, nucleic acid modification moieties, labels, purification tags, base-modification agents, agents which normally bind to nucleic acids such as labels, etc. (see for example Afonina et al., PNAS USA 93:3199 (1996), incorporated herein by reference) immunoglobulin chains, and oligonucleotides. Iron/EDTA chelates are particularly preferred chemical substituents where local cleavage of a DNA sequence is desired (Hertzberg et al., (1982) J. Am. Chem. Soc. 104: 313; Hertzberg and Dervan (1984) Biochemistry 23: 3934; Taylor et al., (1984) Tetrahedron 40: 457; Dervan, PB (1986) Science 232: 464, which are incorporated herein by reference). Further preferred are groups that prevent hybridization of the complementary single stranded nucleic acids to each other but not to unmodified nucleic acids; see for example Kutryavin et al., Biochem. 35:11170 (1996) and Woo et al., Nucleic Acid. Res. 24(13):2470 (1996), both of which are incorporated by reference. 2'-O methyl groups are also preferred; see Cole-Strauss et al., Science 273:1386 (1996); Yoon et al., PNAS 93:2071 (1996)). Additional preferred chemical substitutents include labeling moieties, including fluorescent labels, and purification tags, for example to facilitate purification of target sequences. The substituent group may be directly or indirectly attached to the targeting polynucleotides, for example using linking moieties. Preferred attachment chemistries include: direct linkage, e.g., via an appended reactive amino group (Corey and Schultz (1988) Science 238:1401, which is incorporated herein by reference) and other direct linkage chemistries, although streptavidin/biotin and digoxigenin/ antidigoxigenin antibody linkage methods may also be used. Methods for linking chemical substituents are provided in U.S. Pat. Nos. 5,135,720, 5,093,245, and 5,055,556, which are incorporated herein by reference. Other linkage chemistries may be used at the discretion of the practitioner; the particular linking group is not critical, but one may be selected over another for synthetic convenience, to provide solubility, flexibility, hydrophobicity, enhanced activity or to remove secondary structure. Preferred linking groups generally span from about 1 (or zero, when direct linkage is used) to a chain of about 50 atoms, wherein the atoms can include carbon, nitrogen, oxygen, sulfur, phosphorus and the like. Generally alkyl and heteroalkyl linkers are preferred.

Linkers are well known in the art; for example, homo-or hetero-bifunctional linkers as are well known (see 1994 Pierce Chemical Company catalog, technical section on cross-linkers, pages 155–200, incorporated herein by reference). Preferred linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and C2 alkene being especially preferred. Suitable crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl) dithio]propioimidate.

The targeting probes, containing one or more of the above-mentioned structures, are made as is generally known in the art, and outlined herein. Once made, the targeting probes are generally combined with a recombinase. The recombinase in general is bound to or coats the targeting polynucleotides. The conditions used to coat targeting polynucleotides with recombinases such as RecA protein and ATPγS have been described in commonly assigned U.S. patent application Ser. No. 07/910,791, filed 9 Jul. 1992, abandoned, which is a continuation-in-part of U.S. patent application Ser. No. 07/755,462, now U.S. Pat. No. 5,273, 881; and U.S. Ser. No. 07/520,32 1, filed 7 May 1990, now U.S. Pat. No. 5,223,414, each incorporated herein by reference. The procedures below are directed to the use of E coli RecA, although as will be appreciated by those in the art, other recombinases may be used as well. Targeting polynucleotides can be coated using GTPγS, mixes of ATPγS with rATP, rGTP andlor dATP, or dATP or rATP alone in the presence of an rATP generating system (Boehringer Mannheim). Various mixtures of GTPγS, ATPγS, ATP, ADP, dATP and/or rATP or other nucleosides may be used, particularly preferred are mixes of ATPγS and ATP or ATPγS and ADP.

RecA protein coating of targeting polynucleotides is typically carried out as described in U.S. patent application Ser. No. 07/910,79 1, filed Jul. 9, 1992, abandoned, which is a continuation-in-part of U.S. patent application Ser. No. 07/755,462, now U.S. Pat. No. 5,273,881, which are incorporated herein by reference. Briefly, the targeting polynucleotide, whether double-stranded or single-stranded, is heated in an aqueous solution at 95–100° C. for five minutes, then placed in an ice bath for 20 seconds to about one minute followed by centrifugation at 0° C. for approximately 20 sec, before use. When denatured targeting polynucleotides are not placed in a freezer at −20° C. they are usually immediately added to standard RecA coating reaction buffer containing ATPγS, at room temperature, and to this is added the RecA protein. Alternatively, RecA protein may be included with the buffer components and ATPγS before the polynucleotides are added.

RecA coating of targeting polynucleotide(s) is initiated by incubating polynucleotide-RecA mixtures at 37° C. for 10–15 min. RecA protein concentration tested during reaction with polynucleotide varies depending upon polynucleotide size and the amount of added polynucleotide, and the ratio of RecA molecule:nucleotide preferably ranges between about 3:1 and 1:3. When single-stranded polynucleotides are RecA coated independently of their homologous polynucleotide strands, the mM and μM concentrations of ATPγS and RecA, respectively, can be reduced to one-half those used with double-stranded targeting polynucleotides (i.e., RecA and ATPγS concentration ratios are usually kept constant at a specific concentration of individual polynucleotide strand, depending on whether a single-or double-stranded polynucleotide is used).

RecA protein coating of targeting polynucleotides is normally carried out in a standard 1×RecA coating reaction buffer. 10×RecA reaction buffer (i.e., 10×AC buffer) consists of: 100 mM Tris acetate (pH7.5 at 37° C.), 20 mM magnesium acetate, 500 mM sodium acetate, 10 mM DTT, and 50% glycerol). All of the targeting polynucleotides, whether double-stranded or single-stranded, typically are denatured before use by heating to 95–100° C. for five minutes, placed on ice for one minute, and subjected to centrifugation (10,000 rpm) at 0° C. for approximately 20 seconds (e.g., in a Tomy centrifuge). Denatured targeting polynucleotides usually are added immediately to room temperature RecA coating reaction buffer mixed with ATPγS and diluted with double-distilled $H_2O$ as necessary. The glycerol in the reaction buffer is optionally omitted.

A reaction mixture typically contains the following components: (i) 0.2–4.8 mM ATPγS; and (ii) between 1–100 ng/μl of targeting polynucleotide. To this mixture is added about 1–20 μl of RecA protein per 10–100 μl of reaction mixture, usually at about 2–10 mg/ml (purchased from Pharmacia or purified), and is rapidly added and mixed. The final reaction volume-for RecA coating of targeting polynucleotide is usually in the range of about 10–500 μl. RecA coating of targeting polynucleotide is usually initiated by incubating targeting polynucleotide-RecA mixtures at 37° C. for about 10–15 min.

In a preferred embodiment, a targeting polynucleotide may contain a sequence that enhances the loading process of a recombinase, for example a RecA loading sequence is the recombinogenic nucleation sequence poly[d(A-C)], and its complement, poly[d(G-T)]. The duplex sequence poly[d(A-C)•d(G-T)$_n$, where n is from 5 to 25, is a middle repetitive element in target DNA.

RecA protein concentrations in coating reactions varies depending upon targeting polynucleotide size and the amount of added targeting polynucleotide: RecA protein concentrations are typically in the range of 5 to 50 μM. When single-stranded targeting polynucleotides are coated with RecA, independently of their complementary strands, the concentrations of ATPγS and RecA protein may optionally be reduced to about one-half of the concentrations used with double-stranded targeting polynucleotides of the same length: that is, the RecA protein and ATPγS concentration ratios are generally kept constant for a given concentration of individual polynucleotide strands.

The coating of targeting polynucleotides with RecA protein can be evaluated in a number of ways. First, protein binding to DNA can be examined using band-shift gel assays (McEntee et al., (1981) J. Biol. Chem. 256: 8835). Labeled polynucleotides can be coated with RecA protein in the presence of ATPγS and the products of the coating reactions may be separated by agarose gel electrophoresis. Following incubation of RecA protein with denatured duplex DNAs the RecA protein effectively coats single-stranded targeting polynucleotides derived from denaturing a duplex DNA. As the ratio of RecA protein monomers to nucleotides in the targeting polynucleotide increases from 0, 1:27, 1:2.7 to 3.7:1 for 121-mer and 0, 1:22, 1:2.2 to 4.5:1 for 159-mer, targeting polynucleotide's electrophoretic mobility decreases, i.e., is retarded, due to RecA-binding to the targeting polynucleotide. Retardation of the coated polynucleotide's mobility reflects the saturation of targeting polynucleotide with RecA protein. An excess of RecA monomers to DNA nucleotides is required for efficient RecA coating of short targeting polynucleotides (Leahy et al., (1986) J. Biol. Chem. 261: 954).

A second method for evaluating protein binding to DNA is in the use of nitrocellulose fiber binding assays (Leahy et al., (1986) J. Biol. Chem. 261:6954; Woodbury, et al., (1983) Biochemistry 22(20):4730–4737. The nitrocellulose filter binding method is particularly useful in determining the dissociation-rates for protein:DNA complexes using labeled DNA. In the filter binding assay, DNA:protein complexes are retained on a filter while free DNA passes through the filter. This assay method is more quantitative for dissociation-rate determinations because the separation of DNA:protein complexes from free targeting polynucleotide is very rapid.

Recombinase protein(s) (prokaryotic, eukaryotic or endogeneous to the target cell) may be exogenously induced or administered to a target cell simultaneously or contemporaneously (i.e., within about a few hours) with the targeting polynucleotide(s). Such administration is typically done by micro-injection, although electroporation, lipofection, and other transfection methods known in the art may also be used. Alternatively, recombinase-proteins may be produced in vivo. For example, they may be produced from a homologous or heterologous expression cassette in a transfected cell or transgenic cell, such as a transgenic totipotent cell (e.g. a fertilized zygote) or an embryonal stem cell (e.g., a murine ES cell such as-AB-1) used to generate a transgenic non-human animal line or a somatic cell or a pluripotent hematopoietic stem cell for reconstituting all or part of a particular stem cell population (e.g. hematopoietic) of an individual. Conveniently, a heterologous expression cassette includes a modulatable promoter, such as an ecdysone-inducible promoter-enhancer combination, an estrogen-induced promoter-enhancer combination, a CMV promoter-enhancer, an insulin gene promoter, or other cell-type specific, developmental stage-specific, hormone-inducible, or other modulatable promoter construct so that expression of at least one species of recombinase protein from the cassette can by modulated for transiently producing recombinase(s) in vivo simultaneous or contemporaneous with introduction of a targeting polynucleotide into the cell. When a hormone-inducible promoter-enhancer combination is used, the cell must have the required hormone receptor present, either naturally or as a consequence of expression a co-transfected expression vector encoding such receptor. Alternatively, the recombinase may be endogenous and produced in high levels. In this embodiment, preferably in eukaryotic target cells such as tumor cells, the target cells produce an elevated level of recombinase. In other embodiments the level of recombinase may be induced by DNA damaging agents, such as mitomycin C, cisplatin, etoposide, UV or γ-irradiation. Alternatively, recombinase levels may be elevated by transfection of a plasmid encoding the recombinase gene into the cell.

When cell-uptake components are used, a targeting polynucleotide of the invention is typically coated with at least one recombinase and is conjugated to a cell-uptake component, and the resulting cell targeting complex is contacted with a target cell under uptake conditions (e.g., physiological conditions) so that the targeting polynucleotide and the recombinase(s) are internalized in the target cell. A targeting polynucleotide may be contacted simultaneously or sequentially with a cell-uptake component and also with a recombinase; preferably the targeting polynucleotide is contacted first with a recombinase, or with a mixture comprising both a cell-uptake component and a recombinase under conditions whereby, on average, at least about one molecule of recombinase is noncovalently attached per targeting polynucleotide molecule and at least about one cell-uptake component also is noncovalently attached. Most preferably, coating of both recombinase and cell-uptake component saturates essentially all of the available binding sites on the targeting polynucleotide. A targeting polynucleotide may be preferentially coated with a cell-uptake component so that the resultant targeting complex comprises, on a molar basis, more cell-uptake component than recombinase(s). Alternatively, a targeting polynucleotide may be preferentially coated with recombinase(s) so that the resultant targeting complex comprises, on a molar basis, more recombinase(s) than cell-uptake component.

Cell-uptake components are included with recombinase-coated targeting polynucleotides of the invention to enhance the uptake of the recombinase-coated targeting polynucleotide(s) into cells, particularly for in vivo gene targeting applications, such as gene inactivation to treat genetic diseases and viral infections wherein a viral sequence (e.g., an integrated hepatitis B virus (HBV) genome or genome fragment) may be targeted by homologous sequence targeting and inactivated, as generally outlined below. Alternatively, a targeting polynucleotide may be coated with the cell-uptake component and targeted to cells with a contemporaneous or simultaneous administration of a recombinase (e.g., liposomes or immunoliposomes containing a recombinase, a viral-based vector encoding and expressing a recombinase).

Once the compositions of the invention are made, they find use in a wide variety of applications.

In a preferred embodiment, the compositions of the invention are used to label or modify endogenous target sequences. This can be done either in vitro, or in vivo, using metabolically active cells. In this embodiment, generally chemical substituents comprising labels are added to one or both of the targeting probes. By "label" herein is meant at least one element, isotope or chemical compound that serves to enable the detection of the compound to which it is attached. In general, labels fall into three classes: a) isotopic labels, which may be radioactive or heavy isotopes; b) immune labels, which may be antibodies or antigens; and c) colored or fluorescent dyes. The labels may be incorporated into the compound at any position. The labels can be direct or indirect labels; that is, moieties that can be detected can be added directly to the targeting probes. Preferred labels in this embodiment include, but are not limited to, fluorescent labels such as rhodamine, fluorescein, cascade blue, 6-FAM, TAMRA, or ROX and other labels as described in Haugland (ed), "The Molecular Probes Handbook of Flourescent Probes and Research Chemicals, Sixth Edition", expressly incorporated by reference. In a preferred embodiment, a plurality of direct labels are added to the probes. Alternatively, the label can be indirect; that is, a moiety is attached to one or both the probe that is then used to bind a detectable moiety. Preferred indirect labels include, but are not limited to, biotin and digoxigenin.

In a preferred embodiment, the labelled targeting probes are used for in vitro labelling of target sequences. In this embodiment, the labelled targeting probes are added to a sample for which the presence or absence of a target sequence is to be determined, in a manner similar to known techniques. However, the present invention provides a distinct advantage in that since the targeting probe pairs target double-stranded nucleic acid, there is no required denaturation step. Generally, the cells are lysed and the targeting probes are added and allowed to interact with the endogenous nucleic acid, under conditions that favor the formation of the heteroduplexes of the invention, i.e. generally physiological conditions.

In a preferred embodiment, the labelled targeting probes are used for the in vivo labelling of metabolically active cells. A metabolically-active cell is a cell, comprising an intact nucleoid or nucleus, which, when provided nutrients and incubated in an appropriate medium carries out DNA synthesis and RNA for extended periods (e.g., at least 12–24 hours). Such metabolically-active cells are typically undifferentiated or differentiated cells capable or incapable of further cell division (although non-dividing cells many undergo nuclear division and chromosomal replication), although stem cells and progenitor cells can also be metabolically-active cells. Suitable metabolically active cells include any of those cells described below for gene regulation or inactivation. In general, the compositions of the invention may be introduced to metabolically active human cells encapsulated in agarose microbeads and permeabilized to permit entry of DNA/protein complexes using the Jackson-Cook method (Cook, P. R. (1984) EMBO J. 3: 1837; Jackson and Cook (1985) EMBO J. 4: 919; Jackson and Cook (1985) EMBO J. 4: 913; Jackson and Cook (1986) J. Mol. Biol. 192: 65; Jackson et al., (1988) J. Cell. Sci. 90: 365, which are incorporated herein by reference). Jackson and Cook have previously demonstrated that the nuclear membranes of human or other cells may be permeabilized without loss of metabolic function of the cells when the cells are first encapsulated in a gel of agarose microbeads. The agarose microbead coat contains the cell constituents and preserves native conformation of chromosomal DNA, while permitting diffusion of macromolecules into and out of the cell compartment. Wittig et al.(1991) Proc. Natl. Acad. Sci.

(U.S.A.), 88: 2259, which is incorporated herein by reference, demonstrated that monoclonal antibodies directed against left-handed Z-DNA could be diffused into these agarose-embedded cells, and that the antibodies were specifically targeted to chromosomal sequences and conformations.

In a preferred embodiment, the compositions of the invention are used to isolate endogeneous target sequences, i.e. for cloning. This may be done in a variety of ways for a variety of purposes. In one embodiment, the presence or absence of a target sequence can be verified using the probes of the invention. In a preferred embodiment, native target sequences (including genes, regulatory sequences, sequence motifs, etc.) can be rapidly cloned using the compositions of the invention, for example, to allow the sequencing of the native gene to search for polymorphisms or mutations. In addition, since the targeting probes can tolerate significant heterologies, gene families and homologous genes may be cloned using the targeting probes of the invention.

The ability of RecA driven targeting reaction to tolerate relatively long heterology between the probe and the target provides an opportunity to use heterologous insert in the probe for binding to the agents used in DNA separation and isolation (for example, magnetic beads). A examples are illustrated in FIG. 8A. In this example, generally, the heterologous insert forms homopurine-homopyrimidine triplex with homopurine or homopyrimidine oligonucleotide comprising a tether such as a label, a magnetic bead, a solid surface, biotin etc. for isolation. After isolation of the target DNA from the sample the triplex is dissociated by changing conditions, which do not affect significantly the stability of Watson-Crick duplexes (for example, increasing the pH from 5 to 8 in the case of pyrimidine-purine-pyrimidine triplexes, or removing di- and polyvalent cations in the case of purine-purine-pyrimidine triplexes). In addition, this system is preferably designed in such a way that the binding of the tethered oligonucleotide to the probe stabilizes the probe-target complex (FIG. 8A, lower left and lower right structures. This enables the practitioner to use increased stringency for isolation and, consequently, the selectivity of isolation.

In another embodiment, one of the targeting probe polynucleotides has a heterologous sequence at the 5-prime end and the 3-prime end has a consensus sequence (i.e., a homology motif tag). In other words, the 5-prime end of one of the probes contains the triplex forming homopurine-homopyrimidine sequence that is heterologous to the target and the 3-prime end of the probe contains the consensus sequence. After the double D-loop structure is formed, a triplex forming homopurine or homopyrimidine oligonucleotide that is, for example, biotinylated is added to the complex. The resulting triplex containing double D-loop is isolated using the biotin "handle" or tether and the target nucleic acid is released from the hybrid by changing the pH. This embodiment is preferred for targeting and isolating gene families that share a consensus sequence. domain Examples of consensus sequences include the G-protein coupled receptor family (R7G subfamily, Secretin subfamily, metabotropic glutamate subfamily, phermone subfamily); bZIP transcription factor family; DNA mismatch repair (mutL, hexB, PMS1), mutS family, recA family, recF family, Bcl-2 family, TFIID transcription family, TGF-beta family, TNF family, Xeroderma pigmentosa (XP) family. Other motifs and methods of targeting are found in PCT publication WO99/37755, expressly incorporated by reference.

In this embodiment, the targeting polynucleotides of the invention preferably comprise a purification tag. A "purification tag" is a moiety whose presence facilitates purification or isolation of either the targeting polynucleotide to which it is attached or the hybrid (i.e. the targeting probe hybridized to the target sequence). A wide variety of purification tags are known, and include solid supports (for example beads, including magnetic beads), the His6 tag for use with Ni affinity columns, and epitope tags for detection, immunoprecipitation or FACS (fluoroscence-activated cell sorting). Suitable epitope tags include myc (for use with the commercially available 9E10 antibody), the BSP biotinylation target sequence of the bacterial enzyme BirA, flu tags, lacZ, and GST (see for example, FIG. 8).

In a preferred embodiment, the purification tag is a solid support such as a bead, particularly magnetic beads. The secondary probes are attached in any number of ways, as will be appreciated by those in the art, and generally include the use of a linker.

In one embodiment, two substantially complementary RecA coated targeting polynucleotides preferably comprising a label, for example biotin (FIGS. 8A and 8B), are added to a nucleic acid sample. The targeting polynucleotides form a double D-loop with the targeted nucleic acid sequence.

The targeted nucleic acid is captured or isolated for example by streptavidin beads that binds to the biotin label. In an alternative embodiment, the process is repeated. The isolated target nucleic acid is purified, cloned and/or amplified as needed. Preferably, the isolated target nucleic acid is sequenced which provides sequences for additional targeting polynucleotides to enable the targeting of additional nucleic acid sequences. In a preferred embodiment, the nucleic acid sample is a genomic or cDNA library. Alternatively, the nucleic acid sample is a library of uncloned, genomic DNA.

In a preferred embodiment, the compositions of the invention are used for gene regulation, either inactivation or enhanced expression (gene in this context including any nucleic acid sequences, including coding and non-coding regions). This may also be done for a wide variety of reasons. For example, the elucidation of gene function may be done using the present invention, in a manner similar to "gene knock-outs" or "gene knock-ins". Alternatively, the compositions may be used as therapeutic compositions, to turn off the expression of undesirable genes, for example to turn off disease alleles.

Genes of interest will vary widely, as will be appreciated by those in the art, and can be any sequence of interest, coding or non-coding. Generally, the endogeneous sequences are genes, however, the probes may be directed against any target sequence associated with replication, such as a centromere, teleomere, replication origin, or the like, repetitive sequences, etc., including regulatory sequences (promoters, enhancers, TATA boxes, transcription initiation and termination sequences, sequence motifs, or sequences that encode amino acid motifs, etc.

Without being bound by theory, the compositions of the present inventions reduce or inhibit gene expression or replication by interfering with the polymerases, such as RNA and/or DNA polymerases, that transcribe or replicate a target sequence. Alternatively, target nucleic acid sequence transcription or replication is enhanced by preferably targeting regulatory sequences. In this embodiment, the compositions of the invention "open" the regulatory sequence, thereby facilitating or enhancing the transcription or replication of the downstream sequences. Without being bound by theory, opening of double stranded DNA by a D-loop thereby promotes transcription or replication from an endogenous promoter or replication origin; or prevent or disrupt repressor binding; or, in a preferred embodiment, the D-loop structure serves as a promoter or origin or replication.

Suitable genes of interest for regulation may be associated with housekeeping, proliferation, differentitaiton, activation, transcription, oncogenesis, and the like, including cellular genes and genes associated with pathogens such as microorganisms, parasites, viruses, fungi, etc., such as genes associated with transcription factors, polymerases, reverse transcriptases, helicases, topoisomerases, capsid antigens, coat proteins, integrases, adhesion proteins, and the like. The particular target can depend on the purpose for which the probe is employed. Targets of interest include oncogenes, transcription factor genes, proliferation repressor genes, mutant tumor suppressor genes, segmental polarization genes, homeobox genes, addressin genes, homing receptor genes, major histocompatibility complex genes, immunoglobulin genes, cytokine genes, immunosuppressive transforming growth factor genes, colony stimulating factor genes, drug pump genes (mdr genes), integrin genes, enzyme genes, cytostructural genes, membrane channel genes, etc. In some instances, one may wish to block the 3' untranslated region (3' UTR), where the 3' UTR is known to have a regulatory function. In this manner, one may determine what functions are regulated by the 3' UTR. Target oncogenes for the treatment of cancer include src, ras, sis, fos, erb, erbb2, neu, myc, gli, etc. Other genes to be inhibited include receptors, such as the EGF receptor, estrogen receptors, PDGF receptor, viral receptors, including CD4 for HIV, and the like.

Also, various specialized proteins may be of interest for regulation, such as telomerases, in understanding senescence, heat shock proteins, in understanding response to adverse conditions in their activity in helping folding of proteins, recombinases, in understanding processes involved with correction and DNA modification, viral integrases and rep proteins in understanding processes in viral replication and integration, polymerases, in understanding the roles specialized polymerases play, zinc finger DNA binding proteins involved in transcription, and the like.

In this embodiment, the targeting probes are added to target cells putatively containing the endogeneous sequences of interest. Thus, for this and other embodiments, once the recombinase-targeting polynucleotide compositions are formulated, they are introduced or administered into target cells. The administration is typically done as is known for the administration of nucleic acids into cells, and, as those skilled in the art will appreciate, the methods may depend on the choice of the target cell. Suitable methods include, but are not limited to, microinjection, electroporation, lipofection, etc.

By "target cells" herein is meant prokaryotic or eukaryotic cells. Suitable prokaryotic cells include, but are not limited to, a wide variety of pathogenic and non-pathogenic prokaryotes of interest including *Bacillus; Vibrio*, e.g. *V. cholerae; Escherichia*, e.g. Enterotoxigenic *E. coli; Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C.perfringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *G. lamblia Y. pestis, Pseudomonas*, e.g. *P. aeruginosa, P. putida; Chlamydia*, e.g. *C. trachomatis; Bordetella*, e.g. *B. pertussis; Treponema*, e.g. *T. palladium*; and the like. Preferably, the procaryotic target cells are recombination competent.

Viral groups of interest include orthomyxoviruses, e.g. influenza virus; paramyxoviruses, e.g respiratory syncytial virus, mumps virus, measles virus; adenoviruses; rhinoviruses; coronaviruses; reoviruses; togaviruses, e.g. rubella virus; parvoviruses; poxviruses, e.g. variola virus, vaccinia virus; enteroviruses, e.g. poliovirus, coxsackievirus; hepatitis viruses, e.e. hepatitis B virus, hepatitis C virus; herpesviruses, e.g. Herpes simplex virus, varicella-zoster virus, cytomegalovirus, Epstein-Barr virus; rotaviruses; Norwalk viruses; hantavirus; arenavirus, rhabdovirus, e.g. rabies virus; retroviruses, such as HIV, HTLV-I and -II; papovaviruses, e.g. papillomavirus; polyomaviruses; picornaviruses; and the like.

Suitable eukaryotic cells include, but are not limited to, fungi such as yeast and filamentous fungi, including species of *Aspergillus, Trichoderma,* and *Neurospora*; plant cells such as seed, grain, root, stem leaf etc of monocotyledonous and dicotyledonousthos plants (in wheat (*Triticum* spp.), rice (*Oryza* spp.), barley (*Hordeum* spp.), oat (*Avena* spp.), rye (*Secale* spp.), maize, corn (*Zea mays*), sorghum (*Sorghum* spp.), millet (*Pennisetum* spp.), *Brassica* spp., soybean, cotton, beans in general, rape/canola, alfalfa, flax, sunflower, canola, safflower, cotton, tobacco, flax, peanut, clover, cowpea, grapes, forages grass varieties; vegetables such as lettuce, tomato, curcurbits, cassava, potato, carrot, radish, pea, lentils, cabbage, sugar beets, cauliflower, broccoli, sugar beats, Brussels sprouts, peppers; tree fruits such as citrus, apples, pears, peaches, apricots, walnuts; and ornamentals such as turf grasses, carnations and roses etc); and animal cells, including fish, birds and mammals. Suitable fish cells include, but are not limited to, those from species of salmon, trout, tulapia, tuna, carp, flounder, halobut, swordfish, cod and zebrafish. Suitable bird cells include, but are not limited to, those of chickens, ducks, quail, pheasants and turkeys, and other jungle foul or game birds. Suitable mammalian cells include, but are not limited to, cells from horses, cows, buffalo, deer, sheep, rabbits, rodents such as mice, rats, hamsters and guinea pigs, goats, pigs, primates, marine mammals including dolphins and whales, as well as cell lines, such as human cell lines of any tissue or stem cell type, and stem cells, including pluripotent and non-pluripotent, and non-human zygotes. Pathogenic eukaryotes of interest for use of target cells include *Cryptococcus*, e.g. *C. neoformans; Candida*, e.g. *C. albicans; Histoplasma*, e.g. *H. capsulatum; Coccidoides*, e.g. *C. immitus; Giardia*, e.g. *G. lamblia; Plasmodium*, e.g. *P. falciparum, P. malariae, P. vivax; Toxoplasma*, e.g. *T. gondii*; Leishmania, e.g. *L. mexicana*; and the like.

Transformation and regeneration of both monocotyledonous and dicotyledonous plant cells is routine in the art and the practitioner will determine the appropriate transformation technique. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; microinjection of plant cells; micro-projectile bombardment of plant cells; vacuum infiltration; and *Agrobacterium tumefaciens* (AT)-mediated transformation. Typical procedures for transforming and regenerating plants are described U.S. Pat. Nos. 5,571,706; 5,677,175; 5,750,386; 5,597,945; 5,589, 615; 5.750,871; 5,268,526; 5,780,708; 5,538,880; 5,773, 269; 5,736,369; 5,610,042; 5,780,709; and PCT publication WO 98/48613; Omirulleh et al. Plant Mol. Biol. 1993 February;(21):415–412; Rhodes et al. Science 1988 Apr.

8;8(240(4849):204–207; Fromm et al. Biotechnology (NY) 1990 September;8(9):833–839; Ko et al. 1993. In Vitro (29A, 3, Pt. 2, 70A); Somers et al. Biotechnology 1992, 10:1589–1594; Brown et al. Mol. Gen. Genet. 1993 March;237(3):311–317; Casas et al. Proc. Natl. Acad. Sci. USA 1993 Dec. 1;90(23):11212–11216; Ritala et al. Plant Mol. Biol. 1994 January;24(2):317–325 report the production of fertile transgenic barley by particle bombardment of immature embryos. In addition, certain developments particularly enhance regeneration techniques for monocot plants (see, for instance, U.S. Pat. Nos. 4,666,844 and 5,589,617; PCT application WO 98/48613).

When the subject probes are used in culture (i.e. in vitro), the probes will be introduced into the culture at an effective concentration based on the number of cells to provide the desired level of inhibition. Usually, the ratio of probe to target sequence will be in the range of about 1–30:1, more usually in the range of about 2–25:1. Therefore, the amount of probe which is employed will be dependent upon the number of target sequences present, by virtue of the number of cells, the number of copies of the target sequence, the number of integrated viruses, the number of viral molecules, the number of episomal elements, or the like. The probes are able to cross the membrane barrier and be taken up by the cells, although various techniques can be employed to enhance the efficiency of translocation into the cytoplasm of the cell. For example, one may use liposomes, where the liposome comprises the fusogenic HVJ protein of the Sendai virus or respiratory syncytial virus or gramicidin S peptide. By providing for preparation of the liposomes in the presence of the probes, the probes will be incorporated into the lumen of the liposomes. The liposomes will then fuse with the cellular membrane releasing the probes into the cytoplasm of the cell. Lipofection may be employed using DOTAP (Boehringer Mannheim). Other techniques include electroporation, fusion, microinjection, biolistics, polyamidoamine dendrimer complexes, and the like.

The subject compositions may be administered systemically or locally. For many applications, local administration will be preferred. Systemic application will generally involve parenteral application, particularly injection, where the injection may be intravascular, intramuscular, peritoneal, subcutaneous, etc. As indicated above, the subject compositions may be administered without incorporation into a liposome or other vehicle or by incorporation into a liposome. Physiologically acceptable vehicles will be employed, such as water, saline, phosphate buffered saline, ethanol, vegetable oil, etc. The amount of the probes which is employed will vary depending upon the particular target, the manner of administration, the frequency of administration, the stability of the probes, and the like. Generally, amounts which will be employed systemically will provide for a blood concentration in the range of about 1 mM to 10 $\mu$M.

For local administration, various techniques may be employed. Particularly, for a region which can be reached with a needle, one may use the subject compositions in conjunction with a matrix which slows the transport of the subject compositions away from the locale at which the subject compositions are introduced, or with a pump which provides for continuous local infusion. Various matrices have been employed, such as collagen, fibrinogen, hyaluronic acid and the like. Generally, the subject compositions will range in from about 0.5 to 70, more usually from about 1 to 35 weight percent of the composition. Other compositions may be present, such as vasoconstrictors, stabilizers, or other agents, depending upon the purpose for which the subject compositions are employed.

For treatment of cancer, the subject compositions may be used in conjunction with cytotoxic agents, where the cytotoxic agents are at or below their normal concentration. Thus, by employing a combination of the subject compositions with cytotoxic agents, the cytotoxic agent can be used at from about 10 to 60% of its normal therapeutic dosage. Cytotoxic agents include cisplatin, vinca alkaloids, 5-fluorouracil, adriamycin, methotrexate, actinomycin D, BCNU, etoposide etc.

The subject compositions may be used for inhibiting specific cell lineage development, e.g., NK, LAK, B- and T-cell development, by inhibiting the expression of CD4, CD8, or a member of the CD3 complex. Other proteins associated with activation may also be the subject of inhibition, either individually or in conjunction with the inhibition of other genes. In addition, the subject compositions can be used to inhibit cytokines associated with specific activation, such as IL-2 and IL-4. By inhibiting expression of IL-4, allergic responses can be diminished.

The subject compositions may also be employed in producing animal models for a wide variety of diseases associated with genetic defects. Thus, those diseases where the lack of a competent protein results in an adverse phenotype can be studied in animal models, where by employing the subject compositions, expression of the particular protein may be inhibited for an extended period of time. Also, by varying the nature of the sequence, as to its terminal groups and degree of homology, the period of time for the inhibition, as well as the level of inhibition, may be modulated, so as to have a model where the phenotype may be reversed. Animal models may be developed associated with the inhibition of expression of apolipoproteins, cytokines, recombinases, proteins associated with differentiation, growth and maturation, such as CD4, CD8, growth factor receptors, interferon receptors, virus receptors, and the like. Particularly, mice and rats may be temporarily or permanently modified as to phenotype, depending upon the nature of the probes, the concentration employed, whether the probes have the ability to permanently modify the DNA, and the like.

In a preferred embodiment, procaryotic cells are used. In this embodiment, a pre-selected target DNA sequence is chosen for labelling, cloning or inhibition. Preferably, the pre-selected target DNA sequence is contained within an extrachromosomal sequence. By "extrachromosomal sequence" herein is meant a sequence separate from the chromosomal or genomic sequences. Preferred extrachromosomal sequences include plasmids (particularly procaryotic plasmids such as bacterial plasmids), p1 vectors, viral genomes, yeast, bacterial and mammalian artificial chromosomes (YAC, BAC and MAC, respectively), and other autonomously self-replicating sequences, although this is not required. As described herein, a recombinase and at least two single stranded targeting polynucleotides which are substantially complementary to each other, each of which contain a homology clamp to the target sequence contained on the extrachromosomal sequence, are added to the extrachromosomal sequence, preferably in vitro. The two single stranded targeting polynucleotides are preferably coated with recombinase, and at least one of the targeting polynucleotides contain at least one anchoring sequence. The targeting polynucleotides then bind to the target sequence in the extrachromosomal sequence to effect locking. The locked extrachromosomal sequence is then introduced into the procaryotic cell using techniques known in the art. Preferably, the recombinase is removed prior to introduction into the target cell, using techniques known in the art. For example, the reaction may be treated with proteases such as proteinase K, detergents such as SDS, and phenol extraction (including phenol:chloroform:isoamyl alcohol extraction). These methods may also be used for eukaryotic cells.

Alternatively, the pre-selected target DNA sequence is a chromosomal sequence. In this embodiment, the recombinase with the targeting polynucleotides are introduced into the target cell, preferably eukaryotic target cells. In this embodiment, it may be desirable to bind (generally non-covalently) a nuclear localization signal to the targeting polynucleotides to facilitate localization of the complexes in the nucleus. See for example Kido et al., Exper. Cell Res. 198:107–114 (1992), hereby expressly incorporated by reference. The targeting polynucleotides and the recombinase function to effect locking, for the purposes described herein.

In a preferred embodiment, eukaryotic cells are used. For making transgenic non-human animals (which include homologously targeted non-human animals) embryonal stem cells (ES cells) and fertilized zygotes are preferred. Methods of making transgenic animals are hereby incorporated by reference to co-assigned application Ser. No. 09/470,859, expressly incorporated by reference. In a preferred embodiment, embryonal stem cells are used. Murine ES cells, such as AB-1 line grown on mitotically inactive SNL76/7 cell feeder layers (McMahon and Bradley, Cell 62: 1073–1085 (1990)) essentially as described (Robertson, E. J. (1987) in Teratocarcinomas and Embryonic Stem Cells: A Practical Approach. E. J. Robertson, ed. (oxford: IRL Press), p. 71–112) may be used for homologous gene targeting. Other suitable ES lines include, but are not limited to, the E14 line (Hooper et al., (1987) Nature 326: 292–295), the D3 line (Doetschman et al., (1985) J. Embryol. Exp. Morph. 87: 21–45), and the CCE line (Robertson et al., (1986) Nature 323: 445–448). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal).

The pluripotence of any given ES cell line can vary with time in culture and the care with which it has been handled. The only definitive assay for pluripotence is to determine whether the specific population of ES cells to be used for targeting can give rise to chimeras capable of germline transmission of the ES genome. For this reason, prior to gene targeting, a portion of the parental population of AB-1 cells is injected into C57B1/6J blastocysts to ascertain whether the cells are capable of generating chimeric mice with extensive ES cell contribution and whether the majority of these chimeras can transmit the ES genome to progeny.

In a preferred embodiment, non-human zygotes are used, for example to make transgenic animals, using techniques known in the art (see U.S. Pat. No. 4,873,191). Preferred zygotes include, but are not limited to, animal zygotes, including fish, avian and mammalian zygotes. Suitable fish zygotes include, but are not limited to, those from species of salmon, trout, tuna, carp, flounder, halibut, swordfish, cod, tulapia and zebrafish. Suitable bird zygotes include, but are not limited to, those of chickens, ducks, quail, pheasant, turkeys, and other jungle fowl and game birds. Suitable mammalian zygotes include, but are not limited to, cells from horses, cows, buffalo, deer, sheep, rabbits, rodents such as mice, rats, hamsters and guinea pigs, goats, pigs, primates, and marine mammals including dolphins and whales. See Hogan et al., Manipulating the Mouse Embryo (A Laboratory Manual), 2nd Ed. Cold Spring Harbor Press, 1994, incorporated by reference.

The vectors containing the DNA segments of interest can be transferred into the host cell by well-known methods, depending on the type of cellular host. For example, microinjection is commonly utilized for target cells, although calcium phosphate treatment, electroporation, lipofection, biolistics or viral-based transfection also may be used. Other methods used to transform mammalian cells include the use of Polybrene, protoplast fusion, and others (see, generally, Sambrook et al. Molecular Cloning: A Laboratory Manual, 2d ed., 1989, Cold Spring Harbor Laboratory Press, Cold Spring Harbor, N.Y., which is incorporated herein by reference). Direct injection of DNA and/or recombinase-coated targeting polynucleotides into target cells, such as skelet al or muscle cells also may be used (Wolff et al., (1990) Science 247: 1465, which is incorporated herein by reference).

Accordingly, the compositions and methods of the invention find use in the in vitro and in vivo modulation of a target nucleic acid expression and replication. By "modulation" and grammatical equivalents herein are meant increased or decreased expression, replication, or activity of a target nucleic acid. In a preferred embodiment, a target nucleic acid sequence activity is modulated at least about 10 fold, in a more preferred embodiment, at least about 100 fold, in a most preferred embodiment at least about 1000 fold or higher.

Modulation of target nucleic acid expression or replication finds use in determining the a biological function of a target nucleic acid. An altered phenotype of an organism or cell is induced by the compositions provided herein is used to assign a biological function to the target nucleic acid sequence. By "altered phenotye" herein is meant that the phenotype of the organisms or a cell is altered in a detectable or measurable way: Altered phenotypes include, for example, morphology, growth, viability, expression of a protein, lipid, carbohydrate, hormone, biological factor, nucleic acid, sensitivity or lack thereof to a biological factor or hormone etc. Thus, the compositions and methods of the present invention find use in the treatment or prevention of a disease state by either directly altering the expression or replication of a disease gene or allele and/or altering the expression or replication of a second gene or allele to compensate or inhibit the disease gene or allele.

In general, gene inactivation ("gene" in this context including both coding and non-coding sequences) is facilitated. Inactivation of function may be assayed in a number of ways, as will be appreciated by those in the art, and will depend on the target sequence. Generally phenotypic or biological assays can be run; alternatively, mRNA levels may be quantitated, for example by northern blot of RT-PCR.

In all of the embodiments, more than one set of targeting probes may be used. For example, when gene inactivation is desired, one set of probes may be directed against regulatory elements and an additional set of probes may be directed against all or part of a structural gene.

In a further aspect, the invention provides kits comprising at least one recombinase and at least two substantially complementary single-stranded targeting polynucleotides, each containing at least one homology clamp that substantially corresponds to or is substantially complementary to a preselected target nucleic acid sequence and at least one anchoring sequence.

In a preferred embodiment, the kits further comprise targeting moieties, linkers, labels, DNA modifying moieties, purification tags, scission moieties, proteins, cell-targeting moieties and the like.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety.

EXAMPLES

Example 1

Increased Kinetic Stability of Triplex and Quadruplex Locks

In this example, the thermal stability of a triplex and quadruplex locks was evaluated as compared to targeting polynucleotides lacking an anchoring sequence.

Three sets of complementary single stranded (css) probes were designed as follows. The target sequence was the 62 nucleotides from bases 667 to 723 of pBluescript II SK(−) (Stratagene. LaJolla, Calif., FIG. 9A). The control reaction comprises two complementary single stranded nucleic acids (cssDNA) comprising these 62 bases and their complement. Targeting polynucleotides comprising the quadruplex forming lock 5-TTGGGGTTGGGGTT (SEQ ID NO:9) are shown in FIG. 9C (Sundquist et al., (1989)). Targeting polynucleotides also were made comprising the triplex forming lock GGGTGGTGGGTGGGGTATTAGGG-GAGGGAGGAGGG (SEQ ID NO:17) inserted in the sequence (Dayn et al., PNAS USA 89:11406 (1992)).

The targeting polynucleotides were obtained either by chemical synthesis. Oligonucleotides and pBluescript II SK(−) purification, RecA coating of oligonucleotides, targeting reactions, and deproteinization of hybrids by SDS treatment were performed as described in Example 2.

Hybrids were linearized by ScaI or PvuII restriction enzyme digestion. To compare the stability of the three hybrids (control, quadruplex, and tripex hybrids), hybrids were incubated at 65° C., neutral pH in 6 mM $Mg^{2+}$, 50 mM $Na^{+}$, 50 mM $K^{+}$. At various time points after commencement of 65° C. incubation, hybrid decay was demonstrated by gel-shift assay (Sena et al., Nat. Genet. 1993 3(4):365–372). The results shown in FIGS. 6 and 7 demonstrate that hybrids with heterologous inserts (i.e., triplex or quadruplex sequences) decay much slower than hybrids with completely homologous probes (controls).

Example 2

DNA Hybrids Stabilized by Heterologies

The double D-loop DNA hybrid contains four DNA strands following hybridization of two RecA protein coated complementary single-stranded DNA probes with a homologous region of a double-stranded DNA target. A remarkable feature of the double D-loop DNA hybrids is their kinetic stabilities at internal sites with linear DNA targets after removal of RecA proteins from hybrids. DNA heterologous normal distort DNA-DNA hybrids and consequently accelerate the stability of protein-free double D-loop hybrids. Here we show that heterologous DNA inserts impede dissociation of double D-loops.

Without being bound by theory, we propose a mechanism for stabilization of heterologous DNA isnerts based on the hypothesis that the main pathway of dissociation of double D-loop DNA hybrids is a DNA branch migration process involving rotation of both probe-target duplexes in the hybrids. Heterologous DNA inserts constrain rotation of probe-target duplexes and consequently impede hybrid dissociation.

To understand both thermodynamic and kinetic similarities and differences between single and double D-loop hybrids we examined the dissociation of protein-free D-loop hybrids. With either linear, or nicked circular target DNAs, formation of D-loops does not effect overall target DNA conformation. In contrast, within negatively supercoiled target DNAs, D-loops are stabilized by decrease in free energy due to removal of negative superhelical turns in hybrids (Beattie et al., (1977) J. Molec. Biol. 116, 825–839). D-loop hybrid dissociation is driven by a gain in entropy due to separation of the dissociated products. The hybrid dissociation process is reversible if the gain in entropy is compensated by additional DNA base pairing within the dissociating hybrid. In the case of D-loops, the products of dissociation (i.e. intact double-stranded target DNA and single or double-stranded free probe in the case of single or double D-loop, respectively) contain the same total number of base pairs as in the initial D-loop. Thus, dissociation proceeds without decreasing the total number of DNA base pairs. In addition, target DNA duplexes which contains D-loops, should have structural distortions in comparison with intact target DNA. Consequently, in the case of linear (or nicked) target DNAs, the dissociation of both single and double D-loops is irreversible. However, there is a dramatic differences in the kinetic stabilities (i.e. characteristic times of dissociation) between these DNA structures. For example, the estimated time of dissociation for single D-loops having a length of about 100 bp under near-physiological ionic, pH and temperature conditions is less than one second (Beattie et al., (1977) J. Molec. Biol. 116, 825–839). In contrast, the time of dissociation for double D-loop of a similar length under similar conditions is at least several hours (Sena et al., (1993) Nature Genet. 3, 365–372; Jaysena et al., (1993) J. Molec. Biol. 230, 1015–1024).

To understand these dramatic differences in kinetic stabilities between single and double D-loops, we examined pathways of dissociation of these two DNA structures. Within a single D-loop, a simple DNA branch-migration process is possible resulting in one base of the probe DNA in the probe-target duplex substituted by one base of the displaced target DNA strand, and vice versa (Lee et al., (1970) J. Molec. Biol. 48, 1–22). Due to this process, the junction between probe-target and target-target DNA duplexes migrates randomly. Occasionally, it reaches the edge of the position of the probe-target duplex and then the probe DNA strand irreversibly dissociates from the hybrid. Each step of the branch migration pathway of hybrid dissociation is isoenergetic because a newly formed base pair is equivalent to one formed by a displaced DNA base. The isoenergetic characteristics of DNA branch migration make this pathway of DNA hybrid dissociation much faster than dissociation via denaturation of the probe-target duplex, which requires overcoming a large energy barrier. In the case of double D-loop hybrids the situation is different. To form one base pair of the target-target duplex, it is necessary to denature two base pairs of probe-target duplexes. Thus, in the first stage, the process of double D-loop hybrid dissociation is not isoenergetic and is significantly shifted towards probe-target duplex reformation. However, if several DNA bases from the flanks of the probe-target duplexes open occasionally due to thermal fluctuations, then the probe-probe duplex can be nucleated. After nucleation of the probe-probe duplex, the dissociation of the double D-loop hybrid can proceed isoenergeticaly by migration of four-way DNA junction formed by target-target, probe-probe and two probe-target duplexes (see Discussion).

Here we investigated the effect of heterologous DNA inserts in the probe (i.e. inserts which can not interact with the target DNA) on double D-loop hybrid dissociation. On one hand inserts could accelerate double D-loop hybrid dissociation because they distort the probe-target duplex, and thus, facilitate its displacement. On the other hand, bulky heterologous inserts could produce an opposite effect by sterically constraining DNA four-way junction migration, especially if they form a complex with each other and "fasten" two probe-target duplexes together. To test which effect of the heterologous inserts predominates, we designed several different DNA probes with heterologous DNA inserts able to interact with each other via Watson-Crick base pairing or guanine quadruplex formation (Sundquist et al., (1989) Nature 342, 825–829).

Oligonucleotide Probes and Target DNA FIG. 9 shows DNAs used in this study. For Watson-Crick duplex forming heterologous inserts we chose the $d(GT)_n/d(CA)_n$-sequence which has a propensity to form left-handed Z-DNA under topological strain (Haniford et al., (1983) Nature 302, 632–634). This choice of insert sequences is explained in the Discussion. Probe oligonucleotides were purchased from the Midland Certified Reagent Company. Oligonucleotides were additionally purified by electrophoresis on 6% denaturing polyacrylamide gels containing 8 M urea. After elution from the gel in TE buffer (10 mM Tris HCl, 1 mM EDTA, pH 8) oligonucleotides were passed through microcentrifuge tube filters (PGC Scientific), gel filtrated through G-25 columns (Pharmacia), precipitated by ethanol and dissolved in DNA probe-storage buffer (10 mM Tris HCl, pH 7.5, 0.1 mM EDTA) to a final concentration of 1 ng/µl. Radiolabeling of oligonucleotides with $^{32}$P-γATP was performed with T4 polynucleotide kinase (Life Technologies, Gibco BRL). Oligonucleotides were purified on denaturing polyacrylamide gels as described above for unlabeled oligonucleotides except the precipitation step was omitted after the G-25 column.

Targeting reactions. pBluescript II SK(-) plasmid (Stratagene) was used as the DNA duplex target in all experiments and was purified using QlAfilter Plasmid Maxi Kit (QIAGEN). Purified plasmid was predominantly negatively supercoiled DNA.

The general scheme for forming probe-target hybrids is shown in FIG. 8. Complementary oligonucleotides (one of which was $^{32}$P-labeled) were coated with RecA protein in separate tubes. During RecA protein coating reactions 21 µl of each oligonucleotide (1 ng/µl) was mixed with 4.2 µl of coating buffer (100 mM Tris acetate, 500 mM Na acetate, 20 mM Mg acetate, 10 mM DTT, 50% glycerol; pH 7.5), 4.2 µl of 20 mM Mg acetate, and 6.3 µl of 16.2 mM ATPγS (Boehringer Manaheim). 7 µl of RecA protein solution (143 ng/µl, obtained from a concentrated RecA protein solution of 3 mg/ml (Boehringer Mannheim) by dilution with RecA-storage buffer (20 mM Tris-acetate, pH 7,5; 0.1 mM EDTA, 1 mM DTT, 50% glycerol)) was added to each oligonucleotide sample. The final concentrations of DNA and RecA in coating mixtures corresponded to 2.4 DNA bases per 1 RecA molecule. Mixtures were incubated at 37–38 C for 30 min. To initiate the targeting reaction, the target plasmid (4.9 µg) in 70 µl of 18 mM Mg acetate, 9 mM TrisHCl (pH 7.5), and 0.09 mM EDTA were added directly to the RecA coated labeled oligonucleotide. Unlabeled RecA coated oligonucleotide was then immediately added to the mixture. Samples were incubated for 1.5 hours at 37–38 C Next, 16 µl of 10%

SDS was added, the mixture was vortexed, incubated for 5 minutes at room temperature, and 170 µl of phenol-chloroform-isoamyl alcohol (25:24:1) (Life Technologies, Gibco BRL) was added, vortexed and centrifuged for 1 min. The aqueous fraction containing DNA, was removed into a fresh tube, and the same extraction procedure was repeated using chloroform. DNA was precipitated by the addition of 1/10 vol. of 3M NaOAc and 3 vol. of ethanol, air dried for 10–15 minutes and dissolved in 28 µl of DNA probe-storage buffer.

DNA Hybrid Stability 11 µl of DNA hybrid-containing solution was mixed with 25 µl of the probe-storage buffer (10 mM Tris HCl, pH 7.5; 0.1 mM EDTA), 4 µl of 10×REact 6 buffer (Gibco BRL; 1×REact 6 buffer is 50 mM Tris-HCl, 6 mM $MgCl_2$, 50 mM NaCl, 50 mM KCl; pH 7.4), and 3.2 µl Sca I restriction enzyme (Life Technologies, Gibco BRL). Restriction digestion was for 1.5–2 hours at 37–38° C. Next, 57 µl of 1×REact 6 buffer was added to the sample. Aliquots (24 µl) of the resulting mixture were placed in four thin-walled PCR tubes and incubated at 65° C. in a PCR machine with a heated lid to prevent evaporation (PTC-100, MJ Research). All tubes were simultaneously placed in the PCR machine, and the tubes were quickly removed to dry ice at defined time points. Next the samples were thawed and loaded onto a 1% agarose gel/TAE buffer (40 mM Tris Acetate, 1 mM EDTA, pH 8). Electrophoresis was performed at room temperature at ~1 V/cm for 20 hours. After electrophoresis DNA in gels was stained with ethidium bromide (1 µl/ml) in TAE and photographed under UV light with Polaroid film. In addition, the positions of all DNA bands observed under UV light after ethidium bromide staining were marked on transparent film to identify positions of DNA bands on autoradiograms. Next gels were dried on DE 81 anion exchange chromatography paper (Whatman) and exposed either to X-ray film (Kodak), or placed on a phosphorimager screen (Molecular Dynamics). Quantitative analysis of gels was performed using Image Quantsoftware (Molecular Dynamics).

Formation of Double D-loop DNA Hybrids. The kinetic stabilities were measured for double D-loop hybrids with different heterologous inserts within the linear target DNAs. The length of homology between the probe and the target DNAs was 62 bases. A negatively supercoiled DNA was used as an "intermediate" target because the linear DNA targeting efficiency with short probes is relatively low (Sena et al., (1993) Nature Genet. 3, 365–372; Jaysena et al., (1993) J. Molec. Biol. 230, 1015–1024). The general strategy of these experiments is shown in FIG. 10. First, RecA coated single-stranded DNA probes were hybridized with negatively supercoiled target DNA producing single and double D-loop hybrids. Hybrids were deproteinized by SDS and linearized by Sca I restriction digestion at a site away from the region of double D-loop formation (FIGS. 9 and 10). Both single and double D-loops formed in negatively supercoiled DNA are expected to be stable after deproteinization because they are stabilized by partial relaxation of superhelical tension in the target DNA (Beattie et al., (1977) J. Molec. Biol. 116, 825–839). However, only double D-loop hybrids are expected to survive linearization of the target (Sena et al., (1993) Nature Genet. 3, 365–372; Jaysena et al., (1993) J. Molec. Biol. 230, 1015–1024).

FIG. 11 shows DNA hybrids surviving linearization are indeed double-D-loops. In these experiments one of the probe strands, either $NI_W$ or $NI_C$ was radioactively labeled and monitored by autoradiography (right panel). The position of the target plasmid DNA was monitored by ethidium bromide staining (left panel). The probe co-migrated with supercoiled target DNA showing formation of the probe-target hybrid (FIG. 11, right panel, lanes 1, 3). As expected, in the case of supercoiled target DNA, hybrids were observed both in the presence or in the absence of the second probe strand. After linearization of the target plasmid by ScaI restriction enzyme, the hybrid co-migrating with the linear target DNA was observed only if both probe strands were present (FIG. 9, right panel, lane 2). Thus, in linear target DNA both probe strands are required for hybrid stabilization. This shows linearized hybrids contain double D-loops. Linearized double D-loop hybrids were tested for kinetic stability. Kinetic stabilities of different kinds of hybrids were estimated by the rates of their dissociation at an elevated temperature (65° C.).

Heterologous DNA Inserts Kinetically Stabilize Double D-loop Hybrids. FIG. 12A shows double D-loops formed by four different combinations of completely homologous probe strands ($NI_W$ and $NI_C$) and probe strands with quadruplex-forming heterologous inserts ($QI_W$ and $QI_C$). Probe-target hybrids formed by completely homologous probe strands ($NI_W$ and $NI_C$) (lanes 13–16) were barely detectable after 2 minutes of incubation at 65° C. (lane 14). In the case of quadruplex-forming probe strands ($QI_W$ and $QI_C$; FIG. 12A, lanes 1–4) the hybrids are observed after 20 minutes of incubation at 65° C. (FIG. 12A, lane 4). The quantitation by phosphorimaging in this and other similar experiments shows that the halftime of dissociation for the $QI_W/QI_C$ probe is about 5 minutes. In the case of "mixed" probe strands containing combinations $QI_W/NI_C$ (FIG. 12A, lanes 5–8) and $NI_W/QI_C$ (FIG. 12A, lane 9–12) "intermediate" kinetic stabilities were observed. These measurements show that the portion of these "half-heterologous" double D-loop hybrids which survived after 2 minutes of incubation are significantly larger (though still less than 50%) than in the case of completely homologous hybrids. These data show stabilization of double D-loop by heterologous inserts. The increased kinetic stability of the $QI_W/QI_C$ hybrid versus half-heterologous (QI/NI) hybrids suggests quadruplex formation within $QI_W/QI_C$ hybrid significantly contributes to kinetic stabilization of the probe-target hybrid. However, it does not exclude the possibility that this increased kinetic stability is caused by steric factors, rather than specific interactions between heterologous DNA inserts. To address this possibility we performed similar experiments with combinations of probes containing quadruplex forming heterologous inserts ($QI_W$ and $QI_C$) and Watson-Crick duplex forming inserts ($ZI_W$ and $ZI_C$). We tested all four possible combinations of probes, $QI_W/QI_C$, $QI_W/ZI_C$, $ZI_W/QI_C$, $ZI_W/ZI_C$. In the $QI_W/QI_C$ and the $ZI_W/ZI_C$ (matched) combinations heterologous inserts are able to form stable complexes (quadruplex and Watson-Crick duplex structures, respectively). In the $QI_W/ZI_C$ and the $ZI_W/QI_C$ (mixed) combinations, stable complex formation between heterologous inserts is not expected. If differences in stabilities of double D-loop hybrids were due to complex formation between heterologous inserts, then "matched" combinations of probes would tend to produce more stable hybrids than "mixed" ones. If the differences in stabilities were due to steric effects, "mixed" combinations should produce double D-loop hybrids of intermediate stability. FIG. 12B shows that the hybrids with "matched" combinations of probes ($QI_W/QI_C$, lanes 1–4 and $ZI_W/ZI_C$, lanes 13–16) dissociate more slowly (i.e. they are more kinetically stable) than hybrids with "mixed" combinations of probes ($QI_W/ZI_C$, lanes 5–8, and $ZI_W/QI_C$, lanes 9–12). FIG. 13 includes data for all combinations of probe strands used in these experiments and the schematics of proposed hybrid structures. The half-time of dissociation for double D-loops formed by "matched" combinations ($QI_W/QI_C$, and $ZI_W/ZI_C$ is about 5 and 10 minutes respectively, and is less then 2 minutes for the rest of the combinations. Thus, complex formation between heterologous inserts significantly contributes to double D-loop hybrid stabilization.

Discusssion. We observed heterologous inserts within the probe DNA kinetically stabilize double D-loop hybrids, despite the fact these inserts do not participate in the probe-target interactions and distort the probe-target hybrids. Without being bound by theory, to explain this observation we propose the following model of double D-loop hybrid dissociation.

Stabilizing effects of heterologous DNA inserts can be explained by a four-way junction migration model of double D-loop hybrid dissociation. FIGS. 14A–F shows a model for double D-loop dissociation via DNA four-way junction migration. During the four-way junction migration process the total number of base pairs does not change (i.e. this process is isoenergetic). The isoenergetic pathway of double D-loop dissociation via migration of four-way junctions appears more probable than dissociation via the energetically unfavorable denaturation of one or both probe-target duplexes.

However, the first stage of this pathway, the nucleation of the four-way junction, is preceded by the uncompensated denatured of several base pairs (FIGS. 14A–C). This creates an energetic barrier for nucleation, making this process relatively slow. A slow nucleation step can explain the kinetic stability of relatively short (<100 bp) double D-loops. This is in accordance with the fact that the slow initiation step dramatically impedes the duplex displacement via four-way junction branch migration (Panyutin et al. (1993) J. Molec. Biol. 230, 413–424). It is also possible that the within double D-loops the rate of four-way junction migration is slower than the migration rate for "cruciform-like" systems (Panyutin et al. (1994) Proc. Natl. Acad. Sci. USA 91, 2021–2025) because, within a double D-loop, four-way junction might be more prone to adopt a "folded" conformation (Lilley et al. (1993) Annul Rev. Biophys. Biomol. Struct. 22, 299–328) for which the rate of branch migration is slower (Panyutin et al. (1995) EMBO J. 14, 1819–1826).

During four-way junction migration DNA strands are spooled from one duplex regions to the other. This spooling is accompanied by the synchronized rotation of all duplex regions involved in the process (FIGS. 14D and 14F). Heterologous DNA inserts would constrain the rotation and consequently impede double D-loop hybrid dissociation. This effect would be stronger when both probe DNA strands contain heterologous DNA inserts which can interact with each other, but it also might be detectable in cases when bulky non-interacting DNA inserts create steric obstacles to rotation. We refer to the positive effects of heterologous inserts on double D-loop kinetic stability as an "and-rotational locks".

Our experiments demonstrate increased kinetic stabilities of double D-loops formed by probes with heterologous inserts compared double D-loops formed by completely homologous probes. These effects are more pronounced in cases of interacting heterologous inserts. These observations are in agreement with the anti-rotational lock hypothesis. The stabilizing effect of non-interacting heterologous insert is also apparent in certain cases (FIG. 12A). In our experiments we did not observe an apparent increases in stabilities of double D-loops with two non-interacting heterologous inserts versus one (i.e. QI/ZI versus QI/NI probe). This fact is also consistent with our model, because two non-interacting heterologous inserts should rotate in the same direction during branch migration, so they would not interfere with each other.

Structures of the complexes formed between heterologous inserts are shown in FIG. 15. Pairing between the homologous flanks of probe DNA strands and the target prevents an intertwining of heterologous inserts within the complex. Thus, within the complex, heterologous inserts from different probe strands must be topologically unlinked. This requirement is satisfied in the case of the quadruplex complexes, which result from interaction between two self-folded hairpins formed by each of the heterologous inserts (Sundquist et al. (1989) Nature 342, 825–829). In the case of Watson-Crick interactions between heterologous DNA inserts, this requirement is satisfied if the complex contains the same number of right- and left-handed helical turns. This DNA structure could be formed by $d(GT)_n/d(CA)_n$ inserts (probe ZI), since this sequence, in addition to right-handed B-conformation, can also adopt a left-handed Z-conformation (Haniford, D. B., & Pulleyblank, D. E. (1983) Nature 302, 632–634). Watson-Crick base pairing between complementary heterologous inserts within a topologically unlinked complex is also possible without Z-DNA formation, if the DNA region participating in the base pairing is less than one helical turn, or if left-handed turns are formed by DNA strands intertwining without base pairing. However in the case of DNA sequences with strong propensities to adopt Z-conformations, the complexes would be much more energetically favorable.

H-DNA-like triplexes (for review see Frank-Kamenetskii et al. (1995) Annul Rev. Biochem. 64, 65–95) are also examples of DNA structures which are topologically unlinked and consequently would have superior abilities to form "lock" complexes. We observed that the heterologous insert previously shown by Dayn et al. ((1992) Proc Natl. Acad Sci. USA 89, 11406–11410) to adopt H-DNA-like triplex structure causes strong kinetic stabilization of double D-loop DNA hybrids (data not shown).

Example 3

Blocking Transcription Using Locks

In these experiments a modified version of in vitro transcription assay described by Golub et al., (1992, 1993, supra) was used. Briefly, double-stranded DNA fragments having about 300 bp of homology (including T7 promoter) with a pBluescript II SK(−) were obtained by PCR either from pBluescript II SK(−) or pTL plasmid (pTL plasmid was derived from pBluescript II SK(−) by inserting the triplex forming sequence, 5-GGGTGGTGGGTGGGGTATTAGGGGAGGGAGGA GG<u>G</u>-3 (SEQ ID NO:17) (Dayn et al., 1992, supra) into the HindIII/EcoRI site; FIG. 16). The probes obtained from pTL plasmid were designed to form a triplex lock when targeted to pBluescript II SK(−). In addition, probes shown in FIGS. 9A–C also are used.

To obtain css probes, the PCR fragments were, purified, denatured, and coated with RecA as above. The targeting reaction between the css probes and pBluescript II SK(−) (linearized by ScaI) are allowed to run for 1.5 hours. T7 RNA polymerase and NTP monomers (including radioactive labeled CTP), are added and appropriate transcriptional buffer and cofactors were added to the targeting mixture. After 1 hour of transcription the samples were treated with SDS or proteinase K and loaded on a denaturing gel. The products of transcription were monitor by phosphorimaging.

Both probes with and without triplex locks inhibited transcription nearly completely (only 0.6% of control transcript remains in the case of TL-probe, and 1.9% in the case of completely homologous probe). This experiment shows that the probe with heterologous insert is at least as efficient as the completely homologous probes. However, the probes used in this experiment were not deproteinized prior to transcription. Based on the results of Examples 1 and 2, repeating this procedure with deproteinized hybrids, the D-loops with triplex or quadruplex anchoring locks are superior in preventing transcription.

Without being bound by theory, locked double D-loops block DNA copying either via structural distortion or copying enzyme recognition sites, or by constraining copying enzyme movement along the target DNA in a deproteinized state.

Example 4

Blocking Intracellular Transcription Using Locks

To inhibit gene expression by hybrid arrest of transcription in cells in culture. Nucleoprotein filaments that form duplex, triplex, and quadruplex locks are used to target key viral promotor or gene coding sequences in vector constructs that encode a real time reporter gene under the control of the CMV viral promoter. The green fluorescent protein (GFP) reporter gene is employed to rapidly assay gene expression. The GFP gene, from the jellyfish Aequorea victoria, has been used extensively as a real time reporter of gene expression in a vast array of cells, including bacteria, yeast, Drosophila, mice, human, and many other mammalian and plant cell lines. Detection of gene expression is non-invasive because the GFP protein emits bright green light (507 nm) upon simple exposure to UV or blue light (488 nm) without any requirement for substrates. Several GFP constructs are used. These constructs have GFP open reading frame under the control of the human cytomegalovirus (CMV) promoter (pEGFP, Clontech) or the SV40 promoter (pSPORT-GFP, derived from pSPORT, GIBCO-BRL, Gaithersburg, Md.). Other similar vector derivatives encoding a red-shifted variant of wild type GFP under the control of the CMV promoter or SV40 promotor, which have been optimized for significantly higher expression and brighter fluorescence for real time gene expression studies in cells (Takada et al., 1997) also are used. This vector backbone also contains a SV40 origin of replication in mammalian cells and expresses the SV40 T-antigen. A neomycin resistance cassette ($neo^r$), consisting of the SV40 early promoter of transcription, the neomycin/kanamycin resistance gene of Tn5, and polyadenylation signals from the Herpes simplex virus thymidine kinase gene, allows stably transfected eukaryotic cells to be selected using G418 selection.

Inhibition of transcription by RecA nucleoprotein filaments is demonstrated using oligonucleotides that target GFP including the promoter region (nucleotides 1–569 of pEFGP). The activity of RecA coated probes is pre-tested and validated in targeting assays in vitro as described above. The formation of multistranded hybrids is monitored by band shift assays. For studying the effects of nucleoprotein filaments to block transcription in intracellularly, pre-formed hybrids are formed and delivered into living cultured cells by either lipofection (DOTAP, Boehringer Mannheim) or electroporation. Expression of green flourescence protein inside the cell is monitored by confocal laser scanning or fluorescence microscopy. Additional tests of GFP gene expression include measurements of GFP mRNA levels by Northern analysis and PCR of GFP cDNA.

In addition, recombinase coated targeting biotin-labelled polynucleotides (filaments) are delivered into cells previously transfected with the vector target DNA and the formation of probe-target hybrids inside the transfected cells is monitored by reduction in GFP expression as described above. Nucleoprotein filaments are formulated with RecA, FECO, or NLS-FECO recombinase proteins. The fate of the filaments inside the cells is monitored using antibodies directed against RecA protein and with commercial anti-biotin antibodies.

Example 5

Enhanced Homologous Recombination (EHR) Inhibition of Viral Gene Function

Nucleoprotein filaments containing heterologous anchor sequences are used to introduce modifications in a viral vector gene and disrupt gene functions in transfected cells in culture. We have previously demonstrated that probe-target hybrid structures are very active in recombination in living cells. Hybrids with heterologies from 3 to 59 bases enhance recombination by several orders of magnitude in bacteria, plant, animal cells, and living mice. This results in targeted homologous recombinations in about 5–40% of target molecules, without any requirement for drug selection.

To compare the efficiency of double D-loop and duplex heterology-clamped double D-loop probes to hybridize and homologously recombine into selected reporter gene DNA sequences in transfected cells, DNA probes to both the pEGFP (Clontech) and pSPORT-GFP (derived from pSPORT, GIBCO-BRL) target sequences are synthesized to include the translation stop codons (TAA and ATT), translation frame shifts, or viral transcription arrest sequences which cause dysfunctional expression of GFP. The relative efficiencies of these probes to form stable hybrids with viral vector target sequences in solution prior to targeting sequences in cells in culture is compared as described in the previous examples.

Hybrid complexes are transfected by electroporation or with DOTAP (Boehringer Mannheim) or DLS (Promega and Sigma)-mediated lipofection (Thierry et al., 1995) into mammalian cells (e.g., BALB mouse cell lines, ATCC, Rockville, Md.). As described above, inhibition of GFP protein gene expression is monitored in these transfected cells by confocal laser scanning or standard fluorescence microscopes. The relative levels of full-length or truncated GFP RNA transcripts is analyzed by Northern analysis or by RT-PCR of GFP transcripts. At various times following transfection, GFP gene expression is directly monitored by microscopic visualization. In addition, DNA is harvested to determine to identify homologous recombination events, as monitored by direct DNA sequence analyses.

Nucleoprotein filaments also are transfected into cells that have been pre-loaded with GFP containing viral vector targets. Following transfection the vector DNA exists as chromatin in the cells. Cells are transfected with the vectors and nucleoprotein filaments added at various times post-inoculation.

Example 6

Inhibition of a Viral Pathogen in a Mouse Model

Systemic lipofection is used to inoculate nucleoprotein filaments into the tail vein of mice to target episomal viral vectors and inhibit viral gene expression in mice in vivo.

Effects of Nucleoprotein Filament Mediated Probe-Target Hybrids on Expression of a Simulated Viral Pathogen Test Gene. Thierry et al., (PNAS USA 92:9742–9746 (1995)) have utilized a system to measure the efficacy of systemic viral vector gene transfer in mice in vivo. They have successfully used the human papovavirus (BKV) derived episomal vector (pBKd1CMV-luc) to systemically deliver luciferase reporter genes into mice via tail vein injection of defined DLS liposome:BKV DNA vector complexes. They successfully demonstrated long term expression of the BKV DNA vectored luciferase reporter gene into lung, spleen and liver using defined liposome formulations consisting of a 1:1 mixture of dioctadecylamidoglyclspermidine (Promega) and dioleoyl phosphatidylethanolamine (Sigma), commonly known as DLS liposomes. Here, the DLS-BKV luciferase episomal vector system is used in adult mice to quantitate the level of gene inhibition in vivo using targeting polynucleotides comprising targeted sequence locks.

GFP containing BKV and other vectors in the mouse model system, and protocols for in vivo mouse GFP measurements are performed according to the methods of Takada et al. (Nature Biotechnol. 15:458–461 (1997)) and Clonetech (Palo Alto, Calif.). Codon usage of GFP in mammals has been optimized and GFP has been used in vivo as a real-time reporter gene to monitor its localization within both living cells and in animals (Takada et al. Nature Biotechnol. 15:458–461 (1997) and Clonetech, Palo Alto, Calif.). The combination of the viral CMV transcriptional enhancer and the transcriptional promoter in the vectors successfully drives expression of normal or modified GFP in the vector introduced to embryonic and adult mouse or human cells. The use of the confocal laser scanning microscope allows easy and rapid identification of normal and modified GFP-expressing cells and tissues (Takada et al, 1997).

Self-Assembling Liposomes and VP1 Pseudocapsids as Methods of Systemic Delivery of Nucleoprotein Filaments in Mice in vivo. The biological effects of introducing nucleoprotein filaments formulated with liposomes in an in vivo system employs DOTAP (Boehringer-Mannheim) and DLS (Thierry et al, 1995) and filament formulations which self-encapsulate in mouse polyoma virus (VP1) pseudocapsids. Mouse polyoma (virion protein VP1) pseudocapsids have been successfully used to self-assemble and to experimentally transfer RecA-coated nucleoprotein filaments into rodent and human cells and into mice (Forstova et al, Human Gene Therapy 6:2978–2306 (1995); Hunger-Bertling et al, Molecular and Cellular Biology 92:107–116 (1990); Bertling, Biotechnology and Applied Biochemistry (1991)).

Mouse polyoma virus has a very broad host range which also includes human cells. Bertling and coworkers have examined the use of polyoma virus pseudocapsids to deliver RecA protein coated nucleoprotein filaments. They observed that RecA coated ssDNA formulated as nucleoprotein filaments are more efficiently self assembled into capsids, in comparison to ssDNA not coated with RecA protein (Bertling, 1990). BKV, a human polyomavirus, infects most of the world's population as evidenced by serological studies.

Comparisons of the in vivo Activities of Nucleoprotein Filament Formulations delivered Systemically. The human polyomavirus BK (BKV) has three functionally distinct regions: coding sequences for the two early genes (large T- and small t-antigens), coding sequences for four late genes (including the virion capsid proteins) which are separated by non-coding control regions that contain the BKV origin of DNA replication and the promoter/enhancer with cis-acting regulators of early and late transcription. These non-coding control regions appear to vary significantly among human BKV isolates. This is apparently due to naturally occurring and spontaneous deletions, duplications and arrangements (for review see Moens et al., Virus Genes 10:261–275 (1995)). Our vector target BKV DNA contains only a fragment of the BKV viral early regions, the origin of DNA replication, and the large T-antigen. The late viral capsid proteins are deleted to remove expression of these potentially immunogenic proteins (Thierry et al., 1995).

As described above, pBKd1CMV-luc, a correspoding vector that expresses GFP, and pEGFP which express the respective reporter genes under control of the strong viral (CMV) transcriptional promoter, the polyadenylation signal and transcriptional termination sequences of SV40 virus are used. The targeted sequences of these constructs are the CMV promoter sequences and the coding sequences of the test reporter genes, GFP or luciferase.

Pre-formed probe-target hybrids formulated with liposomes are directly introduced by injection into the tail veins of 4–6 week old female BALB/c mice. Vectors are re-isolated from animals and analyzed as described above to identify recombinogenic events between the target nucleic acid vector and the targeting polynucleotides.

Nucleoprotein filaments are complexed with DLS-liposomes or polyoma virus VP1 capsids are characterized as described above and injected in mice that have been previously injected with a vector encoding a reporter gene. No significant differences in luciferase gene expression has been reported with pBKd1CMV-luc vector after subcutaneous, intraperitoneal, and intravenous routes of administration (Thierry et al, 1995). Furthermore, in mice treated with 75 ng of vector, luciferase gene expression is maximal between 6 and 15 days in various tissue samples.

After nucleoprotein filaments are introduced into mice, tissues are collected, quickly frozen on dry ice, and stored at −70° C. until examined. Tissues to be examined include the lung, heart, muscle and spleen. Tissues are examined as described by Thierry et al, 1995 to quantitate the level of vector expression as monitored by GFP or luciferase expression, respectively.

Example 7

DNA Branch Migration in the Presence of a Slow Reversible Initiation Step

Branched DNA structures include structures comprising several DNA regions connected by three- or four-way DNA junctions. Branched DNA can be an intermediate in DNA replication and recombination in living organisms and in sequence-specific DNA targeting in vitro. Usually branched DNA structures are metastable and irreversibly dissociate to non-branched products via a DNA strand exchange process commonly known as DNA branch migration. The key parameter in the DNA dissociation process is its characteristic time, which depends on the length of the dissociating DNA structure. The presence of a slow reversible initiation step, which precedes DNA branch migration, can alter to almost linear dependence, the "classic" quadratic dependence of the dissociation time on the length of the dissociating DNA structure. This can be applied to dissociation of Y-like DNA structures and double D-loop DNA hybrids, which are DNA structures similar to replication bubbles. In addition, the slow initiation step can increase the effect of DNA sequence heterologies within the structure on its kinetic stability. Applications exist for manipulations with branched DNA structures are discussed.

DNA replication and homologous recombination proceed via formation of branched DNA structures in which DNA strands switch from one duplex region to the other, or from single-stranded state to double-stranded state, forming various types of DNA junctions (Kornberg. *DNA Replication*, W.H. Freeman & Co., San Francisco, 1980; Radding, in *Genetic Recombination*, eds Kucherlapati & Smith, Washington, American Society for Microbiology, 193–320 (1988)). Usually branched DNA structures are metastable and irreversibly dissociate to non-branched products via strand exchange process commonly known as DNA branch migration (for review see (Hsieh et al., *Nucleic Acids and Molecular Biology*, 9:42–65 (1995)).

Among the DNA structures which dissociate via branch migration, it is important to distinguish between two types. In the first type of DNA structures, the migrating DNA junction is irreversibly formed from the very beginning. For this type of DNA structure, branch migration can be described as a random walk process with a reflecting barrier at the initial position, which corresponds to full length of the structure, and an absorbing barrier, which corresponds to complete dissociation of the structure. If the probabilities of the back and forward steps of DNA branch migration are the same, probability theory predicts a quadratic dependence of the characteristic dissociation time on the length of the structure (Feller. *An introduction to Probability theory and Its Application*, Wiley, New York (1957)). This prediction was confirmed for single D-loops in nicked DNA (Beftie et al., J. Molec. Biol. 116:825–839 (1977)) and for irreversibly nucleated Holliday junction migration (Panyutin et a., Proc. Natl. Acad. Sci. USA 91:2021–2025 (1994)). In the other type of DNA structure, formation of the migrating junction is preceded by a slow and reversible nucleation step. Examples of both types of DNA structures, the irreversibly nucleated Holliday structure and Y-like structure, are shown in FIGS. 17A and 17B, respectively.

Another example of a structure where dissociation appears to proceed via a slow initiation step is the double D-loop (Sena et al., Nature Genet. 3:354–372 (1993); Jayasena et al., J. Molec. Biol. 230:413–424 (1993)) (FIG. 18A). The dissociation time for this second type of structure is expected to be longer than for the first type of structure with the same length. The increased kinetic stability of the second type of structure was demonstrated for both Y-like structures (Panyutin et al., J. Molec. Biol. 230–412–424 (1993)) and for double D-loops (Sena et al., 1993; Jayasena et al., 1993). However, to the best of our knowledge, the length dependence of the dissociation time for the second type of structures has not been analyzed.

Knowing this dependence is important to understand possible biological applications of these structures. For example, double D-loops are being used in sequence targeted gene modifications, gene mapping and gene isolation (for review see Pati et al., in *Molecular Biology of Cancer*, ed J. Bertino (Academic Press, San Diego), Volume III, 1601–1625 (1997)). In addition, both double D-loops (usually called "bulges" in this context) and Y-like DNA structures can be obtained as replication intermediates and electrophoretic separation of these intermediates is used to monitor the dynamics of DNA replication (for review see Friedman et al., Methods in Enzymology 262:613–627 (1983)).

For all these applications, the characteristic dissociation time of the structure must be longer than the time of the experiment. Since the dissociation time for any structure decreases with decreasing the length of the structure, the question arises, what is the minimal length of the structure which can be used in a given experiment under given conditions.

Here we derive and analyze equations which allow estimations of the dissociation times for the Y-like DNA structures and double D-loops of varying lengths.

The dissociation of branched DNA structures is based on the assumption that during the dissociation the number of simultaneously denatured DNA base pairs must be as small as possible. This is because DNA denaturation process requires overcoming a large energetic barrier. The dissociation pathway which satisfies this requirement is the DNA branch migration process, in which at each step denaturation of one DNA base pair is compensated by a newly formed DNA base pair. Thus each step of the process is isoenergetic unless the structure occurs within the supercoiled DNA. (The supercoiled DNA is considered in the last part of this section.)

Dissociation of Y-like DNA Structures. An example of the isoenergetic branch migration process, with migration of the four-way DNA junction, is shown in FIG. 17A. For initiation of a similar branch-migration process within Y-like DNA structures, the nucleation of an additional duplex region is required. This nucleation is preceded by the uncompensated denaturation of several DNA base pairs (FIG. 17B), which provides a large energetic barrier for the initiation step, making this step much slower than the isoenergetic elongation step of branch migration (Panyutin et al., 1993). Accordingly, (see below), about 8 base pairs need to be denatured to provide nucleation.

Let us consider the dissociation pathway for Y-like DNA structure (FIG. 17B). The branch migration process is initiated by the formation of a short double-stranded "nucleus". Note that at least some of base pairs within this nucleus are distorted near to vicinity of the four-way junction. The minimal number of bases required for nucleus formation is $I_n$ and the double-stranded DNA "branch" containing less than $I_n$ base pairs is unstable. Thus, the total number of steps before irreversible dissociation of the structure which contains $L_0$ base pairs is $L=L_0-2I_n+2$. Since we mainly consider DNA structures significantly longer than In, for simplicity we refer to L as the length of the structure. We treat the dissociation of the DNA structure as a "gambler's ruin" problem (Feller 1957).

Let T(x) be the average dissociation time for the structure with the junction initially localized at a position x from the left. The position is measured in the number of steps as follows: x=0 corresponds to the initial structure (FIG. 17A, top), x=1 corresponds to the "nucleus" $I_n$, and for x>1 one step corresponds to one base pair. At position x=L the dissociation process is completed. For any position x (excluding 0), the probability to make a step in either direction is ½. Thus, $$T(x)=[T(x-1)+T(x+1)]/2+\tau_1 \qquad [1]$$

where $\tau_1$ is the step time for four-way DNA junction migration.

The edge conditions are as follows:

$$T(0)=T(1)+\tau_n \qquad [2]$$

where $\tau_n$ is the time of nucleation ($\tau_n > \tau_1$) and $$T(L)=0 \text{ ("absorption")}. \qquad [3]$$

The solution of the system (Eqs. 1, 2, 3) is $$T(x)=(\tau_n-\tau_1)(L-x)+\tau_1(L^2-X^2) \qquad [4]$$

An experimentally observed average dissociation time $\tau$ usually corresponds to dissociation process which starts from "zero" position $$\tau=T(0)=(\tau_n-\tau_1)L+\tau_1 L^2 \qquad [5a]$$

The case $\tau_n=\tau_1$ corresponds to irreversible nucleation (FIG. 17A).

In this case $$\tau=\tau_1 L^2 \qquad [5b]$$

It is seen that $\tau_n \neq \tau_1$ a linear term is present. This term appears because the number of random walk steps before "absorption" grows quadratically with the distance between the absorbing (x=L) and reflecting (x=0) barriers. Consequently, the number of returns to the reflecting barrier before the absorption grows linearly with the distance and each return gives an additional "penalty time" $\tau_n - \tau_1$. We are interested in the case when $\tau_n > \tau_1$, and $$\tau \approx \tau_n L + \tau_1 L^2 \qquad [5c]$$

Using Equation 5c one can estimate up to which length L the linear term predominates over the quadratic term. For this, we use data obtained by Panyutin and Hsieh (J. Molec. Biol. 230:413–424 (1994)) at 37° C., neutral pH and 50 mM $Na^{30}$ ion concentration. The dissociation time for the Y-like structure which contains 40 bp is about $10^4$ seconds under these conditions. The step time $\tau_1$ for branch migration under the same conditions is less than 0.05 seconds, thus, the quadratic term in Eq. 5a was less than 80 seconds, which is less than one percent of the total dissociation time. Thus, the main contribution to the dissociation time is from the linear term, and the nucleation time $\tau_n$ can be estimated as $\tau_n=10^4/L$ (seconds)$\approx$300 seconds and the ratio $\tau_n/\tau_1$ is greater than $6 \times 10^3$. (Here we assume that for the structure which contains 40 bp, the "effective" length L is in between 20 and 40 bp.) From Eq. 5c it is seen that this ratio corresponds to the length (bp) below which the linear term is dominated over the quadratic term. The step time $\tau_1$ can vary from $3\times10^{-4}$ s to $3\times10^{-1}$ s depending on magnesium ion concentration in the reaction (Panyutin and Hsieh (1993)). This dramatic magnesium dependence of the step time is presumably due to the effect of magnesium ions on the structure of the Holliday junction (for review see Hsieh, (1995)). According ti the model (FIG. 17B), the initiation step proceeds via denaturation of several DNA base pairs, which then participate in the nucleation of the four-way DNA junction. Magnesium ions stabilize DNA duplexes. Thus, magnesium ions constrain the denaturation of each DNA base pair which participates in the nucleation of the four-way DNA junctions. This decelerates the initiation step. On the other hand, however, the number of DNA base pairs, which is required for stable nucleation of the DNA four-way junction would be smaller in the presence of magnesium ions. Thus, the total number of DNA base pairs, which is required to be denatured to provide the initiation, also would be smaller in the presence of magnesium ions. This would accelerate the initiation. Thus, in principal, magnesium ions could either accelerate, or decelerate the initiation step time. In the case where the initiation step time weakly depends on magnesium ions concentration, the ratio $\tau_n/\tau_1$ can vary from $10^3$ to $10^6$. In our examples, we use $10^4$ as the value of this ratio, which is close to estimation obtained from the data of Panyutin and Hsieh (1993).

Using the value of $\tau_n$, one can determine the number of base pairs $I_n$ which are required to be denatured in order to provide nucleation. If we assume that the nucleation time is equivalent to the time required for non-compensated denaturation of $I_n$ bp, then according to Anshelevich et al., Biopolymers 23:39–58 (1984):

$$\tau_n = \tau_0 \exp[I_n \Delta G/(RT_a)] = \tau_0 \exp[I_n \Delta H(T_m - T_a)/(RT_a T_m)] \quad [6]$$

where $\tau_o \approx 10^{-6}$ s is the characteristic time of the opening of one DNA base pair (see Wetmur. Critical Review in Biochemistry and Molecular Biology 23(¾), 227–259 (1991) and references therein), $\Delta G$ is the free energy of melting of one base pair at a given ambient absolute temperature $T_a$ (usually is about 310° K), $T_m$ is the melting temperature for an infinitely long DNA duplex at given ionic conditions (usually about 353° K (Wetmur 1991), $\Delta H \approx 8$ kcal/mol (Wetmur 1991) is the melting enthalpy for one DNA base pair, and R is the universal gas constant. Substituting numerical values in Eq. 6, we conclude that $I_n = 8$ base pairs. Note that, in reality, the initiation energetic threshold in addition to the energy of opening of $I_n$ base pairs might also include other components. For example, an unfavorable decrease in entropy due to a decrease in the DNA branches' motility, which would accompany the nucleation of the four-way DNA junction.

Effect of Mismatched Bases on the Y-like DNA Structure Dissociation.

Another interesting effect of the slow initiation step is the increased sensitivity of the dissociation time to the presence of mismatched (i.e. non-complementary) base pairs in the initial branched DNA structure (FIG. 17C). If the products of dissociation contain only complementary base pairs, then the presence of a mismatch in the initial structure will accelerate dissociation, because the displacement of the mismatched base pair by the matched base pair is energetically favorable and consequently the probability of the step to the right (i.e. toward dissociation) at the mismatched position is greater than the probability of the step to the left (Panyutin 1993; Robinson et al., Biophys. J. 51:611–626 (1987); Biswas et al., J. Molec. Biol. 279:795–806 (1998). However, in the presence of a slow initiation step, this acceleration can be significantly more pronounced. To illustrate this in the case of a DNA mismatch ("supermismatch") which is so energetically unfavorable in comparison with a matched base pair, that its displacement is irreversible (i.e. it is equivalent to the absorbing barrier if the junction is localized at the left side from it, and it is equivalent to the reflecting barrier if the junction is localized at the right side from it). Consequently, when the position of this "supermismatch" is m, the average time of overcoming the interval [0, L] is the sum of the average times of overcoming the intervals [0, m) and [m, L]. In the absence of a slow reversible initiation step this sum is $$\tau(_m) = \tau_1[m^2 + (L-m)^2] \quad [7]$$

The minimal value of this function is $\tau_1 \approx L^2/2$. Thus, in the absence of slow reversible nucleation step the maximal acceleration of the dissociation by mismatch is only two times (compare to Eq. 5b). In the presence of slow reversible nucleation step:

$$\tau = (\tau_n - \tau_1)m + \tau_1 m^2 + \tau_1 (L-m)^2 \quad [8]$$

If $\tau_n/\tau_1 = 104$ bp, L=100 bp, and m=2, then the "supermismatch" accelerates dissociation by about 30 times. This greater effect of the "supermismatch" in the presence of a slow reversible nucleation step is due to the fact that the "supermismatch" prevents the return of the structure to the initial position, thus making the nucleation step irreversible. Qualitatively this effect of mismatch was described by Panyutin and Hsieh (1993). The general case for dissociation of a Y-like DNA structure with a mismatch is analyzed in Appendix 1.

Dissociation of Double D-loop Hybrid DNA Structures within Non-Supercoiled DNA Targets. The main difference between Y-like DNA structures (FIG. 17B) and double D-loop DNA hybrids (FIG. 18A–D) is that within a double D-loop, two four-way DNA junctions can be formed. In general, the presence of two junctions makes the rigorous calculation of the dissociation time more complicated (Anshelevich et al., 1984). However, we show that topological constrains within double D-loops "synchronize" the movement of two four-way DNA junctions, causing them to migrate preferably in the same direction. The structure with two four-way DNA junctions (FIG. 18C) was analyzed. As long as both probe-probe and target-target flanking duplex regions remain base paired, the probe and the target strands form two linked closed contours. The number of links between the contours formed by the probe and the target DNA strands must remain the same during any movements of the four-way junction, until one of the junctions disappears. In the normal state usual B-form DNA has 10.5 base pairs per one helical turn (in this state the number of helical turns is equivalent to the number of links between contours) and even a small deviation from this number induces a strong deformational force called "superhelical" stress (for review see Vologodskii, Topology and Physics of Circular DNA, CRC Press, Inc. (1992)) which tends to return to the normal the number of base pairs per turn. The step made by one junction in one direction, changes the number of base pairs within the probe-target DNA duplexes, while the number of links between the contours formed by the probe and the target DNA strands will remain the same. Thus this step induces superhelical stress within the probe-target duplexes which will in turn facilitate movement of the other junction in the same direction, and, thus, relax the superhelical stress. As a result, the DNA junctions move in the same direction. Thus, the distance between the junctions would remain the same during their movement. The expected average fluctuation δr of the distance r between junctions is about $(r/10)^{1/2}$ (see below Appendix 2). In our model we neglect the fluctuations of r during the movement.

We analyzed double D-loop DNA structures with homogeneous DNA sequences. Thus, the junctions nucleated from the left and from the right flank are equivalent. Since the structure is symmetrical, it does not matter which junction is left or right. Thus, we may adopt the convention that the four-way junction at the left flank always nucleates first. The position of the left four-way DNA junction within single-nucleated (sn) double D-loop (FIG. 18B) is characterized by the distance x from the left flank (in a similar way as for Y-like DNA structures). Single-nucleated structures can produce double-nucleated (dn) structures (FIG. 18C) by the second nucleation at the right flank. Since within our approximation the distance between junctions within the double-nucleated structure remains constant, until one of the junctions disappears, the distance r between the junctions is determined by the coordinate $X_{dn} = z$ of the first (left) junction at the moment when the second (right) junction was nucleated (r=L⁻z). Thus, the double-nucleated structure can be completely described by the current coordinate of the left junction x and the parameter z. Using parameter z instead of r is more convenient for the further analysis.

To calculate the average dissociation time for a double D-loop, we introduced two functions, $T_{sn}(x)$ and $T_{dn}(x, z)$, which are the average dissociation times for the structure which initially was in the single-nucleated state, with the junction localized at position x from the left, and the structure which initially was in the double-nucleated state with the left junction localized at position x, and with the right junction which was nucleated when the left junction was at position z. The non-nucleated state we define as $T_{sn}(0)$.

Since the double-nucleated state cannot be changed to the single-nucleated state before one of the junctions reaches the edge position, the synchronized movement of the junctions within a double-nucleated structure can be approximated by the isoenergetic random walk process which is described by the recurrent equation similar to Eq. 1:

$$T_{dn}(x, z)=[T_{dn}(x-1, z)+T_{dn}(x+1, z)]/2+\tau_2 \qquad [9]$$

where $\tau_2$ is the apparent step time for the synchronized movement of the junctions. When the left junction reaches position x=z, the next step to the right leads to the disappearance of the right junction and the formation of a single-nucleated structure with the left junction position at z+1. When the left junction reaches position x=1, the next step to the left leads to the disappearance of the left junction and the formation of a single-nucleated structure with the right junction position L−(z+1), which, since we are considering homogeneous sequences, is equivalent to the single-nucleated structure with the left junction at position z+1. Thus, the edge conditions are $$T_{dn}(z, z)=[T_{dn}(z-1, z)+T_{sn}(z+1)]/2+\tau_2 \qquad [10]$$

$$T_{dn}(1, z)=[T_{dn}(2, z)+T_{sn}(z+1)]/2+\tau_2. \qquad [11]$$

The solution of the system (Eqs. 9, 10, 11) is $$T_{dn}(x, z)=T_{sn}(z+1)+\tau_2 x(z+1-x). \qquad [12]$$

To obtain a recurrent equation for a single-nucleation state, it is convenient to introduce the rate constant for nucleation, $k_n=1/\tau_n$, and the rate constant for the isoenergetic step in either direction, $k_1=1/(2\tau_1)$. The single-nucleated state can be converted to the double-nucleated state at any position of the first junction. The probability of the second nucleation during the infinitely small time interval, $\Delta t$, is $k_n \Delta t$, the probability to make the step in either direction during the same time interval, $\Delta t$, is $k_n \Delta t$, the probability make the step in either direction during the same time interval is $k_1 \Delta t$, and the probability to remain in the same state and position is $1-k_n \Delta t-2k_1 \Delta t$. The probability that during the same time interval $\Delta t$ both the branch migration step and the nucleation occur is $\sim(\Delta t)^2$, which can be omitted for an infinitely small $\Delta t$. Thus, $$T_{sn}(x)=k_1\Delta t[T_{sn}(x-1)+T_{sn}(x+1)]+k_n\Delta t T_{dn}(x, x)+$$

$$+(1-2k_1\Delta t-k_n\Delta t)T_{sn}(x)+\Delta t \qquad [13a]$$

which gives recurrent equation $$T_{sn}(x)=[k_1/(2k_1+k_n)][T_{sn}(x-1)+T_{sn}(x+1)]+$$

$$+[k_n/(2k_1+k_n)]T_{dn}(x, x)+1/(2k_1+k_n) \qquad [13b]$$

From Eq. 12

$$T_{dn}(x, x)=T_{sn}(x+1)+\tau_2 x \qquad [14]$$

Substituting $T_{dn}(x, x)$ in Eq. 13b by Eq. 14 we obtain $$T_{sn}(x)=[k_1/(2k_1+k_n)]T_{sn}(x-1)+[(k_1+k_n)/(2k_1+k_n)]T_{sn}(x+1)+[k_n\tau_2/(2k_1+k_n)]x+$$

$$+1/(2k_1+k_n) \qquad [15]$$

The edge conditions for $T_{sn}(x)$ are similar to the edge conditions for the Y-structure (Eqs. 2, 3), except, since we postulate that the first formed junction is the left one by definition (and in reality it can be nucleated from either of ends), the nucleation constant in the edge condition must be multiplied by 2:

$$T_{sn}(0)=T_{sn}(1)+1/(2k_n) \qquad [16]$$

$$T_{sn}(L)=0 \qquad [17]$$

The solution of this system (Eqs. 15, 16, 17) can be found in the form $$T_{sn}(x)=AB^x+C_0+C_1 x+C_2 x^2 \qquad [18]$$

where A, B, $C_0$, $C_1$, and $C_2$ are constants.

The average dissociation time which corresponds to the dissociation from the "less structurally distorted" non-nucleated state (which most likely would be the initial state in an experiment) is $$\tau=T_{sn}(0) \qquad [19]$$

In the final equation for $\tau$ we use dimensionless parameters $$v=k_n/(2k_1)=\tau_1/\tau_n \qquad [20]$$

$$\phi=\tau_2/\tau_1=2k_1\tau_2 \qquad [21]$$

Parameter $v$ is <1. Parameter $\phi$ is presumably $\geq 1$, because in reality the movement of the DNA four-way junctions within a double-nucleated double D-loop is unlikely to be perfectly synchronized. Consequently, at the beginning of each "effective step" some superhelical stress is generated, which impedes the movement.

The dependence of the experimentally observable average dissociation time $\tau$ on the length L of the double D-loop DNA structure, obtained from Eqs. 16–19, is conveniently presented in the form:

$$\tau(L)/\tau_1=(\phi-1)[(1+2v)/4v^2][1-(1+2v)^{-L}-2vL/(1+2v)]+$$

$$+\phi(L-1)L/2+L/(2v) \qquad [22a]$$

At $\phi=1$, this equation is almost the same as for a Y-like DNA structure (Eq. 5c):

$$\tau(L)/\tau_1=(L-1)L/2+L/(2v)\approx L^2/2+L/(2v) \qquad [22b]$$

Thus, the dependence on length is predominantly linear if $L<(1/v)=\tau_n/\tau_1$ and predominantly quadratic if $L>(1/v)$. In Appendix 3 we prove that this is also the case for $\phi\neq 1$. Thus, the kinetic properties of Y-like DNA structures and double D-loops are similar.

Note that in the derivation of Eq. 22a we did not consider the special case of the second junction nucleation when the first junction is closer than $10+I_n$ bp to the second flank. In this case, the duplexes between junctions would contain less than one helical turn, i.e., the contours shown on FIG. 18C would be unlinked. Most probably, this unlinked structure would readily dissociate. Thus, if we neglect this pathway of dissociation we would obtain an overestimated value of the dissociation time. On the other hand, if we postulate that the structure always dissociates when the first junction approaches closer than $10+I_n$ bp to the second flank (which is equivalent to decreasing the apparent length of the structure by ten base pairs), then we would obtain an underestimated value of the dissociation time. Thus, the "true value" of the dissociation time is in between the value obtained from Eq. 22a for L and the value obtained from Eq. 22a for L−10.

In *E. coli* RecA protein mediated DNA targeting reactions it often occurs that both probe DNA strands, as well as both target DNA strands are completely homologous to each other, but there is some DNA sequence heterology between the probe and the target. Let us analyze the effects of heterology between the probe and the target strands on the kinetic stability of double D-loops. If significant heterology is localized at one flank of the double D-loop, it would provide practically irreversible nucleation at this flank. In Appendix 4 we analyze the dissociation of a double D-loop with a fast irreversible nucleation of the probe-probe duplex at one of the flanks. For "short" double D-loops ($L<1/v$) the dissociation time for such structure is approximately $\tau_1 L^2$, which coincides with the "classic" formula for four-way DNA junction dissociation without a slow initiation step (Eq. 5b) and is about $1/(2vL)$ times faster than dissociation of the double D-loop of the same length without heterologies at the end (see Eqs. 22a, 22b). This occurs because for "short" double D-loops the possibility of formation of the double-nucleated state can be neglected, which makes irreversibly nucleated double D-loop similar to the "classic" structure in FIG. 17A. For "long" double D-loops ($L>1/v$) the dissociation time is about $\tau_1\phi L^2$, which is twice as slow as dissociation of the "long" double D-loop with the same length without heterologies at the flank. Thus, in contrast to "short" double D-loops, dissociation of "long" double D-loops is slightly decelerated, rather than accelerated, by DNA sequence heterology at the end. It occurs because in the case of irreversible nucleation of the four-way junction at one end, the probe-probe duplex can be displaced only from one end of the structure, thus the second nucleation (which occurs with a high probability if $L>1/v$) is "non-productive" for dissociation, and its only effect is in impeding the movement of the four-way DNA junctions within the structure (provided that $\phi>1$). If $\phi=1$, the second nucleation would not affect the dissociation of this structure.

The length dependences of the dissociation times (in double-logarithmic coordinates) for usual double D-loops with slow reversible (R) initiation step, and for double D-loops with irreversible (I) nucleation of the four-way junction at one end, are shown in FIG. 19A. FIG. 19B shows the derivatives $d(\log_{10}\tau)/d(\log_{10}L)$ of the curves from FIG. 19A. These derivatives can be interpreted as "apparent exponents" of the dissociation time length dependences for these two DNA structures. It is seen that for usual double D-loops this exponent switches from 1 (linear dependence) to 2 (quadratic dependence) in the vicinity of $L\approx 1/v$, while for double D-loops with irreversible nucleation of the four-way junction at one end, this exponent is always close to 2, and has a small maximum at $L\approx 1/v$, which corresponds to switching from $\tau\approx\tau_1 L^2$ to $\tau\approx\tau_1\phi L^2$.

If DNA sequence heterologies are localized either at both ends or in the middle, the effect is more complicated. For heterologies at both ends, the fraction of the DNA hybrid molecules in which the second nucleation did not occur would dissociate faster than completely homologous double D-loops, while the fraction of DNA hybrid molecules in which the second nucleation occurred would be kinetically trapped, because their dissociation requires energetically unfavorable opening of one of the flanking probe-probe DNA duplexes. Note that formation of double D-loop hybrids with DNA sequence heterologies at both ends is unlikely in the case of RecA protein mediated strand-exchange reactions which require DNA sequence homology at least at one end (see Radding et al., 1988 and references therein). An interesting situation occurs when DNA sequence heterology is in the middle of the probe-target duplexes. Small heterologies (for example, mismatches) in the middle of a double D-loop would accelerate double D-loop dissociation because after being passed by the four-way DNA junction they would prevent its return to the "zero" position. However, longer heterologies could impede dissociation by impeding the rotation (which accompany DNA branch migration) of the DNA duplexes comprising the four-way DNA junction (Belotserkovskii et al., Biochemistry 38:10785–10792 (1992)).

Effect of a Slow Initiation Step on D-loop Hybrids Dissociation within Supercoiled DNA Targets. Within supercoiled DNA targets, for example, plasmids and bacterial artificial chromosomes (BACs), the target DNA strands are topologically linked. Thus, a local unwinding of the target DNA caused by D-loop formation, induces compensatory conformational changes in the whole target DNA (for review see (Vologodskii. Topology and Physics of Circular DNA, CRC Press, Inc. (1992)). This makes DNA branch migration within supercoiled target DNA non-isoenergetic even in the case of complete homology between the probe and the target DNA sequences. Within negatively supercoiled DNA targets both single and double D-loops formation causes relaxation of superhelical stress (Beattie et al. J. Molec. Biol. 116:825–839 (1977)). This relaxation stabilizes D-loops making their displacement energetically unfavorable. In the case of supercoiled DNA targets it is important to distinguish two cases. In the first case, the length of the probe $L>-\sigma N$, where $\sigma$ is the superhelical density of the target DNA, which can vary from $-0.03$ to $-0.09$ (Vologodskii (1992)), N is the length of the target, which can vary from $10^3$ to $10^6$ bp. This condition means that the length of the probe L is greater than that is necessary to completely relax superhelical stress within the target. In this case the full-length D-loop formation will induce the positive superhelical stress which will facilitate the probe strand(s) displacement, until $-\sigma N$ base pairs remain within the hybrid DNA structure. In the case of double D-loops, the displaced regions of the probe DNA strands would form the probe-probe DNA duplex. Further displacement would generate negative superhelical stress, which makes the further displacement energetically unfavorable. Thus, in this case the slow initiation step is accelerated by the positive superhelical stress and this positive superhelical stress also prevents the return of the structure to a non-nucleated "zero" state. Consequently, for $L>-\sigma N$, the effect of a slow initiation step will be less pronounced for supercoiled DNA targets than for linear and nicked. In the opposite case, where $L<-\sigma N$, the target DNA remains negatively supercoiled even after complete invasion of the probe DNA strand(s), which corresponds of the "zero" position of the hybrid DNA D-loop structure. Thus, negative superhelical stress would facilitate returns of the structure to the "zero" position. Consequently, the effect of a slow initiation step in this case will be greater for negatively supercoiled targets than for linear or nicked targets. In Appendix 5 we show that for "short" double D-loops ($L<1v$) within the DNA targets, where $L<-\sigma N$, the ratio of dissociation times for double D-loops with and without slow reversible initiation step is about $\tau_n/(2\tau_1)$, which is about L times greater than the same ratio for linear (or nicked) targets.

Discussion. We analyzed the dissociation of branched DNA structures in the presence of a slow reversible initiation step. This initiation step brings in an additional term into dependence of the average dissociation time ($\tau$) on the length of the DNA structure (L). The additional term is linear on L, in contrast with the "classic" quadratic length dependence obtained for branched DNA dissociation without a slow initiation step (for review see (Hsieh et al., (1995)). This linear term is a total "penalty time" for the repetitive returning of the DNA structure to the "zero" non-disturbed state, from which the slow initiation step must be repeated again. This linear term makes a major contribution to the dissociation time for a structures when their length (bp) is shorter than the ratio of the initiation step time to the branch migration step time. According to our estimations, this ratio can vary from $10^3$ to $10^6$ under various ionic conditions.

There are two types of DNA structures where dissociation is expected to proceed via a slow reversible initiation step: Y-like DNA structures and double D-loop DNA hybrids. Both of these DNA structures may function as intermediates in DNA replication and homologous DNA recombination.

Two-dimension gel electrophoresis of DNA replication intermediates is commonly used for mapping the replication origins and measurement of rates of DNA replication for (review see Friedman et al., (1983)). Gel electrophoresis can be used only when the characteristic time of dissociation (lifetime) of replication intermediates under a given temperature and ionic strength is longer than the time of electrophoresis. Equations 5 and 22 permit calculation of the lifetimes of DNA replication intermediates using small number of empirical parameters, and, consequently, allow estimations of the minimal length of the DNA intermediate which can be detected by this method under given conditions.

Another process which produces branched DNA structures is the reaction between double-stranded DNA, target, and RecA protein coated single-stranded DNA, probes, followed by the removal of the RecA protein from the products of reaction. Reaction of RecA protein coated single-stranded DNA probes with double-stranded DNA targets produces branched DNA-DNA hybrid products, some of which can be similar to homologous DNA recombination intermediates in vivo (for review see (Kowalczykowski et al. in Gene Targeting (Vega, Ed.) pp.167–210, CRC Press, Inc. (1995)). In vitro, this homologous DNA targeting reaction is used for DNA cloning, isolation, mapping and modification (for review see Pati et al. in Molecular Biology of Cancer, ed. Bertino (Academic Press, San Diego), Volume III, 1601–1625 (1997)). When two complementary single-stranded RecA coated DNA probes are homologous to the internal region of a double-stranded DNA target, then the reaction leads to formation of double D-loop DNA hybrids (Sena et al., (1993); Jayasena et al. (1993)). Y-like DNA structures also can be obtained in this reaction, if the DNA probes are homologous to the flanking region of the linear target DNA. The kinetic stability of these DNA structures (i.e. their characteristic times of dissociation) is an important parameter for their various genetic applications because after removing RecA protein dissociation of these structures is irreversible, thus, all manipulations with the structures must be completed during the time shorter then their characteristic dissociation time.

RecA-mediated DNA targeting reactions can tolerate significant DNA sequence heterology between the probe and the target DNAs (Radding (1988)). For gene cloning and DNA isolation applications (for example, for separation of "wild type" and mutated forms of homologous genes) it is important to know how the positions of DNA sequence heterologies affect the kinetic stabilities of the branched DNA structures. According to our analysis, DNA sequence heterologies localized at the end of the structure would significantly accelerate dissociation of the structure because they decrease the decelerating effect of a slow reversible initiation step (in the limit case making this step irreversible). For double D-loop DNA hybrids this acceleration of dissociation takes place if the length of the structure is smaller than the ratio of nucleation step time to the elongation step time. Since according to our estimations this ratio is at least greater then 1000 bp, the DNA probes commonly used in the targeting reactions (100–300 bp long) satisfy this requirement. The destabilizing effects of heterologous DNA sequences in the middle of the structure are less pronounced. Moreover, at least in the case of double D-loops an opposite effect (i.e. kinetic stabilization by heterologies) is possible for longer heterologies of 14 bases or more localized at the middle of the structure, most probably because these heterologies impede rotation of the DNA duplexes which accompanies DNA branch migration (Belotserkovskii et al. (1999)). Thus, if the "wild-type" DNA target is to be purified from the "mutant" DNA target using a double D-loop or a Y-DNA structure formation, the DNA probe, which is completely homologous to the wild-type targets, is designed in such way that the heterology between the mutant target and the probe is localized at one flank of the DNA probes.

It is well-recognized that double D-loops have a certain advantage over singel D-loops. For example, in the case of non-supercoiled target DNAs the dissociation times of single D-loops which are shorter than 1000 bp is less than 12 seconds (Beattie et al. (1977)), while for double D-loops with the lengths about 60 bp or more, the dissociation time at similar ambient conditions is at least several hours (Sena et al. (1993); Jayasena et al. (1993); Belotserkovskii et al. (1999)). Thus, for many manipulations with non-supercoiled DNA targets, like linear genomic DNA and open-circular DNA in λ-phage DNA libraries, only double D-loops can be used, According to our analysis, even in the case of supercoiled target DNA, where both single and double D-loops are kinetically stable, double D-loops have potential advantage over single D-loops, because double D-loops can provide a greater kinetic discrimination between D-loops formed with the target sequence, which is completely homologous to the probe, where one end of the target sequence is heterologous to the probe. A single D-loop dissociation pathway does not include a slow initiation step. Thus, the only effect of heterologies between the probe and the target DNA sequences within single D-loops would be decrease of the length of the probe-target duplex which has to be displaced during dissociation. In contrast, for completely homologous double D-loops, a slow reversible initiation step has a major effect on the dissociation time. Heterologous sequences at the end of the probe DNA strands which are extruded from the double D-loop, would readily hybridize to each other, providing a fast irreversible initiation step. This additional effect of heterologies accelerates double D-loop dissociation several orders of magnitude. This increased kinetic discrimination is used for sequence-specific DNA capture.

Appendix 1 Dissociation Times of Y-like DNA Structure in the Presence of DNA Sequence Mismatch. A mismatch at position m can be described as a point from which the probabilities of steps to the right and to the left (p and q, respectively) are different (Panyutin and Hsieh, (1993); Biswas et al., (1998)):

$$T(m)=qT(m-1)+pT(m+1)+\tau_1 \qquad [23]$$

For all other points $$T(x)=[T(x-1)+T(x+1)]/2+\tau_1 \qquad [24]$$

And for edge conditions $$T(0)=T(1)+\tau_n \quad [25]$$

and $$T(L)=0 \quad [26]$$

The solution of this system is determined in the form $$T(x)=C_{01}+C_{11}x-\tau_1 x^2 \quad [27]$$

for $0 \leq x \leq m$
and $$T(x)=C_{02}+C_{12}x-\tau_1 x^2 \quad [28]$$

for $m \leq x \leq L$

Since at $x=m$, both Eq. 27 and Eq. 28 must be satisfied, then $$C_{01}+C_{11}m=C_{01}+C_{12}m \quad [29]$$

From Eqs. 25–29 the average dissociation time $\tau$ can be determined $$\tau=T(0)=C_{01}=[\tau_n-\tau_1][m+(L-m)s]+\tau_1[m^2+(L-m)^2+2m(L-m)s] \quad [30]$$

where $s=q/p$.

The case $s<1$ which corresponds to DNA mismatch elimination during dissociation of the DNA structure. At $s=0$ the limit case (Eq. 8) is obtained. The case $s>1$ corresponds to mismatch formation during dissociation, which strongly impedes dissociation of the structure, both in the presence and in the absence of the slow initiation step (Panyutin and Hsieh (1993); Biswas et al., J. Molec. Biol. 279:795–806 (1998)).

Appendix 2. Fluctuation of Distances between DNA Four-Way Junctions in Double-Nucleated Double D-loop DNA Structure. Let Lk be the number of links between contours formed by the probe and the target DNA strands (see FIG. 18C). In the most energetically favorable state the number of base pairs between junctions $r_0=\gamma Lk$, where $\gamma$ is the number of base pairs per one helical turn for a non-deformed DNA double helix. If, due to non-synchronized movement of four-way DNA junctions, the total number of base pairs in the probe-target duplexes will change to $r=r_0+\Delta r$, the most energetically favorable number of links would be $Lk_{opt}=r/\gamma$. However, since the number of links between the contours can not be changed during the four-way junctions migration, the non-synchronized movement of four-way junctions causes deformation of probe-target DNA duplexes. The measure of this deformation is the superhelical density $\sigma$ (for review see (Vologodskii (1992))

$$\sigma=(Lk-Lk_{opt})/Lk_{opt}=\sigma r/r \approx \Delta r/r_0 \quad [31]$$

If we assume that the energy of this deformation $\Delta G$ could be roughly estimated from the formula obtained for the supercoiling energy in circular closed DNA (for review see (Vologodskii (1992)) then $$\Delta G(\Delta r)=10RT_a r\sigma^2 \approx 10RT_a(\Delta r)^2/r_0 \quad [32]$$

where $RT_a$ is the product of the universal gas constant and the absolute temperature.

The average fluctuation of distance between junctions $\delta r$ can be estimated from equation $$\Delta G(\delta r)=RT_a \quad [33]$$

thus $$\delta r \approx (r_0/10)^{1/2} \quad [34]$$

Appendix 3: Asymptotic Length Dependence for the Dissociation Time of the Double D-loop DNA Structure. Let us analyze the asymptotic dependence of the dissociation time on length for the cases of "short" ($L1/v$) and "long" ($L>1/v$) double D-loops. Here we assume that parameters L and $1/v$ are $>1$, and parameter $\phi$ (Eq. 22a) is of the order of unity. Thus, if we consider the asymptotic condition $L<1/v$, it is implied that $\phi L<1/v$. Let us compare the first term (designated as $F_1$) of Eq. 22a:

$$F_1=(\phi-1)[(1+2v)/4v^2][1-(1+2v)^{-L}-2vL/(1+2v)] \quad [35]$$

with the second term $$F_2=\phi(L-1)L/2 \approx \phi L^2/2 \quad [36]$$

and with the third term $$F_3 L/(2\phi) \quad [37]$$

Let us prove that the absolute value of $F_1$ ($abs(F_1)$) is always smaller than $F_2$.

Using a geometric series expansion it can be obtained $$1-(1+2v)^{-L}=[2v/(1+2v)]_{i=0}\Sigma^{L-1}(1+2v)^{-i} \quad [38]$$

and $$1-(1+2v)^{-L}-2vL/(1+2v)=-[2v/(1+2v)]_{i=0}\Sigma^{L-1}[1-(1+2v)^{-i}] \quad [39]$$

where $_{i=0}\Sigma^{L-1}$ means summation for all integers i from 0 to $L-1$. By geometric series expansion of each difference $[1-(1+2v)^{-i}]$ followed by regrouping of the terms, it can be obtained $$_{i=0}\Sigma^{L-1}[1-(1+2v)^{-i}]=[2v/(1+2v)]_{i=0}\Sigma^{L-2}(L-i-1)(1+2v)^{-i} \quad [40a]$$

For all positive $v$ $$_{i=0}\Sigma^{L-2}(L-i-1)(1+2v)^{-i}<_{i=0}\Sigma^{L-2}(L-i-1)=L(L-1)/2 \quad [40b]$$

Substituting this results in Eq.35 and taking into account that $\phi \geq 1$ we obtain $$abs(F_1)>[(\phi-1)/(1+2v)][L(L-1)/2]<\phi(L-1)L/2 \quad [41]$$

Thus, $abs(F_1)<F_2$.
Consequently if $F_3>F_2$, (i.e. $(1/v)>\phi(L-1)$) then $F_3>F_1$.
From Eq. 38 it is seen that $$1-(1+2v)^{-L}<[2v/(1+2v)]L \quad [42]$$

Thus, $$abs(F_1)<(\phi-1)vL/2 \quad [43]$$

Consequently, if $(L-1)L>L/v$ (which at $\phi \geq 1$ means that $F_2>F_3$) then $\phi(L-1)L/2$ ($\phi-1)L/2v$, i.e. $F_2>abs(F_1)$. Thus, the first term does not affect the asymptotic length dependence for "long" and for "short" double D-loop DNA structures.

Appendix 4: Dissociation of the Double D-loop DNA Structure with Very Fast Irreversible Nucleation at one of the Flanks. Here we assume that irreversible nucleation at the left flank of the double D-loop precedes the double D-loop dissociation process and consequently the single-nucleated state corresponds to the "zero" state of the system. The equations describing this process are the same as for usual D-loops except the condition of "reflection" at the left edge. For the double nucleated state Eq. 11 is substituted by $$T_{dn}(0, z)=T_{dn}(1, z)+\tau_2 \quad [44]$$

and for single-nucleated state Eq. 16 is substituted by $$T_{sn}(0)=[k_1/(2k_1+k_n)]T_{sn}(1)+[k_n/(2k_1+k_n)]T_{dn}(0,0)+1(2k_1+k_n) \quad [45]$$

The solution of the system for the "zero" initial state is $$\tau(L)/\tau_1=(\phi-1)\{[(1+2v)/2(1+v)v^2][1-(1+2v)^{-L}-2v(1+v)L/(1+2v)]+L^2\}+L^2 \quad [46]$$

Let us analyze the term in the figure brackets. By using the modification of equations similar to those used in Appendix 3, and taking into account that $$L(L^{-1})/2-{}_{i=0}\Sigma^{L-2}(L^{-i}-1)(1+2v)^{-i}={}_{i=0}\Sigma^{L-2}(L^{-i}-1)[1-(1+2v)^{-i}]=$$

$$=[2v/(1+2v)]_{i=0}\Sigma^{L-3}(L^{-i}-2)_{j=0}\Sigma^{L-1}(1+2v)^{-i} \quad [47a]$$

$${}_{i=0}\Sigma^{L-3}(L^{-i}-2)_{j=0}\Sigma^i(1+2v)^{-j}<{}_{i=0}\Sigma^{L-3}0(L-3(L^{-i}-2)(i+1)\approx L^3/6 \quad [47b]$$

it can be shown that the term in the figure brackets in Eq. 46 is smaller than $vL^3$. For "short" double D-loop DNA structures $L<1/v$, which is equivalent to $vL_3<L^2$. Thus for "short" double D-loops $$\tau(L)\approx\tau_1 L^2 \quad [48]$$

To obtain the asymptotic equation for "long" double D-loops let us rewrite Eq. 46 in the form $$\tau(L)/\tau_1=(\phi-1)\{[(1+2v)/2(1+v)v^2][1-(1+2v)^{-L}-2v(1+v)L/(1+2v)]\}+\phi L^2 \quad [49]$$

The term in figure brackets in Eq. 49 is less than $L/v$ (see Appendix 3), and for "long" double D-loops $L/v<L^2$. Consequently for "long" double D-loops the asymptotic equation is $$\tau(L)\approx\phi\tau_1 L^2=\tau_2 L^2 \quad [50]$$

Appendix 5. Dissociation of "short" Double D-loops within Supercoiled DNA Targets. Since we consider only "short" double D-loops ($L<1/v$), we neglect the possibility of the double-nucleated state formation. Thus, we consider the movement of only one four-way DNA junction in a similar way as for a Y-like DNA structure. Let $k_+(x)$ and $k_-(x)$ be the rate constant for the step from the position x to the position x+1, and for the step from the position x to the position x−1, respectively. We used the same approach as for derivation of Eq. 13, with the exception that here we neglect the probability of the second nucleation, and we obtain:

$$T(x)=[k_+(x)/(k_+(x)+k_-(x))]T(x+1)+[k_-(x)/(k_+(x)+k_-(x))]T(x-1)+1/(k_+(x)+k_-(x)) \quad [51]$$

The edge conditions:

$$T(0)\approx T(1)+\frac{1}{2}k_+(0) \quad [52]$$

and $$T(L)=0 \quad [53]$$

To solve Eq. 51 it is convenient to introduce function $$U(x)=T(x)-T(x+1) \quad [54]$$

From Eqs. 51, 52 corresponding equations for $U(x)$ can be obtained $$U(x)=[k_-(x)/(k_+(x)]U(x-1)+1/k_+(x) \quad [55]$$

$$U(0)=\frac{1}{2}k_+(0) \quad [56]$$

The function $U(x)$ can be presented in the form $$U(x)=f(x)h(x) \quad [57]$$

where $f(x)$ satisfies equations:

$$f(x)=[k_-(x)/(k_+(x)]f(x-1) \quad [58]$$

$$f(0)=1/[2k_+(0)] \quad [59]$$

From Eqs. 55–59 it can be obtained $$h(x)=h(x-1)+1/(f(x)k_+(x)) \quad [60]$$

$$h(0)=1 \quad [61]$$

From Eqs. 58–59

$$f(x)=(\frac{1}{2}k_+(0))_{i=1}\Pi^x[k_-(i)/(k_+(i)]=(\frac{1}{2}k_+(x))_{i=0}\Pi^x[k_-(i)/(k_+(i-1)] \quad [62]$$

where $_{i=1}\Pi^x$ designates multiplication for all integers i from 1 to x.

The rate constants $k_-(i)$ and $k_+(i-1)$ correspond to the passing through the same transition state but in the opposite directions. Thus for $i>1$ $$k_-(i)/k_+(i-1)=(k_1/k_n)\exp\{[G(i)-G(i-1)]/RT_a\} \quad [63a]$$

and $$k_-(1)/(k_+(0)=(k_1/k_n)\exp\{[G(1)-G(0)]/RT_a\} \quad [63b]$$

where $G(i)$ is supercoiling energy, and $k_1$ and $k_n$ are elongation and nucleation rate constants for non-supercoiled target DNA.

Thus, $$f(x)=(\frac{1}{2}k_+(x))(k_1/k_n)\exp\{[G(x)-G(0)]/RT_a\} \quad [64]$$

and $$h(x)=1+{}_{i=1}\Sigma^x1/(f(i)k_+(i))=1+{}_{i=1}\Sigma^x2(k_n/k_1)\exp\{-[G(i)-G(0)]/RT_a\} \quad [65]$$

The rate constant $k_+(x)$ from Eq. 64 is in between $k_1$ and $k_1\exp\{[G(x)-G(x+1)]/RT_n\}$, depending on the topology of the transition state for one step of DNA branch migration.

The average dissociation time can be obtain from the equation $$\tau=T(0)={}_{x=0}\Sigma^{L-1}U(x) \quad [66]$$

where $U(0)$ is determined from Eq. 56, and $U(x)$ at $x>0$ is determined from Eq. 57.

This equation can be simplified for the case of the short probes and the long target DNAs with high negative superhelical densities. The formation of the D-loop with the length L−x is topologically equivalent to opening of L−x base pairs within the target DNA. Thus the supercoiling energy $G(x)$ is determined by equation $$G(x)=10RT_aN[\sigma+(L-x)/N]^2 \quad [67]$$

(see Vologodskii (1992) for review). If $L<-\sigma N$, and $\sigma\approx-0.05$, then the factor $\exp\{[G(x)-G(0)]/RT_a\}$ increases approximately e times when the x value is increased by 1.

Thus, to estimate the dissociation time τ (within the error less than one order of magnitude), in Eq. 66 we can omit all terms except $U(L-1)$, and in Eq. 65 we can omit all terms except 1.

Thus, $$\tau\approx(\tau_n/2)\exp\{\Delta G/RT_a\} \quad [68]$$

where $\Delta G=G(L)-G(0)$ is the decrease in the supercoiling energy for the full-size D-loop formation. In the case of the fast irreversible initiation from one end, $(\tau_n/2)$ in this equation is substituted by $\tau_1$. Thus the slow initiation step decelerates dissociation approximately $\tau_n/(2\tau_1)$ times.

This invention has been detailed both by example and by description. It should be apparent that one having ordinary skill in the relevant art would be able to surmise equivalents to the invention as described in the claims which follow but which would be within the spirit of the foregoing description and examples. It should be realized that those equivalents and various modifications as may be apparent to those of skill in the art to which the invention pertains also fall within the scope of the invention as defined by the appended claims. All herein cited patents, patent applications, publications, references, and references cited therein are hereby expressly incorporated by reference in their entirety.

We claim:

1. A composition comprising a double D-loop, said double-D loop comprising:
   a target nucleic acid;
   a first single stranded targeting polynucleotide comprising: a central region and two flanking regions which flank the central region of said first single stranded targeting polynucleotide and which form homology clamps with said target nucleic acid;
   a second single stranded targeting polynucleotide comprising: a central region and two flanking regions which flank the central region of said second single stranded targeting polynucleotide and which form homology clamps with said target nucleic acid; and
   a locking complex formed by the central regions of said first and said second single stranded polynucleotides,
   wherein said locking complex is a triplex or a quadruplex.

2. A composition comprising a double D-loop, said double D loop comprising:
   a target nucleic acid;
   a first single stranded targeting polynucleotide comprising: a central region and two flanking regions which flank the central region of said first single stranded targeting polynucleotide and which form homology clamps with said target nucleic acid;
   a second single stranded targeting polynucleotide comprising: a central region and two flanking regions which flank the central region of said second single stranded targeting polynucleotide and which form homology clamps with said target nucleic acid; and
   a locking complex formed by the central regions of said first and said second single stranded polynucleotides,
   wherein said locking complex comprises a quadruplex.

3. A composition comprising a double D-loop, said double D loop comprising:
   a target nucleic acid;
   a first single stranded targeting polynucleotide comprising: a central region and two flanking regions which flank the central region of said first single stranded targeting polynucleotide and which form homology clamps with said target nucleic acid;
   a second single stranded targeting polynucleotide comprising: a central region and two flanking regions which flank the central region of said second single stranded targeting polynucleotide and which form homology clamps with said target nucleic acid; and
   a locking complex formed by the central regions of said first and said second single stranded polynucleotides,
   wherein said locking complex comprises Z-form duplex.

4. A composition comprising a double D-loop, said double D loop comprising:
   a target nucleic acid;
   a first single stranded targeting polynucleotide comprising: a central region and two flanking regions which flank the central region of said first single stranded targeting polynucleotide and which form homology clamps with said target nucleic acid;
   a second single stranded targeting polynucleotide comprising: a central region and two flanking regions which flank the central region of said second single stranded targeting polynucleotide and which form homology clamps with said target nucleic acid; and
   a locking complex formed by the central regions of said first and said second single stranded polynucleotides,
   wherein said locking complex comprises a triplex.

5. The composition of claim 4 further comprising a secondary polynucleotide that stabilizes said triplex.

6. A composition comprising a double D-loop comprising a target nucleic acid and a first and a second single stranded targeting polynucleotide, wherein said first and said second targeting polynucleotides are substantially complementary to each other and further wherein said first and said second targeting polynucleotides each comprise:
   a first and second homology clamp wherein said first and said second homology clamps substantially correspond to or are substantially complementary to a preselected target nucleic acid sequence; and
   a locking nucleic acid sequence positioned between said first and said second homology clamps wherein said locking nucleic acid sequence is capable of stabilizing a locking complex in a double D-loop structure, wherein said locking complex is a triplex or a quadruplex.

7. The composition according to claim 6 further comprising at least one recombinase.

8. The composition according to claim 6 further comprising a protein bound to said locking complex.

9. A composition comprising a double D-loop, said double-D loop comprising:
   a target nucleic acid;
   a first single stranded targeting polynucleotide comprising: a central region and two flanking regions which flank the central region of said first single stranded targeting polynucleotide and which form homology clamps with said target nucleic acid;

a second single stranded targeting polynucleotide comprising: a central region and two flanking regions which flank the central region of said second single stranded targeting polynucleotide and which form homology clamps with said target nucleic acid; and a locking complex formed by the central regions of said first and said second single stranded polynucleotides, wherein said locking complex comprises at least one non-Watson-Crick base pair.

10. The composition according to any one of claims 1, 4, 2, 3 or 9, wherein said locking complex comprises DNA, RNA or peptide nucleic acid.

11. The composition according to any one of claims 1, 4, 2, 3 or 9, wherein at least one of said single stranded targeting polynucleotides is linked to at least one protein substituent.

12. The composition according to any one of claims 1, 4, 2, 3 or 9, wherein at least one of said single stranded targeting polynucleotides is linked to at least one non-protein chemical substituent.

13. The composition of claim 12 wherein said substituent is selected from the group consisting of intercalators, cross-linking moieties, labels, photoactive moieties, nucleic acid scission inducing moieties, purification tag moieties, and nucleic acid modification moieties.

14. A cell comprising a composition according to any one of claims 1, 4, 2, 3 or 9.

15. The cell of claim 14 which is a eukaryotic cell.

16. The cell of claim 14 which is a prokaryotic cell.

17. A composition according to any one of claims 1, 4, 2, 3 or 9, further comprising at least one recombinase.

18. The composition of claim 17 wherein said recombinase is a species of prokaryotic recombinase.

19. The composition of claim 18, wherein said prokaryotic recombinase is a species of prokaryotic RecA protein.

20. The composition of claim 19, wherein said RecA protein species is *E. coli* RecA.

21. The composition of claim 17, wherein said recombinase is a species of eukaryotic recombinase.

22. The composition of claim 21, wherein said recombinase is a Rad51 recombinase.

23. The composition of claim 22, wherein said eukaryotic recombinase is a complex of recombinase proteins.

24. A kit comprising a first and a second single stranded targeting polynucleotide, wherein said first and said second targeting polynucleotides are substantially complementary to each other and further wherein said first and said second targeting polynucleotides each comprise:

a first and a second homology clamp that wherein said first and said second homology clamps substantially correspond to or are substantially complementary to a preselected target nucleic acid sequence; and a locking nucleic acid sequence positioned between said first and said second homology clamps wherein said locking nucleic acid sequence is capable of stabilizing a locking complex in a double D-loop structure, wherein said locking complex is a triplex or a quadruplex.

25. The kit according to claim 24 further comprising at least one recombinase.

* * * * *